(12) United States Patent
Kruegel et al.

(10) Patent No.: US 11,912,707 B2
(45) Date of Patent: Feb. 27, 2024

(54) MITRAGYNINE ALKALOIDS AS OPIOID RECEPTOR MODULATORS

(71) Applicant: The Trustees of Columbia University in the City of New York, New York, NY (US)

(72) Inventors: Andrew Kruegel, Secaucus, NJ (US); Dalibor Sames, New York, NY (US); Madalee G. Wulf, Beverly, MA (US); Jonathan A. Javitch, Dobbs Ferry, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 104 days.

(21) Appl. No.: 17/189,456

(22) Filed: Mar. 2, 2021

(65) Prior Publication Data
US 2021/0179618 A1 Jun. 17, 2021

Related U.S. Application Data

(62) Division of application No. 16/088,311, filed as application No. PCT/US2017/023977 on Mar. 24, 2017, now Pat. No. 10,961,244.

(60) Provisional application No. 62/313,360, filed on Mar. 25, 2016.

(51) Int. Cl.
| | |
|---|---|
| *C07D 471/14* | (2006.01) |
| *A61K 45/06* | (2006.01) |
| *A61K 31/4375* | (2006.01) |
| *C07D 471/20* | (2006.01) |
| *A61K 31/437* | (2006.01) |
| *A61P 25/00* | (2006.01) |
| *A61K 31/438* | (2006.01) |

(52) U.S. Cl.
CPC .......... *C07D 471/14* (2013.01); *A61K 31/437* (2013.01); *A61K 31/438* (2013.01); *A61K 31/4375* (2013.01); *A61K 45/06* (2013.01); *A61P 25/00* (2018.01); *C07D 471/20* (2013.01)

(58) Field of Classification Search
CPC ..... C07D 471/14; C07D 471/20; A61P 25/00; A61K 31/4375; A61K 31/438; A61K 45/06
See application file for complete search history.

(56) References Cited

U.S. PATENT DOCUMENTS

| | | | |
|---|---|---|---|
| 8,337,941 B2 | 12/2012 | Gubernator et al. | |
| 8,648,090 B2 | 2/2014 | Takayama et al. | |
| 9,075,014 B2 | 7/2015 | Sames et al. | |
| 9,988,377 B2 | 6/2018 | Sames et al. | |
| 10,183,919 B2 | 1/2019 | Kruegel et al. | |
| 10,961,244 B2 * | 3/2021 | Kruegel | A61K 45/06 |
| 11,046,692 B2 * | 6/2021 | Pasternak | A61P 25/00 |
| 11,760,758 B2 * | 9/2023 | Kruegel | C07D 471/20 514/278 |
| 2001/0037021 A1 | 11/2001 | Blanchard et al. | |
| 2003/0092214 A1 | 5/2003 | Williams et al. | |
| 2008/0194522 A1 | 8/2008 | Chen et al. | |
| 2009/0209474 A1 | 8/2009 | Roegel et al. | |
| 2009/0221623 A1 | 9/2009 | Takayama et al. | |
| 2010/0035279 A1 | 2/2010 | Gubernator et al. | |
| 2012/0115849 A1 | 5/2012 | Demopulos et al. | |
| 2013/0171664 A1 | 7/2013 | Sames et al. | |
| 2013/0190497 A1 | 7/2013 | Gubernator et al. | |
| 2015/0056699 A1 | 2/2015 | Sames et al. | |
| 2017/0217913 A1 | 8/2017 | Kruegel et al. | |
| 2018/0134708 A1 | 5/2018 | Pasternak et al. | |
| 2019/0047970 A1 | 2/2019 | Kruegel et al. | |
| 2019/0084949 A1 | 3/2019 | Kruegel et al. | |
| 2019/0084983 A1 | 3/2019 | Kruegel et al. | |
| 2020/0308306 A1 * | 10/2020 | Xu | C07K 16/16 |
| 2021/0179619 A1 * | 6/2021 | Kruegel | C07D 471/14 |
| 2022/0135564 A1 * | 5/2022 | Kruegel | A61P 25/36 514/285 |

(Continued)

FOREIGN PATENT DOCUMENTS

| | | |
|---|---|---|
| WO | WO 2006/023821 A2 | 3/2006 |
| WO | WO 2006/026368 A1 | 3/2006 |

(Continued)

OTHER PUBLICATIONS

Kerschgens; Chem. Commun., 2012, 48, 12243-12245. (Year: 2012).*

(Continued)

*Primary Examiner* — Daniel R Carcanague
(74) *Attorney, Agent, or Firm* — Gary J. Gershik

(57) ABSTRACT

The present invention provides a compound having the structure:

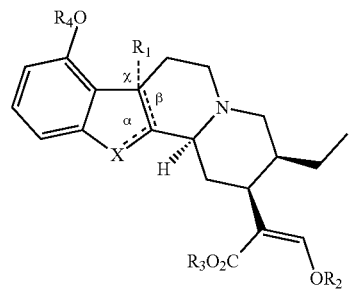

or a pharmaceutically acceptable salt or ester thereof, and a method of treating a subject afflicted with pain, a depressive disorder, a mood disorder or an anxiety disorder by administering the compound to the subject.

11 Claims, 6 Drawing Sheets

(56) References Cited

U.S. PATENT DOCUMENTS

2023/0250098 A1* 8/2023 Majumdar ........... C07D 471/20 514/278

FOREIGN PATENT DOCUMENTS

| WO | WO 2007/022263 A1 | 2/2007 |
|---|---|---|
| WO | WO 2008/013997 A2 | 1/2008 |
| WO | WO 2011/094560 A1 | 8/2011 |
| WO | WO 2013/028999 A1 | 2/2013 |
| WO | WO 2014/170704 A1 | 10/2014 |
| WO | WO 2015/138791 A1 | 9/2015 |
| WO | WO 2016/086158 A1 | 6/2016 |
| WO | WO 2017/049158 A1 | 3/2017 |
| WO | WO 2017/165738 A1 | 9/2017 |
| WO | WO 2018/170275 A1 | 9/2018 |
| WO | WO 2020/037136 A1 | 2/2020 |
| WO | WO-2022234524 A1 * | 11/2022 |

OTHER PUBLICATIONS

Kruegel; "Chemical and Biological Explorations of Novel Opioid Receptor Modulators", Ph.D. Thesis, Columbia University, Aug. 26, 2015, 945 pages. (Year: 2015).*
Ma; Org. Lett. 2007, 9, 18, 3491-3494. (Year: 2007).*
Ma; J. Org. Chem. 2009, 74, 264-273. (Year: 2009).*
Takayama; Tetrahedron Letters 1995, 36, 9337-9340. (Year: 1995).*
Takayama; Chem. Pharm. Bull. 2004, 52, 916-928. (Year: 2004).*
National Center for Biotechnology Information. PubChem Compound Summary for CID 90360629, 9-Hydroxycorynantheidine. https://pubchem.ncbi.nlm.nih.gov/compound/9-Hydroxycorynantheidine. Create Date Feb. 13, 2015. (Year: 2015).*
International Preliminary Report on Patentability dated Sep. 25, 2018, including Written Opinion of the International Searching Authority dated Aug. 7, 2017, in connection with PCT International Application No. PCT/US2017/023977.
International Search Report dated Aug. 7, 2017 in connection with PCT International Application No. PCT/US2017/023977.
International Search Report dated Jan. 6, 2020 in connection with PCT International Application No. PCT/US2019/046677.
Kruegel et al. "Synthetic and Receptor Signaling Explorations of the Mitragyna Alkaloids: Mitagynine as an Atypical Molecular Framework for Opioid Receptor Modulators", Journal of the American Chemical Society, 2016, vol. 168, pp. 6754-6764.
Raffa et al. "Orally Active Opioid Compounds from a Non-Poppy Source", *J. Med. Chem.*, 2013, vol. 56, pp. 4840-4848.
Takayama et al. "Studies on the Synthesis and Opioid Agonistic Activities of Mitragynine-Related Indole Alkaloids: Discovery of Opioid Agonists Structurally Different from Other Opioid Ligands", *J. Med. Chem*, 2002, vol. 45, pp. 1949-1956.
Written Opinion of the International Searching Authority dated Aug. 7, 2017 in connection with PCT International Application No. PCT/US2017/023977.
Written Opinion of the International Searching Authority dated Jan. 6, 2020 in connection with PCT International Application No. PCT/US2019/046677.

* cited by examiner

MITRAGYNINE ALKALOIDS AS OPIOID RECEPTOR MODULATORS

CROSS-REFERENCE TO RELATED APPLICATIONS

This application is a divisional of U.S. application Ser. No. 16/088,311, filed Sep. 25, 2018, now allowed, which is a § 371 national stage of PCT International Application No. PCT/US2017/023977, filed Mar. 24, 2017, claiming the benefit of U.S. Provisional Application No. 62/313,360, filed Mar. 25, 2016, the contents of each of which are hereby incorporated by reference.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

The opioid receptors, and in particular, the mu-opioid receptor (MOR), are among the longest and most intensely studied molecular signaling systems in the central nervous system (Pasternak, G. W. et al. 2013). Likewise, the prototypical small molecule agonist of these receptors, morphine, has been used by humans as an important analgesic and recreational euphoriant since ancient times. Indeed, MOR agonists, including not only morphine itself, but also a vast number of synthetic and semi-synthetic opioids, remain the gold standard of pain therapy. Unfortunately, acute MOR activation is also associated with serious side effects, including respiratory depression, constipation, sedation, nausea, and itching (Pasternak, G. W. et al. 2013; Inturrissi, C. E. 2002). At sufficiently high doses, the evoked respiratory depression can be severe enough to cause death. Further, the pronounced euphoria produced by MOR agonists makes them major drugs of abuse. These properties have made overdose from prescription opioid analgesics a leading cause of accidental death in the United States, killing more than 18,000 people in 2014 (NIDA 2015). Another shortcoming of MOR agonists is the rapid development of tolerance to their analgesic effects. Thus, continuing escalation of dose is required to maintain an equivalent level of pain management. Similarly, when they are abused, tolerance to the euphoric effects of opioids is also rapidly developed. Thus in either case, chronic use often results in severe physical dependence on MOR agonists due to cellular- and circuit-level adaptations to continuous receptor stimulation. Accordingly, much effort has been dedicated to the development of new MOR agonists retaining potent analgesic effects, while mitigating or eliminating the deleterious side effects of the agents currently in use (Pasternak, G. W. et al. 2013; Inturrissi, C. E. 2002; Pasternak, G. W. et al. 2010; Grinnell, S. G. et al. 2014; Largent-Milnes, T. et al. 2010; Stevenson, G. W. et al. 2015).

Historically, MOR agonists have also been applied in the treatment of mood disorders, notably including major depressive disorder (MDD). Indeed, until the mid-20th century, low doses of opium itself were used to treat depression, and the so called "opium cure" was purportedly quite effective (Kraepelin, E. 1905). With the advent of tricyclic antidepressants (TCAs) in the 1950s however, the psychiatric use of opioids rapidly fell out of favor and has been largely dormant since, likely due to negative medical and societal perceptions stemming from their abuse potential. However, there have been scattered clinical reports (both case studies and small controlled trials) since the 1970s indicating the effectiveness of MOR agonists in treating depression. The endogenous opioid peptide β-endorphin, as well as a number of small molecules, have all been reported to rapidly and robustly improve the symptoms of MDD and/or anxiety disorders in the clinical setting, even in treatment resistant patients (Gerner, R. H. et al. 1980; Stoll, A. L. 1999; Dean, A. J. et al. 2004; Shapira, N. A. et al. 2001; Shapira, N. A. et al. 1997; Emrich, H. M. et al. 1982; Karp, J. F. et al. 2014; Bodkin, J. A. et al. 1995). These results have been recapitulated in rodent models, where a variety of MOR agonists show antidepressant effects (Besson, A. et al. 1996; Rojas-Corrales, M. O. et al. 2002; Fichna, J. et al. 2007; Rojas-Corrales, M. O. et al. 1998). Most recently, it was found that the atypical antidepressant tianeptine, which has been used clinically for several decades and extensively studied in rodents and other mammalian species, is an MOR agonist, suggesting that this agent exerts its antidepressant effects via direct MOR activation (Gassaway, M. M. et al. 2014).

SUMMARY OF THE INVENTION

The present invention provides a compound having the structure:

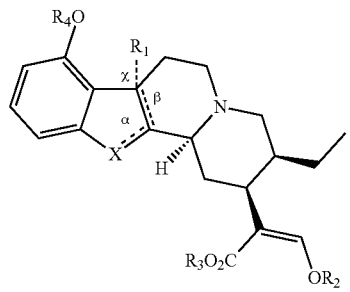

wherein

X is N or NH;

$R_1$ is —OH, —O-alkyl, —O(CO)-alkyl or is absent;

$R_2$ is —H or -alkyl;

$R_3$ is —H or -alkyl;

$R_4$ is —H or -alkyl;

α is a bond and is absent or present;

β is a bond and is absent or present; and

χ is a bond and is absent or present, wherein when α is absent, β is present, χ is absent, X is NH and $R_1$ is absent, and wherein when α is present, β is absent, χ is present, X is N and $R_1$ is present, or a pharmaceutically acceptable salt or ester thereof.

The present invention also provides a pharmaceutical composition comprising a pharmaceutical acceptable carrier and a compound having the structure:

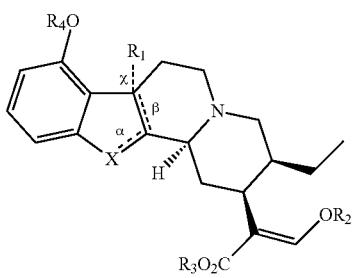

wherein
X is N or NH;
R₁ is —OH, —O-alkyl, —O(CO)-alkyl or is absent;
R$_2$ is —H or -alkyl;
R$_3$ is —H or -alkyl;
R$_4$ is —H or -alkyl;
α is a bond and is absent or present;
β is a bond and is absent or present; and
χ is a bond and is absent or present,
  wherein when α is absent, β is present, χ is absent, X is NH and R$_1$ is absent, and
  wherein when α is present, β is absent, χ is present, X is N and R$_1$ is present,
or a pharmaceutically acceptable salt or ester thereof, wherein the pharmaceutical composition is enriched in the compound that contains deuterium in place of —H.

The present invention also provides a pharmaceutical composition comprising a pharmaceutically acceptable carrier and a compound having the structure:

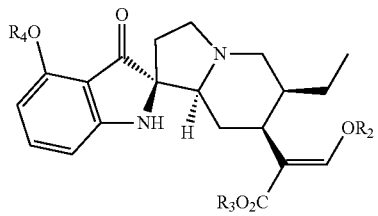

wherein
R$_2$ is —H or -alkyl;
R$_3$ is —H or -alkyl;
R$_4$ is —H or -alkyl,
or a pharmaceutically acceptable salt or ester thereof, wherein the pharmaceutical composition is enriched in the compound that contains deuterium in place of —H.

The present invention further provides a process for producing the compound having the structure:

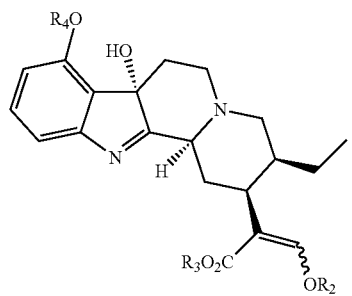

wherein
R$_2$ is —H or -alkyl;
R$_3$ is —H or -alkyl; and
R$_4$ is —H or -alkyl,
comprising irradiating a solution of the compound having the structure:

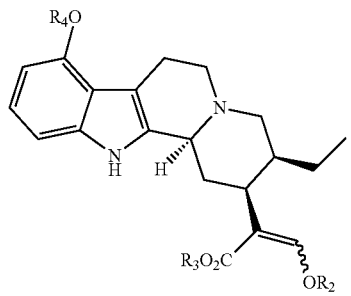

with light while subjected to atmospheric oxygen or a pure oxygen atmosphere under conditions sufficient to produce the compound.

The present invention still further provides process for producing the compound having the structure:

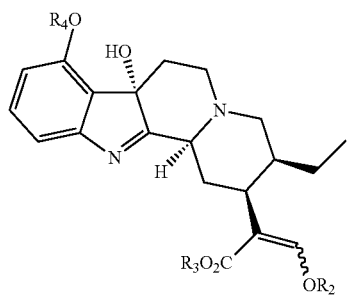

wherein
R$_2$ is —H or -alkyl;
R$_3$ is —H or -alkyl; and
R$_4$ is —H or -alkyl,
comprising reacting the compound having the structure:

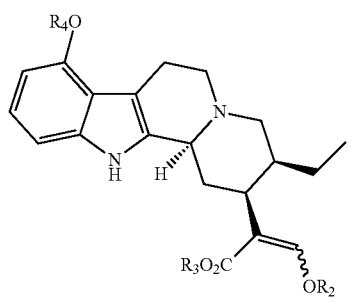

with potassium peroxymonosulfate under conditions sufficient to produce the compound.

The present invention further provides a method of treating a subject afflicted with a depressive disorder, an anxiety disorder or a mood disorder comprising administering an effective amount of the compound having the structure:

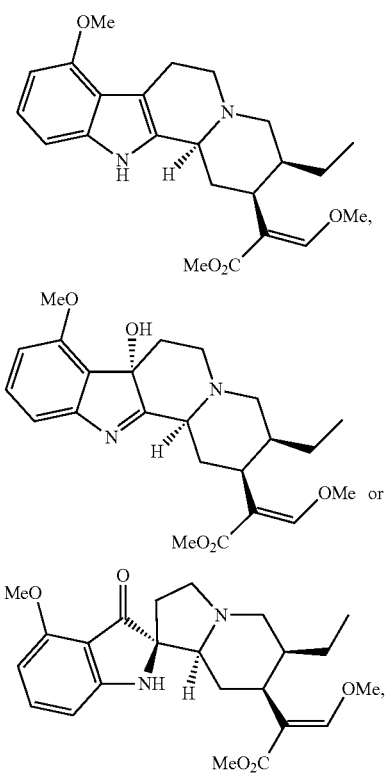

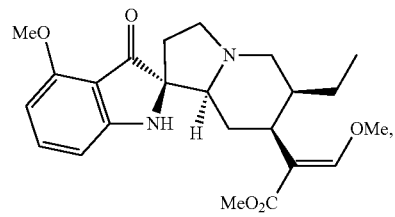

or a pharmaceutically acceptable salt or ester thereof, to the subject so as to thereby treat the subject afflicted with the depressive disorder, the anxiety disorder or the mood disorder The present invention yet further provides a method for systemic in vivo delivery of a first compound having the structure:

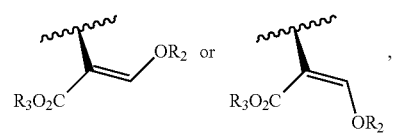

wherein

Y is

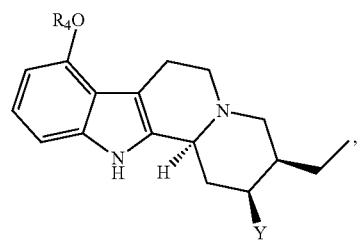

wherein

R$_2$ is —H, or -alkyl, and

R$_3$ is —H, or -alkyl; and

R$_4$ is —H, or -alkyl, to a subject, the method comprising administering to the subject a second compound having the structure:

or a pharmaceutically acceptable salt or ester thereof, to the subject so as to thereby treat the subject afflicted with the depressive disorder, the anxiety disorder or the mood disorder.

The present invention also provides a method of treating a subject afflicted with a depressive disorder, an anxiety disorder or a mood disorder comprising administering an effective amount of a pharmaceutical composition comprising a pharmaceutically acceptable carrier and the compound having the structure:

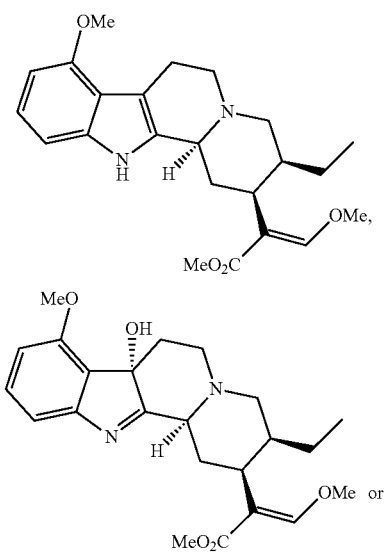

wherein
Y is

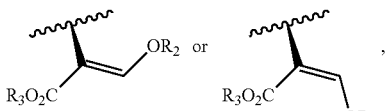

wherein
R₂ is —H, or -alkyl, and
R₃ is —H, or -alkyl; and
R₄ is —H, or -alkyl,
so as to thereby deliver the first compound to the subject.

DETAILED DESCRIPTION OF THE INVENTION

Figure 1:
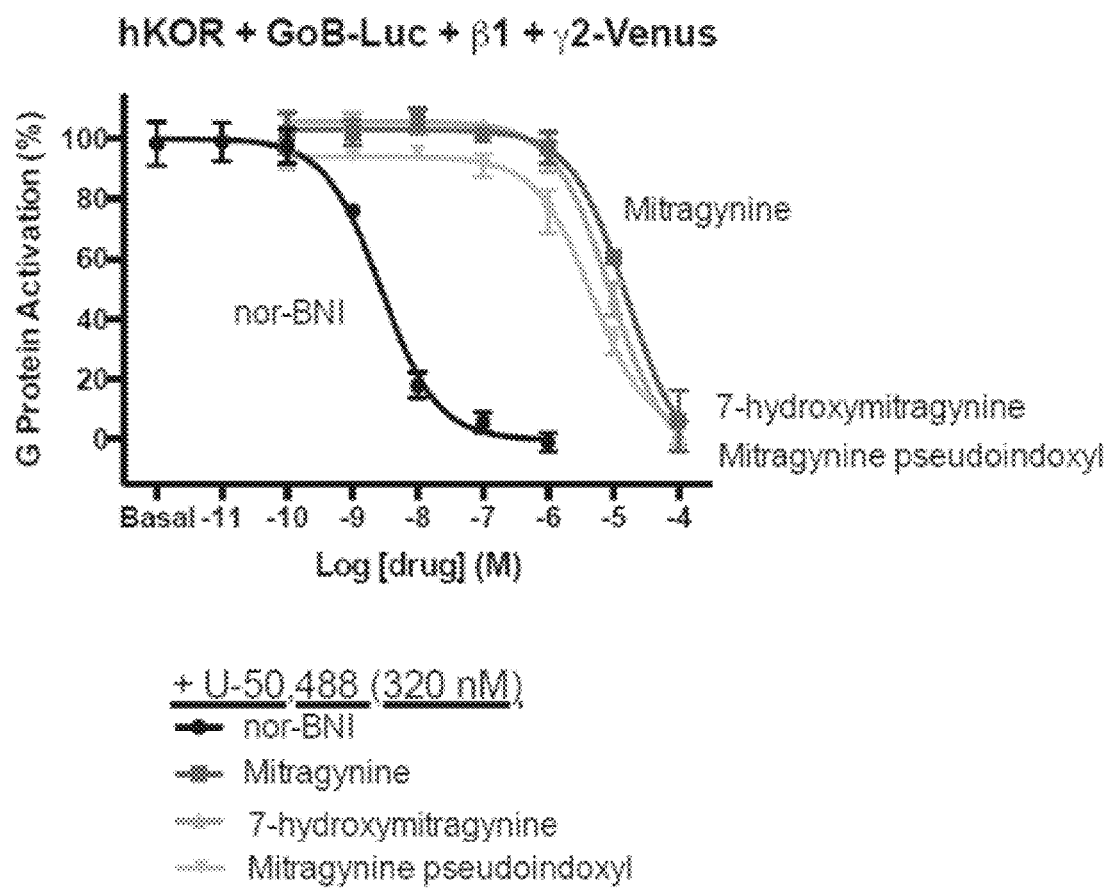
FIG. 1: Mitragynine, 7-hydroxymitragynine, and mitragynine pseudoindoxyl fully inhibit the agonist activity of U-50,488 (concentration of agonist=320 nM) at human KOR; positive control=nor-BNI.

The present invention provides a compound having the structure:

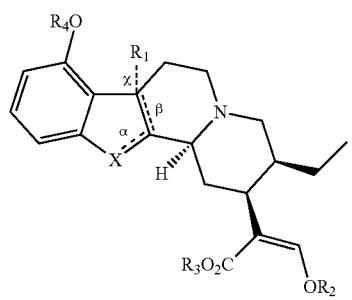

wherein
X is N or NH;
R₁ is —OH, —O-alkyl, —O(CO)-alkyl or is absent;
R₂ is —H or -alkyl;
R₃ is —H or -alkyl;
R₄ is —H or -alkyl;
α is a bond and is absent or present;
β is a bond and is absent or present; and
χ is a bond and is absent or present,
wherein when α is absent, β is present, χ is absent, X is NH and R₁ is absent, and wherein when α is present, β is absent, χ is present, X is N and R₁ is present,
or a pharmaceutically acceptable salt or ester thereof.

In some embodiments, the compound wherein R₂, R₃ and R₄ are each methyl.

In some embodiments, the compound wherein R₄ is methyl.

In some embodiments, the compound having the structure:

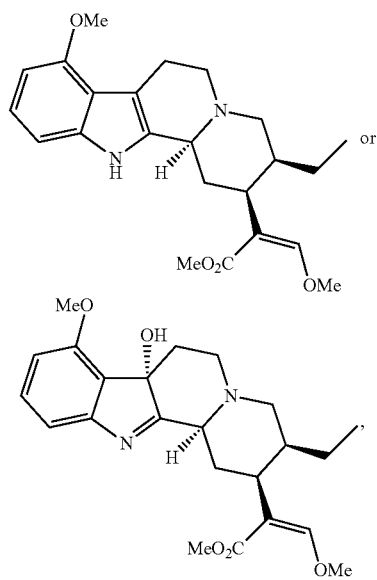

or a pharmaceutically acceptable salt or ester thereof.

In some embodiments, the compound wherein the compound is deuterium enriched.

In some embodiments, the compound wherein the compound is deuterium enriched at the R₂, R₃ and R₄ positions.

In some embodiments, the compound wherein the compound is deuterium enriched at the R₄ position.

In some embodiments, the compound having the structure:

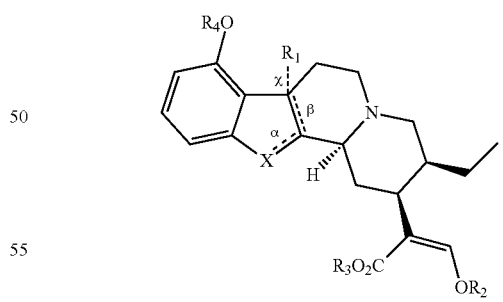

wherein
X is N or NH;
R₁ is —OH, —O-alkyl, —O(CO)-alkyl or is absent;
R₂ is -alkyl;
R₃ is -alkyl;
R₄ is -alkyl;
α is a bond and is absent or present;
β is a bond and is absent or present; and
χ is a bond and is absent or present, wherein when α is absent, β is present, χ is absent, X is NH and R₁ is absent, and wherein when α is present, β is absent, χ is present, X is N and R₁ is present, or a pharmaceutically acceptable salt or ester thereof.

In some embodiments, the compound having the structure:

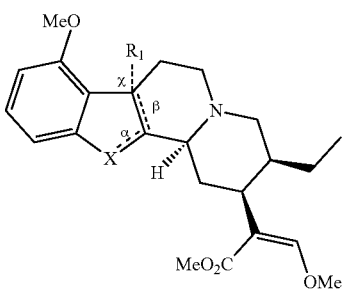

wherein
X is N or NH;
R₁ is —OH or —O-alkyl or is absent;
α is a bond and is absent or present;
β is a bond and is absent or present; and
χ is a bond and is absent or present,
  wherein when α is absent, β is present, χ is absent, X is NH and R₁ is absent, and
  wherein when α is present, β is absent, χ is present, X is N and R₁ is present,
or a pharmaceutically acceptable salt or ester thereof.

In some embodiments, the compound having the structure:

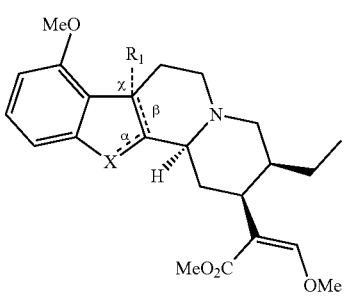

wherein
X is N;
R₁ is —OH or —O-alkyl and is present;
α is a bond and is present;
β is a bond and is absent; and
χ is a bond and present,
or a pharmaceutically acceptable salt or ester thereof.

In some embodiments, the compound having the structure:

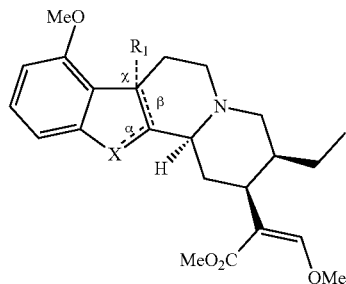

wherein
X is NH;
R₁ is absent;
α is a bond and is absent;
β is a bond and is present; and
χ is a bond and is absent,
or a pharmaceutically acceptable salt or ester thereof.

In some embodiments, the compound having the structure:

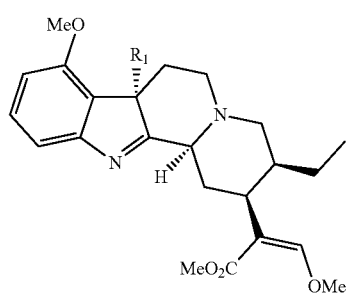

wherein
R₁ is —OH or —O-alkyl,
or a pharmaceutically acceptable salt or ester thereof.

In some embodiments, the compound having the structure:

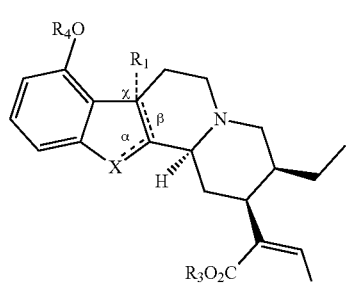

wherein
X is N or NH;
R₁ is —OH, —O(CO)-alkyl or is absent;
R₂ is -alkyl;
R₃ is -alkyl;
R₄ is -alkyl;
α is a bond and is absent or present;
β is a bond and is absent or present; and
χ is a bond and is absent or present,
  wherein when α is absent, β is present, χ is absent, X is NH and R₁ is absent, and wherein when α is present, β is absent, χ is present, X is N and P is present, or a pharmaceutically acceptable salt or ester thereof.

In some embodiments, the compound having the structure:

[Chemical structure]

wherein

X is N or NH;

R₁ is —OH, —O(CO)-alkyl or is absent;

α is a bond and is absent or present;

β is a bond and is absent or present; and

χ is a bond and is absent or present, wherein when α is absent, β is present, χ is absent, X is NH and R₁ is absent, and wherein when α is present, β is absent, χ is present, X is N and R₁ is present, or a pharmaceutically acceptable salt or ester thereof.

In some embodiments, the compound having the structure:

[Chemical structure]

wherein

X is N;

R₁ is —OH or —O(CO)-alkyl and is present;

α is a bond and is present;

β is a bond and is absent; and

χ is a bond and present, or a pharmaceutically acceptable salt or ester thereof.

In some embodiments, the compound having the structure:

[Chemical structure]

wherein

R₁ is —OH or —O(CO)-alkyl, or a pharmaceutically acceptable salt or ester thereof.

In one embodiment, R₁ is O—($C_{1-5}$ alkyl). In one embodiment, R₁ is O—($C_{1-10}$ alkyl). In one embodiment, R₁ is O—($C_1$ alkyl). In one embodiment, R₁ is —OH.

In one embodiment, R₁ is —O(CO)—($C_{1-5}$ alkyl). In one embodiment, R₁ is —O(CO)—($C_{1-10}$ alkyl).

In one embodiment, R₂ is ($C_{1-5}$ alkyl). In one embodiment, R₂ is ($C_{1-10}$ alkyl). In one embodiment, R₂ is ($C_1$ alkyl).

In one embodiment, R₃ is ($C_{1-5}$ alkyl). In one embodiment, R₃ is ($C_{1-10}$ alkyl). In one embodiment, R₃ is ($C_1$ alkyl).

In one embodiment, R₄ is ($C_{1-5}$ alkyl). In one embodiment, R₄ is ($C_{1-10}$ alkyl). In one embodiment, R₄ is ($C_1$ alkyl).

In some embodiments, the pharmaceutical composition comprising the compound of the present invention and a pharmaceutically acceptable carrier.

In some embodiments, the composition wherein the compound has the structure:

[Chemical structure] or

[Chemical structure]

or a pharmaceutically acceptable salt or ester thereof.

In some embodiments, wherein the pharmaceutical composition is enriched in the compound that contains deuterium in place of —H.

In some embodiments, the composition wherein the isotopic purity at each position of the R₂ methyl group is 95% or greater in deuterium; the isotopic purity at each position of the $R_3$ methyl group is 95% or greater in deuterium; and the isotopic purity at each position of the $R_4$ methyl group is 95% or greater in deuterium.

In some embodiments, the composition wherein the isotopic purity at each position of the $R_4$ methyl group is 95% or greater in deuterium. The present invention also provides a pharmaceutical composition comprising a pharmaceutical acceptable carrier and a compound having the structure:

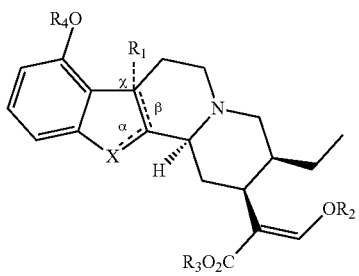

wherein

X is N or NH;

$R_1$ is —OH, —O-alkyl, —O(CO)-alkyl or is absent;

$R_2$ is —H or -alkyl;

$R_3$ is —H or -alkyl;

$R_4$ is —H or -alkyl;

α is a bond and is absent or present;

β is a bond and is absent or present; and

χ is a bond and is absent or present, wherein when α is absent, β is present, χ is absent, X is NH and $R_1$ is absent, and wherein when α is present, β is absent, χ is present, X is N and $R_1$ is present, or a pharmaceutically acceptable salt or ester thereof, wherein the pharmaceutical composition is enriched in the compound that contains deuterium in place of —H.

In some embodiments, the composition wherein in the compound $R_2$, $R_3$ and $R_4$ are each methyl.

In some embodiments, the composition wherein in the compound $R_4$ is methyl.

In some embodiments, the composition wherein the deuterated compound contains deuterium at the $R_2$, $R_3$ and $R_4$ positions.

In some embodiments, the composition wherein the deuterated compound contains deuterium at the $R_4$ position.

In some embodiments, the composition wherein the isotopic purity at each position of the $R_2$ methyl group is 95% or greater in deuterium; the isotopic purity at each position of the $R_3$ methyl group is 95% or greater in deuterium; and the isotopic purity at each position of the $R_4$ methyl group is 95% or greater in deuterium.

In some embodiments, the composition wherein the isotopic purity at each position of the $R_4$ methyl group is 95% or greater in deuterium.

In some embodiments, the composition wherein the deuterated compound has the structure:

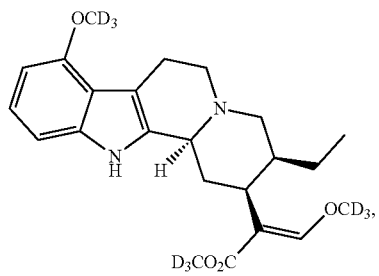

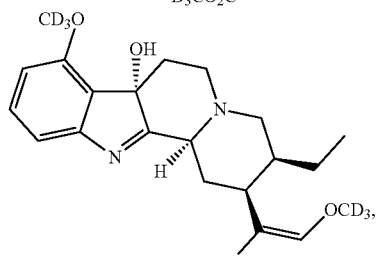

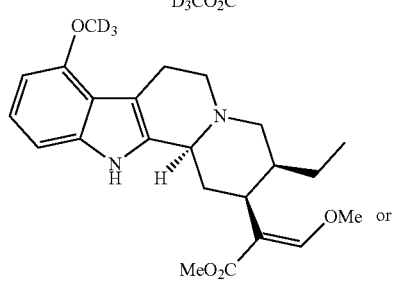

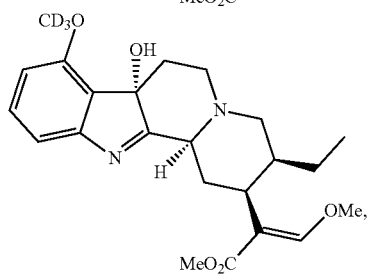

or a pharmaceutically acceptable salt or ester thereof.

The present invention also provides a pharmaceutical composition comprising a pharmaceutically acceptable carrier and a compound having the structure:

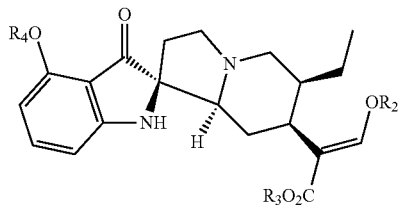

wherein $R_2$ is —H or -alkyl;

$R_3$ is —H or -alkyl;

$R_4$ is —H or -alkyl, or a pharmaceutically acceptable salt or ester thereof, wherein the pharmaceutical composition is enriched in the compound that contains deuterium in place of —H.

In some embodiments, the composition wherein in the compound $R_2$, $R_3$ and $R_4$ are each methyl.

In some embodiments, the composition wherein in the compound R₄ is methyl.

In some embodiments, the composition wherein the deuterated compound contains deuterium at the R₂, R₃ and R₄ positions.

In some embodiments, the composition wherein the deuterated compound contains deuterium at the R₄ position.

In some embodiments, the composition wherein the isotopic purity at each position of the R₂ methyl group is 95% or greater in deuterium; the isotopic purity at each position of the R₃ methyl group is 95% or greater in deuterium; and the isotopic purity at each position of the R₄ methyl group is 95% or greater in deuterium.

In some embodiments, the composition wherein the isotopic purity at each position of the R₄ methyl group is 95% or greater in deuterium.

In some embodiments, the composition wherein the deuterated compound has the structure:

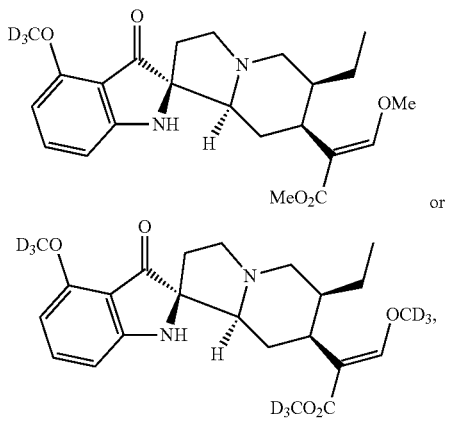

or a pharmaceutically acceptable salt or ester thereof.

In some embodiments, a method of activating a mu-opioid receptor comprising contacting the mu-opioid receptor with the compound or composition of the present invention.

In some embodiments, a method of antagonizing a delta-opioid receptor and/or a kappa-opioid receptor comprising contacting the delta-opioid receptor and/or the kappa-opioid receptor with the compound or composition of the present invention.

In some embodiments, a method of treating a subject afflicted with pain comprising administering an effective amount of the compound or composition of the present invention to the subject so as to thereby treat the subject afflicted with pain.

In some embodiments, a method of treating a subject afflicted with a depressive disorder comprising administering an effective amount of the compound or composition of the present invention to the subject so as to thereby treat the subject afflicted with the depressive disorder.

In some embodiments, a method of treating a subject afflicted with a mood disorder or an anxiety disorder comprising administering an effective amount of the compound or composition of the present invention to the subject so as to thereby treat the subject afflicted with the mood disorder or anxiety disorder.

In some embodiments, a method of treating a subject afflicted with a pain comprising administering to the subject an effective amount of an NMDA receptor antagonist, an NMDA receptor partial agonist, a neurokinin 1 receptor antagonist or a delta-opioid receptor agonist and an effective amount of the compound or composition of the present invention so as to thereby treat the subject afflicted with pain.

In some embodiments, a method of treating a subject afflicted with a depressive disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist or a delta-opioid receptor agonist and an effective amount of the compound or composition of the present invention so as to thereby treat the subject afflicted with the depressive disorder.

In some embodiments, a method of treating a subject afflicted with a mood disorder or an anxiety disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist or a delta-opioid receptor agonist and an effective amount of the compound or composition of the present invention so as to thereby treat the subject afflicted with the mood disorder or anxiety disorder.

The present invention also provides a process for producing the compound having the structure:

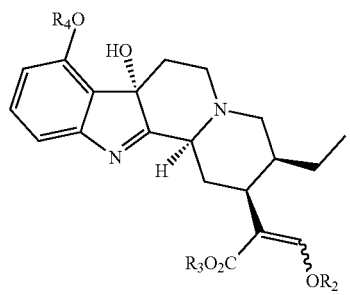

wherein
R₂ is —H or -alkyl;
R₃ is —H or -alkyl; and
R₄ is —H or -alkyl,
comprising irradiating a solution of the compound having the structure:

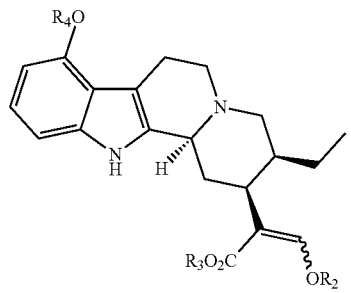

with light while subjected to atmospheric oxygen or a pure oxygen atmosphere under conditions sufficient to produce the compound.

In some embodiments, the process comprising
(a) dissolving the compound having the structure:

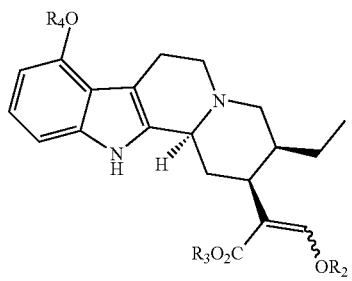

in a suitable solvent and adding to the solution a photosensitizer;

(b) irradiating the solution with light while subjected to atmospheric oxygen or a pure oxygen atmosphere to produce a compound having the structure:

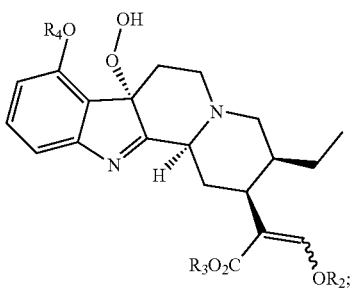

(c) discontinuing irradiation and stirring the solution in the presence of a reducing agent to thereby produce the compound.

In some embodiments, the process comprising
(a) dissolving the compound having the structure:

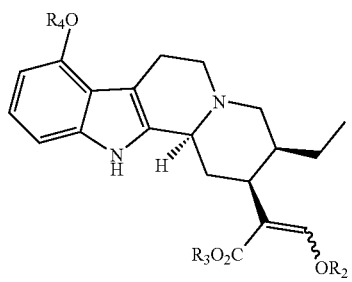

in a suitable solvent and adding to the solution a photosensitizer;
(b) cooling the solution to between −5 and 5° C.;
(c) irradiating the solution with light while subjected to atmospheric oxygen or a pure oxygen atmosphere to produce a compound having the structure:

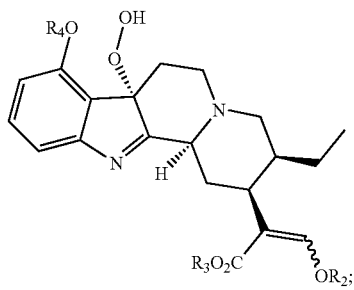

(d) discontinuing irradiation and stirring the solution at between 15 and 25° C. in the presence of a reducing agent to thereby produce the compound.

The present invention also provides a process for producing the compound having the structure:

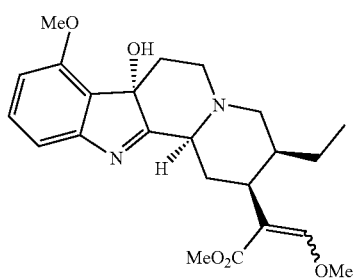 [SMILES: CC[C@@H]1CN2CC[C@@]3(O)C(=Nc4cccc(OC)c43)[C@@H]2C[C@@H]1C(=COC)C(=O)OC]

comprising irradiating a solution of the compound having the structure:

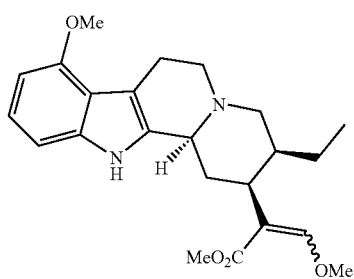 [SMILES: CC[C@@H]1CN2CCc3c([nH]c4cccc(OC)c34)[C@@H]2C[C@@H]1C(=COC)C(=O)OC]

with light while subjected to atmospheric oxygen or a pure oxygen atmosphere under conditions sufficient to produce the compound.

In some embodiments, the process comprising
(a) dissolving the compound having the structure:

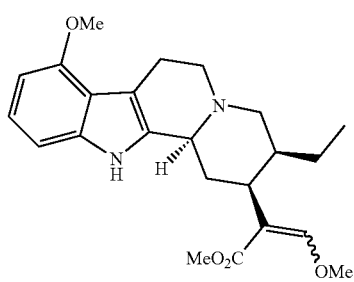 [SMILES: CC[C@@H]1CN2CCc3c([nH]c4cccc(OC)c34)[C@@H]2C[C@@H]1C(=COC)C(=O)OC]

in a suitable solvent and adding to the solution a photosensitizer;

(b) irradiating the solution with light while subjected to atmospheric oxygen or a pure oxygen atmosphere to produce a compound having the structure:

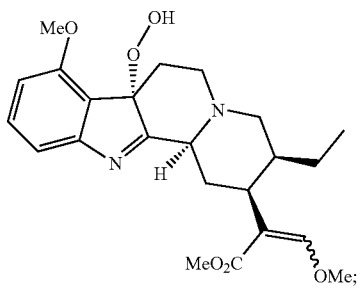 [SMILES: CC[C@@H]1CN2CC[C@@]3(OO)C(=Nc4cccc(OC)c43)[C@@H]2C[C@@H]1C(=COC)C(=O)OC]

(c) discontinuing irradiation and stirring the solution in the presence of a reducing agent to thereby produce the compound.

In some embodiments, the process comprising
(a) dissolving the compound having the structure:

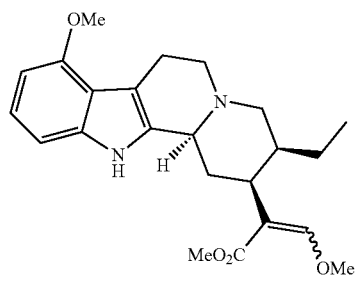 [SMILES: CC[C@@H]1CN2CCc3c([nH]c4cccc(OC)c34)[C@@H]2C[C@@H]1C(=COC)C(=O)OC]

in a suitable solvent and adding to the solution a photosensitizer;
(b) cooling the solution to between −5 and 5° C.;
(c) irradiating the solution with light while subjected to atmospheric oxygen or a pure oxygen atmosphere to produce a compound having the structure:

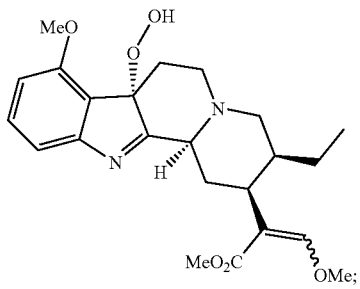 [SMILES: CC[C@@H]1CN2CC[C@@]3(OO)C(=Nc4cccc(OC)c43)[C@@H]2C[C@@H]1C(=COC)C(=O)OC]

(d) discontinuing irradiation and stirring the solution at between 15 and 25° C. in the presence of a reducing agent to thereby produce the compound.

In some embodiments, the process wherein the light is produced by a halogen lamp.

In some embodiments, the process wherein the light is produced by light-emitting diodes.

In some embodiments, the process wherein the photosensitizer is rose bengal.

In some embodiments, the process wherein the photosensitizer is rose bengal sodium salt.

In some embodiments, the process wherein the suitable solvent is methanol.

In some embodiments, the process wherein in step (b), the solution is cooled to 0° C.

In some embodiments, the process wherein the reducing agent is sodium sulfite or sodium metabisulfite.

In some embodiments, the process wherein the compound produced has the structure:

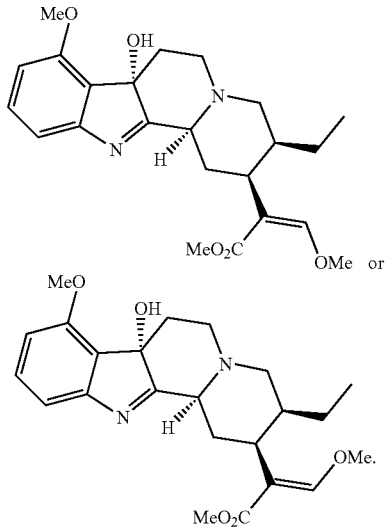

The present invention still further provides process for producing the compound having the structure:

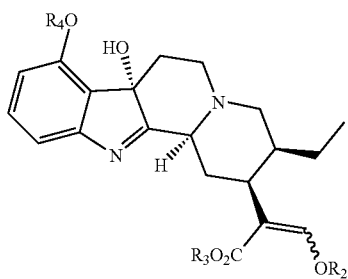

wherein
$R_2$ is —H or -alkyl;
$R_3$ is —H or -alkyl; and
$R_4$ is —H or -alkyl,
comprising reacting the compound having the structure:

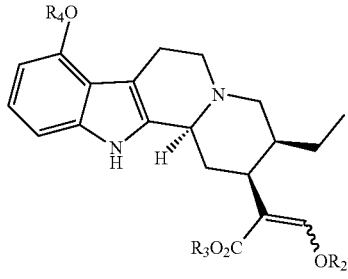

with potassium peroxymonosulfate under conditions sufficient to produce the compound.

In some embodiments, the process wherein the reaction occurs in the presence of a base.

In some embodiments, the process wherein the base is sodium bicarbonate.

In some embodiments, the process wherein the reaction is performed in a suitable solvent.

In some embodiments, the process wherein the suitable solvent is acetone.

In some embodiments, the process wherein the compound produced has the structure:

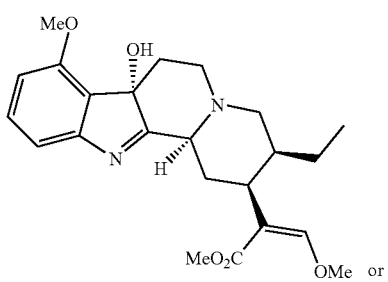

or

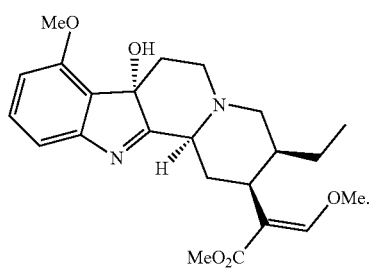

The present invention further provides a method of treating a subject afflicted with a depressive disorder, an anxiety disorder or a mood disorder comprising administering an effective amount of the compound having the structure:

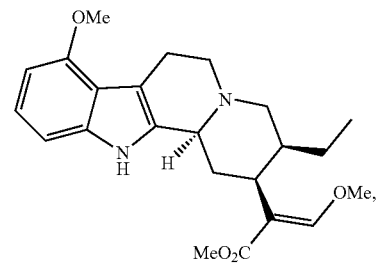

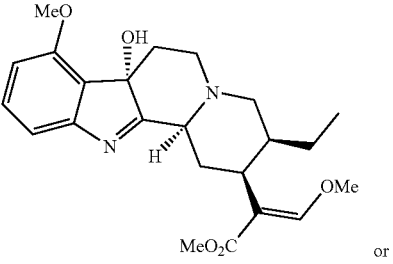

or

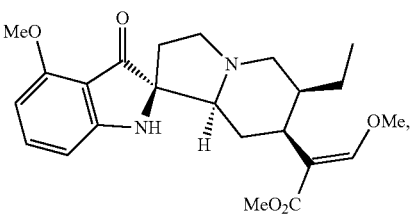

or a pharmaceutically acceptable salt or ester thereof, to the subject so as to thereby treat the subject afflicted with the depressive disorder, the anxiety disorder or the mood disorder.

In some embodiments of the above method, the method wherein the compound is deuterium enriched.

In some embodiments of the above method, wherein the compound activates mu-opioid receptors in the subject.

In some embodiments of the above method, wherein the compound antagonizes delta-opioid receptors and/or the kappa-opioid receptors in the subject.

In some embodiments of the above method, wherein the compound antagonizes delta-opioids receptors and/or the kappa-opioids receptors and activates mu-opioid receptors in the subject.

In some embodiments of the above method, wherein the subject is afflicted with a depressive disorder.

In some embodiments of the above method, wherein the subject is afflicted with a mood disorder.

In some embodiments of the above method, wherein the subject is afflicted with an anxiety disorder.

In some embodiments of the above method, the method further comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist or a DOR agonist.

In some embodiments of the above method, the method further comprising administering to the subject an effective amount of an NMDA receptor antagonist, an NMDA receptor partial agonist, a neurokinin 1 receptor antagonist or a DOR agonist.

The present invention also provides a method of treating a subject afflicted with a depressive disorder, an anxiety disorder or a mood disorder comprising administering an effective amount of a pharmaceutical composition comprising a pharmaceutically acceptable carrier and the compound having the structure:

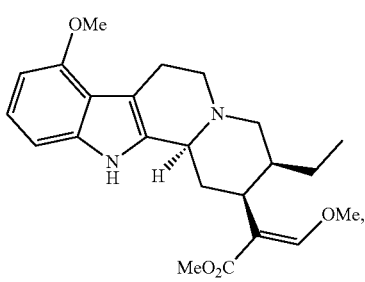

-continued

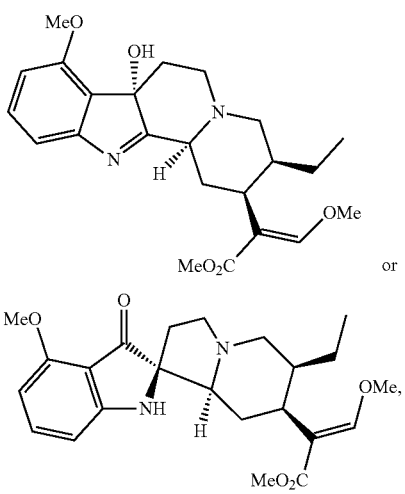

or a pharmaceutically acceptable salt or ester thereof, to the subject so as to thereby treat the subject afflicted with the depressive disorder, the anxiety disorder or the mood disorder.

In some embodiments of the above method, the method wherein the compound is deuterium enriched.

In some embodiments, a process for producing the compound having the structure:

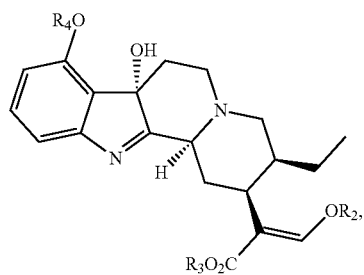

wherein $R_2$, $R_3$ and $R_4$ are each alkyl,
comprising irradiating a solution of the compound having the structure:

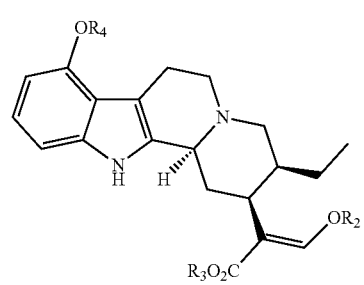

with light while subjected to atmospheric oxygen or a pure oxygen atmosphere under conditions sufficient to produce the compound.

In some embodiments, a process for producing the compound having the structure:

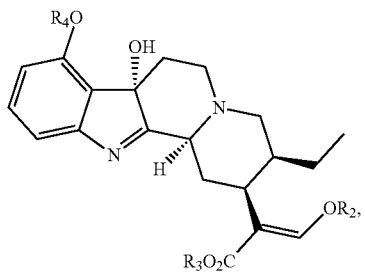

wherein $R_2$, $R_3$ and $R_4$ are each alkyl,
comprising
(a) dissolving the compound having the structure:

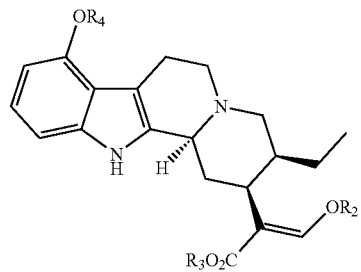

in a suitable solvent and adding to the solution a photosensitizer;
(b) irradiating the solution with light while subjected to atmospheric oxygen or a pure oxygen atmosphere to produce a compound having the structure:

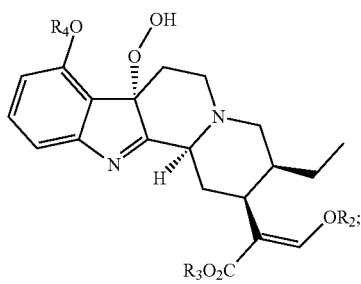

(c) discontinuing irradiation and stirring the solution in the presence of a reducing agent to thereby produce the compound.

In some embodiments, a process for producing the compound having the structure:

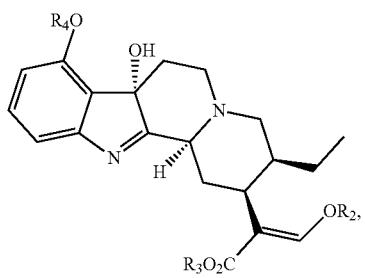

wherein $R_2$, $R_3$ and $R_4$ are each alkyl, comprising (a) dissolving the compound having the structure:

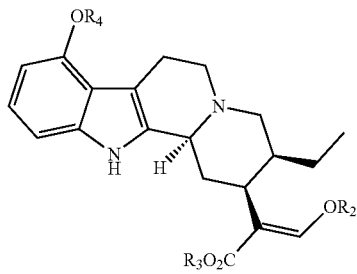

in a suitable solvent and adding to the solution a photosensitizer;

(b) cooling the solution to between −5 and 5° C.;

(c) irradiating the solution with light while subjected to atmospheric oxygen or a pure oxygen atmosphere to produce a compound having the structure:

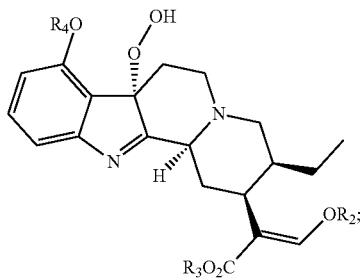

(d) discontinuing irradiation and stirring the solution at between 15 and 25° C. in the presence of a reducing agent to thereby produce the compound.

In some embodiments, a process for producing the compound having the structure:

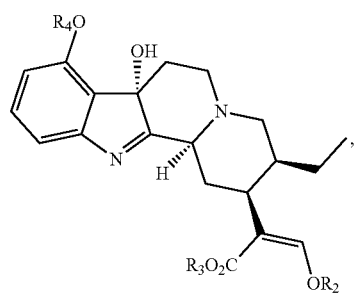

wherein $R_2$, $R_3$ and $R_4$ are each alkyl, comprising irradiating a solution of the compound having the structure:

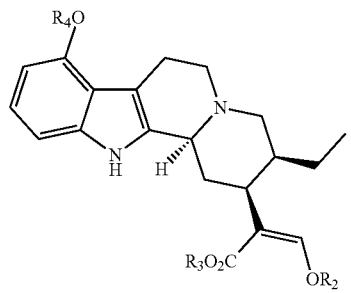

with light while subjected to atmospheric oxygen or a pure oxygen atmosphere under conditions sufficient to produce the compound.

In some embodiments, a process for producing the compound having the structure:

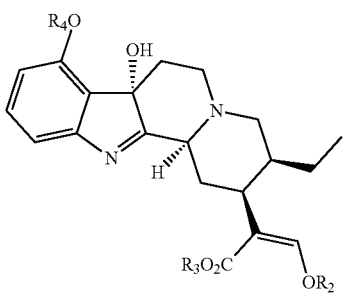

wherein $R_2$, $R_3$ and $R_4$ are each alkyl,
comprising
(a) dissolving the compound having the structure:

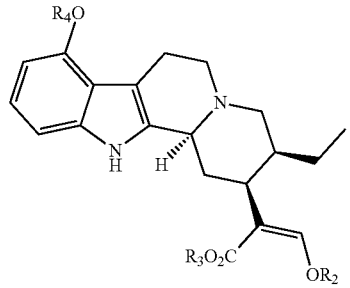

in a suitable solvent and adding to the solution a photosensitizer;

(b) irradiating the solution with light while subjected to atmospheric oxygen or a pure oxygen atmosphere to produce a compound having the structure:

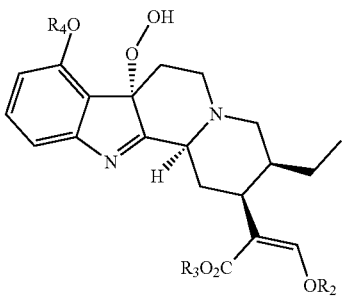

(c) discontinuing irradiation and stirring the solution in the presence of a reducing agent to thereby produce the compound.

In some embodiments, a process for producing the compound having the structure:

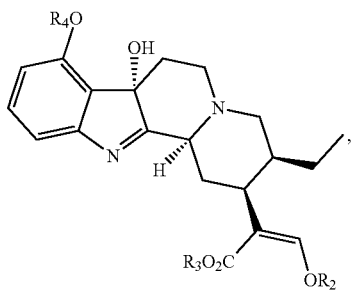

wherein $R_2$, $R_3$ and $R_4$ are each alkyl,
comprising
(a) dissolving the compound having the structure:

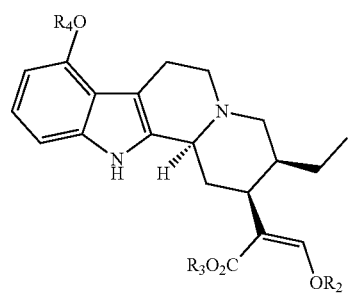

in a suitable solvent and adding to the solution a photosensitizer;
(b) cooling the solution to between −5 and 5° C.;
(c) irradiating the solution with light while subjected to atmospheric oxygen or a pure oxygen atmosphere to produce a compound having the structure:

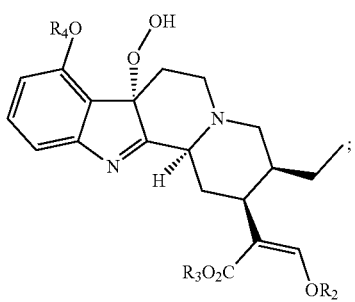

(d) discontinuing irradiation and stirring the solution at between 15 and 25° C. in the presence of a reducing agent to thereby produce the compound.

In some embodiments, a pharmaceutical composition comprising the compound of the present invention and a pharmaceutically acceptable carrier.

In some embodiments, a method of activating a mu-opioid receptor comprising contacting the mu-opioid receptor with the compound of the present invention.

In some embodiments, a method of antagonizing a kappa-opioid receptor comprising contacting the kappa-opioid receptor with the compound of the present invention.

In some embodiments, the mu-opioid receptors are in a human subject.

In some embodiments, the delta-opioid receptors are in a human subject.

In some embodiments, the kappa-opioid receptors are in a human subject.

In some embodiments, a method of treating a subject afflicted with pain, a depressive disorder, an anxiety disorder or a mood disorder comprising administering an effective amount of the compound of the present invention to the subject so as to treat the subject afflicted with pain, the depressive disorder, the anxiety disorder or the mood disorder.

In some embodiments, a method of treating a subject afflicted with pain, a depressive disorder, an anxiety disorder or a mood disorder comprising administering to the subject an effective amount of a NMDA receptor antagonist, an NMDA receptor partial agonist, a neurokinin 1 receptor antagonist, a neurokinin 2 receptor antagonist, a neurokinin 3 receptor antagonist or a DOR agonist and an effective amount of the compound of the present invention so as to thereby treat the subject afflicted with pain, the depressive disorder, the anxiety disorder or the mood disorder.

The present invention yet further provides a method for systemic in vivo delivery of a first compound having the structure:

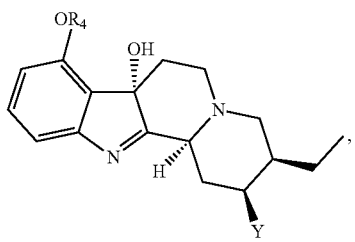

wherein
Y is

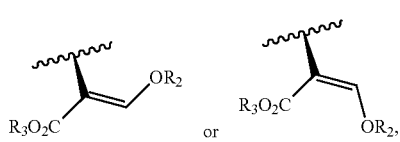

wherein
$R_2$ is —H, or -alkyl, and
$R_3$ is —H, or -alkyl; and
$R_4$ is —H, or -alkyl,
to a subject, the method comprising administering to the subject a second compound having the structure:

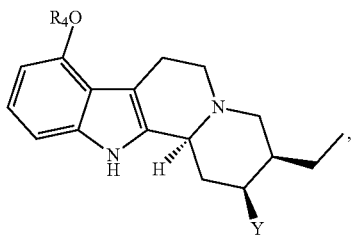

wherein
Y is

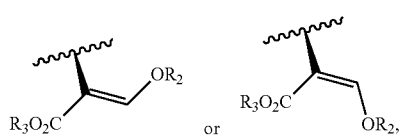

wherein
R₂ is —H, or -alkyl, and
R₃ is —H, or -alkyl; and
R₄ is —H, or -alkyl,
so as to thereby deliver the first compound to the subject.

In some embodiments, the method wherein in the first and second compound, when Y is

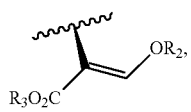

wherein R₂ and R₃ are each methyl, then R₄ is other than methyl.

In some embodiments, the method wherein the subject is afflicted with pain, a depressive disorder, a mood disorder, or an anxiety disorder.

In some embodiments, the method wherein administration of the second compound is effective to treat the subject afflicted with the pain, depressive disorder, mood disorder, or anxiety disorder.

In some embodiments, the method wherein the second compound is orally administered to the subject.

In some embodiments, the method wherein 10-30 mg of the second compound is administered to the subject. In some embodiments, the method wherein 30-100 mg of the second compound is administered to the subject. In some embodiments, the method wherein 100-200 mg of the second compound is administered to the subject.

In some embodiments, the method wherein the compound is deuterium enriched.

In some embodiments, the method wherein R₂, R₃ and R₄ are each methyl.

In some embodiments, the method wherein R₄ is methyl.

In some embodiments, the method wherein R₂ and R₃ are each —H and R₄ is methyl.

In some embodiments, the method wherein the compound is deuterium enriched at the R₂, R₃ and R₄ positions.

In some embodiments, the method wherein the compound is deuterium enriched at the R₄ position.

In some embodiments, the method wherein the second compound has the structure:

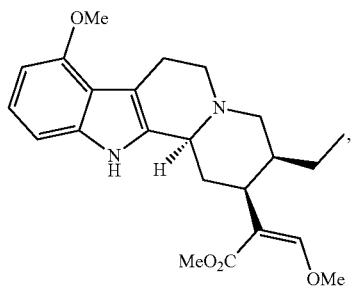

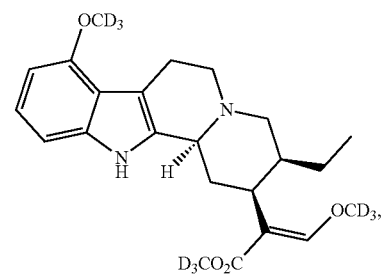

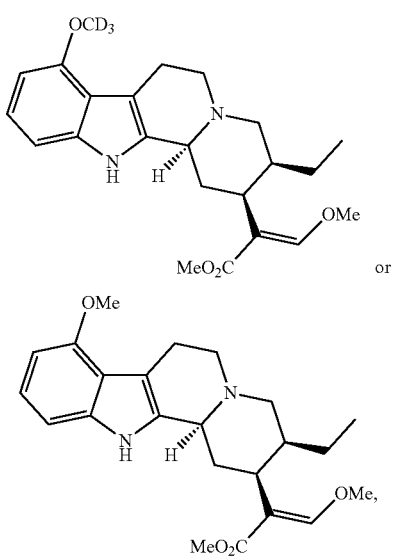

or a pharmaceutically acceptable salt or ester thereof.

In some embodiments, the method wherein the first compound has the structure:

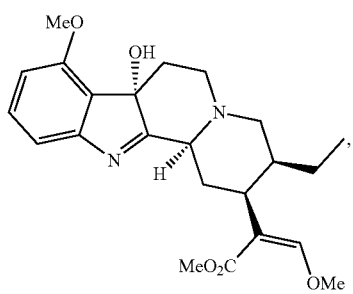

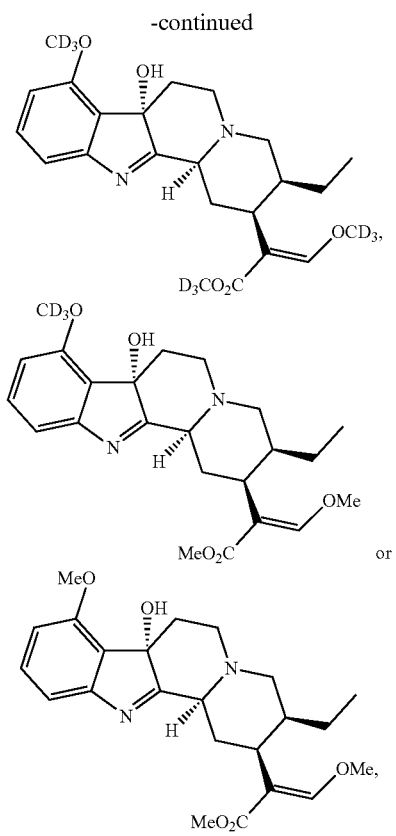

or a pharmaceutically acceptable salt or ester thereof.

In some embodiments, the anxiety disorder includes, but is not limited to, is anxiety, generalized anxiety disorder (GAD), panic disorder, social phobia, social anxiety disorder, acute stress disorder, obsessive-compulsive disorder (OCD), or post-traumatic stress disorder (PTSD).

In some embodiments, the depressive disorder includes, but is not limited to, depression, major depression, dysthymia, cyclothymia, postpartum depression, seasonal affective disorder, atypical depression, psychotic depression, bipolar disorder, premenstrual dysphoric disorder, situational depression or adjustment disorder with depressed mood. Depressive disorders can also include other mood disorders and is not limited to the above list.

In some embodiments, the NMDA receptor antagonist is an arylcyclohexylamine, dextromorphinan or adamantane.

In some embodiments, the NMDA receptor antagonist is dextromethorphan, dextrorphan, dextrallorphan, memantine, amantadine, rimantadine, nitromemantine (YQW-36), ketamine (and its analogs, e.g. tiletamine), phencyclidine (and its analogs, e.g. tenocyclidine, eticyclidine, rolicyclidine), methoxetamine (and its analogs), gacyclidine (GK-11), neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A) or AP-7.

In some embodiments, the NMDA receptor partial agonist is NRX-1074 or rapastinel (GLYX-13).

In some embodiments, the neurokinin 1 receptor antagonist is aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888 or GR 82334.

In some embodiments, the neurokinin 2 receptor antagonist is saredutant, ibodutant, nepadutant, GR-159897 or MEN-10376.

In some embodiments, the neurokinin 3 receptor antagonist is osanetant, talnetant, SB-222200 or SB-218795.

In some embodiments, the DOR agonist is tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863 or 7-spiroindanyloxymorphone.

In some embodiments, the potassium peroxymonosulfate is OXONE®.

Potassium peroxymonosulfate is used as an oxidizing agent and is commercially available from DuPont under the trade name OXONE® as a component of a triple salt with the formula $KHSO_5 \cdot 0.5KHSO_4 \cdot 0.5K_2SO_4$. In some embodiments, the potassium peroxymonosulfate source is OXONE®.

In some embodiments, OXONE® refers to solution of $KHSO_5 \cdot 0.5KHSO_4 \cdot 0.5K$ SOS in water. The concentration of OXONE® may be, but is not limited to, about 10%, 20%, 30%, 40% or 50%.

The term "MOR agonist" is intended to mean any compound or substance that activates the mu-opioid receptor (MOR). The agonist may be a partial, full or super agonist.

The term "DO agonist" is intended to mean any compound or substance that activates the delta-opioid receptor (DOR). The agonist may be a partial, full or super agonist.

The term "KOR agonist" is intended to mean any compound or substance that activates the kappa-opioid receptor (KOR). The agonist may be a partial, full or super agonist.

The term "super agonist" is intended to mean a compound or substance that activates a receptor with a greater maximal response (higher $E_{max}$) than said receptor's primary endogenous ligand.

The term "MOR antagonist" is intended to mean any compound or substance that blocks or dampens activity of the mu-opioid receptor (MOP). In some instances, the MOR antagonist disrupts the interaction and inhibits the function of an agonist or inverse agonist at the MOR. The antagonist may be a competitive, non-competitive, uncompetitive, or silent antagonist.

The term "DOR antagonist" is intended to mean any compound or substance that blocks or dampens activity of the delta-opioid receptor (DOP). In some instances, the DOR antagonist disrupts the interaction and inhibits the function of an agonist or inverse agonist at the DOR. The antagonist may be a competitive, non-competitive, uncompetitive, or silent antagonist.

The term "KOR antagonist" is intended to mean any compound or substance that blocks or dampens activity of the kappa-opioid receptor (KOR). In some instances, the KOR antagonist disrupts the interaction and inhibits the function of an agonist or inverse agonist at the KOR. The antagonist may be a competitive, non-competitive, uncompetitive, or silent antagonist.

The present invention also provides a compound having the structure:

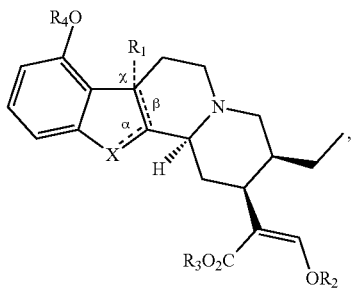

or a salt or ester thereof, for use in treating a subject afflicted with pain, a depressive disorder, an anxiety disorder or a mood disorder.

The present invention further provides a pharmaceutical composition comprising an amount of a compound having the structure:

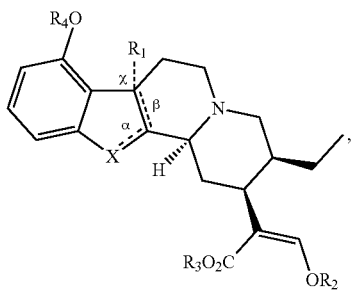

or a salt or ester thereof, for use in treating a subject afflicted with pain, a depressive disorder, an anxiety disorder or a mood disorder.

The present invention also provides a compound having the structure:

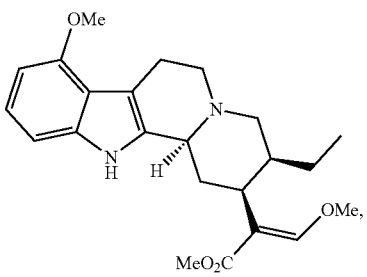

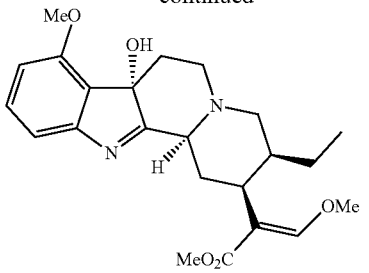

or

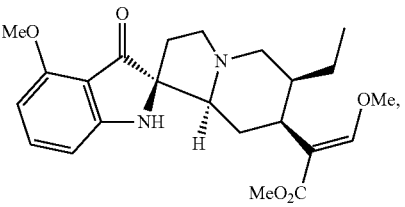

or a salt or ester thereof, for use in treating a subject afflicted with a depressive disorder, an anxiety disorder or a mood disorder.

The present invention further provides a pharmaceutical composition comprising an amount of a compound having the structure:

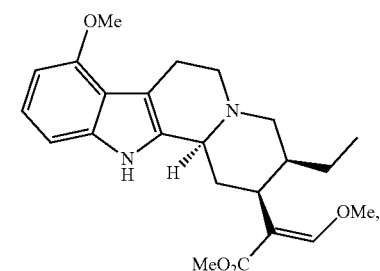

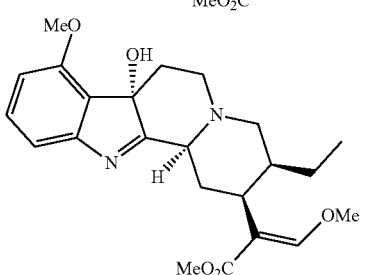

or

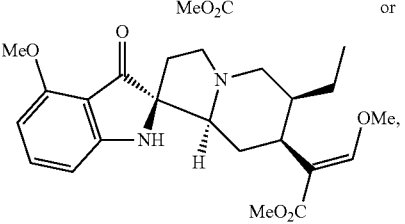

or a salt or ester thereof, for use in treating a subject afflicted with a depressive disorder, an anxiety disorder or a mood disorder.

The present invention also provides for the use of a compound having the structure:

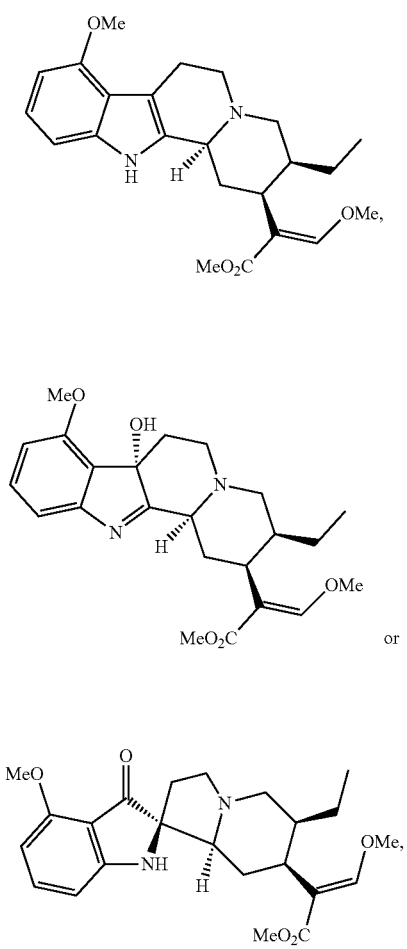

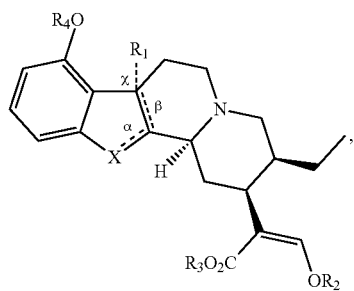

or a salt or ester thereof, for treating a depressive disorder, an anxiety disorder or a mood disorder.

The present invention also provides a compound having the structure:

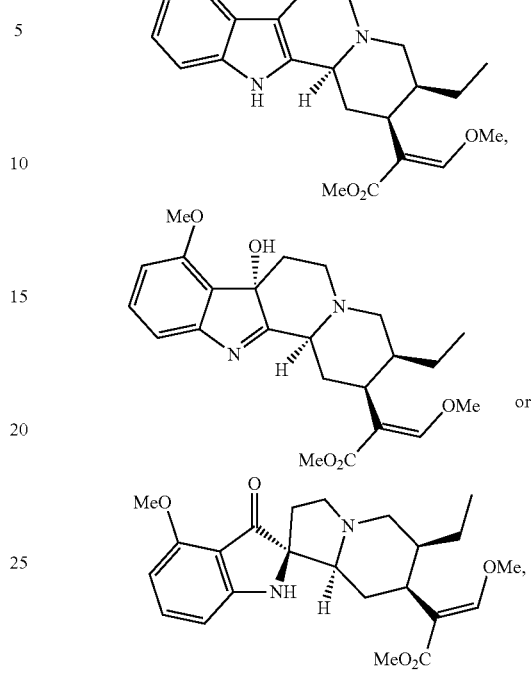

or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with pain, a depressive disorder, an anxiety disorder or a mood disorder.

The present invention also provides a compound having the structure:

or a salt or ester thereof, for use as an add-on therapy or in combination with an NMDA receptor antagonist, an NMDA receptor partial agonist, a neurokinin 1 receptor antagonist, a neurokinin 2 receptor antagonist, a neurokinin 3 receptor antagonist, or a DOR agonist in treating a subject afflicted with pain, a depressive disorder, an anxiety disorder or a mood disorder.

In some embodiments, a package comprising:
a) a first pharmaceutical composition comprising an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist and a pharmaceutically acceptable carrier;
b) a second pharmaceutical composition comprising an amount of any compound of the present invention, or a salt or ester thereof; and
c) instructions for use of the first and second pharmaceutical compositions together to treat a subject afflicted with pain, a depressive disorder, an anxiety disorder or a mood disorder.

In some embodiments, a therapeutic package for dispensing to, or for use in dispensing to, a subject afflicted with pain, a depressive disorder, an anxiety disorder or a mood disorder, which comprises:
a) one or more unit doses, each such unit dose comprising:
  (i) an amount of any compound of the present invention, or a salt or ester thereof; and
  (ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

The therapeutic package of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

A pharmaceutical composition in unit dosage form, useful in treating a subject afflicted with pain, a depressive disorder, an anxiety disorder or a mood disorder, which comprises:
(i) an amount of any compound of the present invention, or a salt or ester thereof; and
(ii) an amount of an NMDA receptor antagonist, an NMDA receptor partial agonist, a neurokinin 1 receptor antagonist, a neurokinin 2 receptor antagonist, a neurokinin 3 receptor antagonist, or a DOR agonist,
wherein the respective amounts of said compound and said agonist or antagonist in said composition are effective, upon concomitant administration to said subject of one or more of said unit dosage forms of said composition, to treat the subject.

The pharmaceutical composition of the above embodiment, wherein the respective amounts of said compound and said agonist or antagonist in said unit dose when taken together is more effective to treat the subject than when compared to the administration of said compound in the absence of said agonist or antagonist or the administration of said agonist or antagonist in the absence of said compound.

In some embodiments of the present method, compound, package, use or pharmaceutical composition, the compound has the structure:

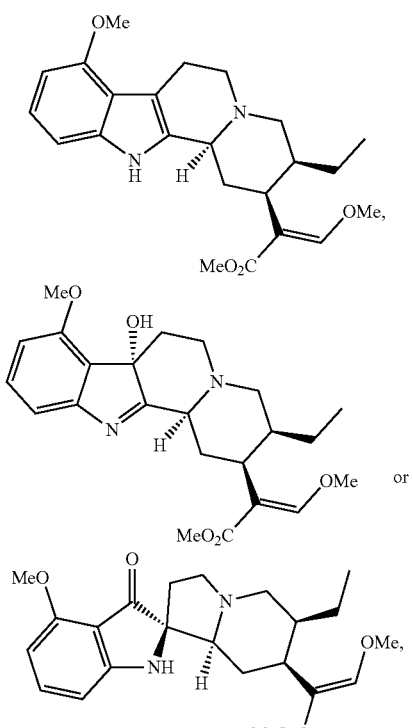

In some embodiments of the present method, compound, package, use or pharmaceutical composition, the compound has the structure:

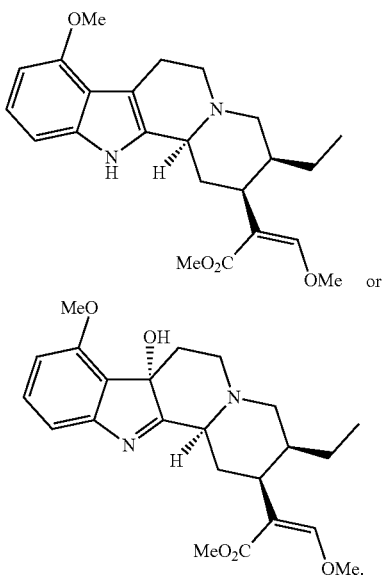

In some embodiments, a pharmaceutically acceptable salt of any of the above compounds of the present invention.

In some embodiments, a salt of the compound of the present invention is used in any of the above methods, uses, packages or compositions.

In some embodiments, a pharmaceutically acceptable salt of the compound of the present invention is used in any of the above methods, uses, packages or compositions.

In some embodiments, an ester of the compound of the present invention is used in any of the above methods, uses, packages or compositions.

Any of the above compounds may be used in any of the disclosed methods, uses, packages or pharmaceutical compositions.

Any of the compounds used in the disclosed methods, uses, packages or pharmaceutical compositions may be replaced with any other compound disclosed in the present invention.

Any of the above generic compounds may be used in any of the disclosed methods, uses, packages or compositions.

Except where otherwise specified, the structure of a compound of this invention includes an asymmetric carbon atom, it is understood that the compound occurs as a racemate, racemic mixture, a scalemic mixture and isolated single enantiomer. All such isomeric forms of these compounds are expressly included in this invention. Except where otherwise specified, each stereogenic carbon may be of the P or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$ (D), or $^{3}H$ (T). Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

Deuterium (2H or D) is a stable, non-radioactive isotope of hydrogen and has an atomic weight of 2.0144. Hydrogen atom in a compound naturally occurs as a mixture of the isotopes 1H (hydrogen or protium), D (2H or deuterium), and T (3H or tritium). The natural abundance of deuterium is 0.0156%. Thus, a compound with a level of deuterium at any site of hydrogen atom in the compound that has been enriched to be greater than its natural abundance of 0.0156%, is novel over its non-enriched counterpart.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl or $C_2$-$C_8$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl or $C_3$-$C_8$ alkynyl.

As used herein, "hydroxyalkyl" includes alkyl groups as described above wherein one or more bonds to hydrogen contained therein are replaced by a bond to an —OH group. In some embodiments, $C_1$-$C_{12}$ hydroxyalkyl or $C_1$-$C_6$ hydroxyalkyl. $C_1$-$C_n$ as in "$C_1$-$C_n$ alkyl" is defined to include groups having 1, 2, . . . , n–1 or n carbons in a linear or branched arrangement (e.g. $C_1$-$C_2$ hydroxyalkyl, $C_1$-$C_3$ hydroxyalkyl, $C_1$-$C_4$ hydroxyalkyl, $C_1$-$C_5$ hydroxyalkyl, or $C_1$-$C_6$ hydroxyalkyl) For example, $C_1$-$C_6$, as in "$C_1$-$C_6$ hydroxyalkyl" is defined to include groups having 1, 2, 3, 4, 5, or 6 carbons in a linear or branched alkyl arrangement wherein a hydrogen contained therein is replaced by a bond to an —OH group.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The term "ester" is intended to a mean an organic compound containing the R—O—CO—R' group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reactions and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30th edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkali metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

General Considerations (Synthesis).

Reagents and solvents were obtained from commercial sources and were used without further purification unless otherwise stated (including anhydrous solvents). All reactions were performed in flame-dried glassware under an argon atmosphere unless otherwise stated, and monitored by TLC using solvent mixtures appropriate to each reaction. All column chromatography was performed on silica gel (40-63 µm). For compounds containing a basic nitrogen, $Et_3N$ was often used in the mobile phase in order to provide better resolution. In these cases, TLC plates were pre-soaked in the $Et_3N$-containing solvent and then allowed to dry briefly before use in analysis, such that an accurate representation of $R_f$ was obtained. Nuclear magnetic resonance spectra were recorded on 400 or 500 MHz instruments as indicated. Chemical shifts are reported as δ values in ppm referenced to $CDCl_3$ ($^1H$ NMR=7.26 and $^{13}C$ NMR=77.16) or $(CD_3)_2SO$ ($^1H$ NMR=2.50 and $^{13}C$ NMR=39.52). Multiplicity is indicated as follows: s (singlet); d (doublet); t (triplet); q (quartet); dd (doublet of doublets); ddd (doublet of doublets of doublets); dt (doublet of triplets); td (triplet of doublets); m (multiplet); br (broad). In some cases, spectra are complicated by the presence of multiple conformers, resulting in peak broadening or additional splitting. As a result of these effects, multiple peaks may correspond to the same proton group or carbon atom. When possible, this is indicated by an "and" joining two listed peaks or spectral regions. All carbon peaks are rounded to one decimal place unless such rounding would cause two close peaks to become identical. In these cases, two decimal places are retained. Low-resolution mass spectra (LRMS) were recorded on a quadrupole mass spectrometer (ionization mode: APCI+ or ESI+).

Example 1. Isolation of *Mitragyna speciosa* Alkaloids

Scheme 1. Structures of naturally occurring *Mitragyna* alkaloids.

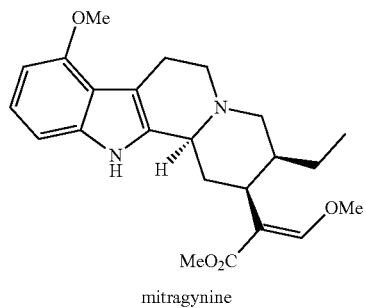

mitragynine

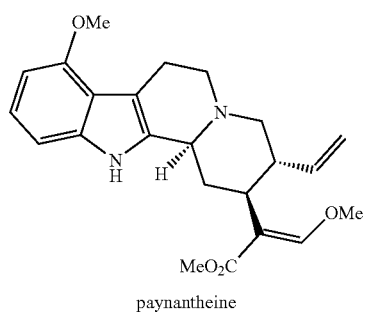

paynantheine

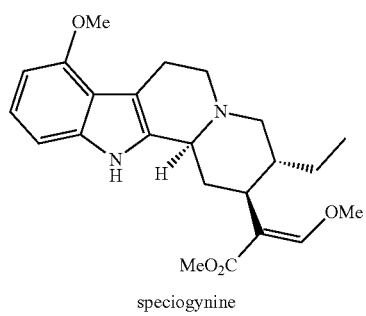

speciogynine

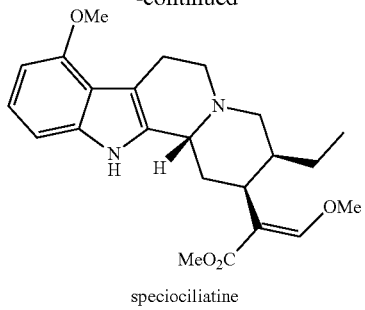

speciociliatine

Isolation of *Mitragyna speciosa* Alkaloids.

Dry, finely powdered *Mitragyna speciosa* leaves (186 g) (Thai strain, Arena Ethnobotanicals, Del Mar, CA) were extracted repeatedly with boiling MeOH (4×500 mL), vacuum filtering the solids thoroughly between each extraction. The combined extracts were concentrated to provide a dark green-black solid (56.19 g). This material was crushed and extracted twice with room temperature 10% aqueous AcOH (2×300 mL), filtering each extract through celite (slow). The combined, coffee-colored acidic extracts, were washed with hexanes (2×150 mL) and carefully basified (with ice cooling) to pH 8-9 using concentrated aqueous NaOH (thick tan precipitate forms). The basic mixture was then extracted thoroughly with CHCl$_3$ (6×200 mL, emulsions), shaking vigorously with each extraction (not all solids dissolve). The combined organics were washed with water (2×400 mL), dried over Na$_2$SO$_4$, and concentrated to yield the crude alkaloid fraction as a foamy brown solid (3.62 g, 1.9 mass %). TLC analysis of this material revealed four distinct spots (mitragynine, paynantheine, speciogynine, and speciociliatine in order of increasing polarity), in addition to baseline. The crude alkaloid mixture was separated by column chromatography (8:2→7:3→6:4→1:1 hexanes:EtOAc+2% Et$_3$N, 2 column volumes each) to provide fractions containing pure mitragynine (1.38 g), mitragynine+minor paynantheine and speciogynine (0.25 g), paynantheine and speciogynine+minor mitragynine and speciociliatine (0.61 g), speciociliatine+minor paynantheine and speciogynine (0.20 g), and speciociliatine+minor impurities (0.20 g). These mixed fractions were further separated by repeated column chromatography (gradients of hexanes: EtOAc mixtures, with or without 2% Et$_3$N) to provide additional mitragynine (190 mg), along with pure samples of paynantheine (46 mg), speciogynine (12 mg), and speciociliatine (148 mg). The total yield of isolated mitragynine was 1.57 g (0.84 mass %), and of total mixed paynantheine, speciogynine, and speciocoliatine was 1.01 g (0.54 mass %). However, the yields for the pure samples of the minor alkaloids should not be considered indicative of the quantities contained in the plant material, due to purification losses.

This isolation procedure was repeated a second time on a larger, separate batch of powdered *Mitragyna speciosa* leaves (454 g), scaling quantities appropriately. It should be noted that in this second extraction, it was found that basification of the aqueous extracts to pH 12 (instead of 8-9) was beneficial, as it prevented the formation of emulsions in the subsequent CHCl$_3$ extractions. This extraction provided the crude alkaloid fraction as a foamy, greenish-brown solid (8.03 g, 1.8 mass %). The mixed alkaloids were separated by column chromatography as before, to provide pure mitragynine (3.33 g, 0.73 mass %) and fractions containing mixtures of the minor alkaloids (total >3 g). No effort was made to further purify paynantheine, speciogynine, and speciociliatine from the mixed fractions, but the ratios between these alkaloids clearly differed from the first extraction, with speciociliatine being significantly more prevalent.

Mitragynine.

Isolated as an amorphous, pale-yellow solid. $[\alpha]^{25}_D = -136.9$ (CHCl$_3$); $t_R = 8.33$ min (Daicel Chiralcel OD column, 8:2 hexanes:iPrOH+0.20% Et$_2$NH, 1 mL/min); $^1$H NMR (500 MHz, CDCl$_3$) δ 7.71 (br s, 1H), 7.43 (s, 1H), 6.99 (t, J=7.9 Hz, 1H), 6.90 (d, J=8.0 Hz, 1H), 6.46 (d, J=7.7 Hz, 1H), 3.88 (s, 3H), 3.73 (s, 3H), 3.71 (s, 3H), 3.18-3.07 (m, 2H), 3.07-2.99 (m, 2H), 2.97 (dd, J=15.5, 4.0 Hz, 1H), 2.92 (dd, J=11.3, 5.8 Hz, 1H), 2.57-2.48 (m, 2H), 2.45 (dd, J=11.7, 2.8 Hz, 1H), 1.84-1.73 (m, 2H), 1.65-1.61 (m, 1H), 1.24-1.15 (m, 1H), 0.87 (t, J=7.4 Hz, 3H); $^{13}$C NMR (126 MHz, CDCl$_3$) δ 169.4, 160.7, 154.6, 137.4, 133.9, 121.9, 117.8, 111.6, 108.0, 104.3, 99.9, 61.7, 61.4, 57.9, 55.5, 53.9, 51.5, 40.8, 40.1, 30.1, 24.1, 19.2, 13.0; LRMS (APCI+) calcd. for C$_{23}$H$_{31}$N$_2$O$_4$$^+$ [M+H]$^+$ 399.23, found 399.06.

Paynantheine.

Isolated as an amorphous, pale-pink solid. $^1$H NMR (400 MHz, CDCl$_3$) δ 7.81 (br s, 1H), 7.33 (s, 1H), 7.00 (t, J=7.9 Hz, 1H), 6.87 (d, J=8.0 Hz, 1H), 6.46 (d, J=7.6 Hz, 1H), 5.64-5.52 (m, 1H), 5.00 (dd, J=17.2, 1.4 Hz, 1H), 4.95 (dd, J=10.3, 2.0 Hz, 1H), 3.87 (s, 3H), 3.76 (s, 3H), 3.70 (s, 3H), 3.26 (d, J=11.1 Hz, 1H), 3.23-3.12 (m, 1H), 3.11-2.96 (m, 4H), 2.76 (td, J=11.8, 3.7 Hz, 1H), 2.59 (td, J=11.2, 4.3 Hz, 1H), 2.29 (t, J=11.9 Hz, 1H), 2.09 (dd, J=24.5, 12.5 Hz, 1H), 1.98-1.91 (m, 1H); LRMS (APCI+) calcd. for C$_{23}$H$_{29}$N$_2$O$_4$$^+$ [M+H]$^+$ 397.21, found 397.06.

Speciogynine.

Isolated as an amorphous, yellow-tan solid. $^1$H NMR (400 MHz, CDCl$_3$) δ 7.74 (br s, 1H), 7.39 (br s, 1H), 7.02 (t, J=7.9 Hz, 1H), 6.90 (d, J=7.8 Hz, 1H), 6.48 (d, J=7.5 Hz, 1H), 3.90 (s, 3H), 3.75 (br s, 6H), 3.30-3.14 (m, 3H), 3.10 (dd, J=11.3, 5.5 Hz, 1H), 3.06-2.98 (m, 1H), 2.70-2.53 (m, 2H), 2.37-2.23 (m, 1H), 2.08 (t, J=11.0 Hz, 2H), 1.98 (br s, 1H), 1.45 (br s, 1H), 1.06 (br s, 1H), 0.89 (t, J=7.5 Hz, 3H); LRMS (APCI+) calcd. for C$_{23}$H$_{31}$N$_2$O$_4$$^+$ [M+H]$^+$ 399.23, found 399.07.

Speciociliatine.

Isolated as an amorphous, orange solid. $^1$H NMR (400 MHz, CDCl$_3$) δ 7.70 (br s, 1H), 7.45 (s, 1H), 7.04 (t, J=7.9 Hz, 1H), 6.94 (d, J=7.6 Hz, 1H), 6.50 (d, J=7.6 Hz, 1H), 4.14 (br s, 1H), 3.92 (s, 3H), 3.81 (s, 3H), 3.70 (s, 3H), 3.28-3.10 (m, 2H), 3.10-2.96 (m, 2H), 2.96-2.88 (m, 2H), 2.79 (dd, J=10.9, 5.7 Hz, 1H), 2.65 (br s, 1H), 1.97-1.88 (m, 1H), 1.77 (br s, 1H), 1.72-1.61 (m, 1H), 1.35-1.22 (m, 1H), 0.92 (t, J=7.3 Hz, 3H); LRMS (APCI+) calcd. for C$_{23}$H$_{31}$N$_2$O$_4$$^+$ [M+H]$^+$ 399.23, found 399.04.

Example 2. Oxidation of Mitragynine Using Singlet Oxygen (Photooxidation)

The oxidation of mitragynine or analogs thereof to the corresponding 7-hydroxy derivatives may be performed by a photochemical process.

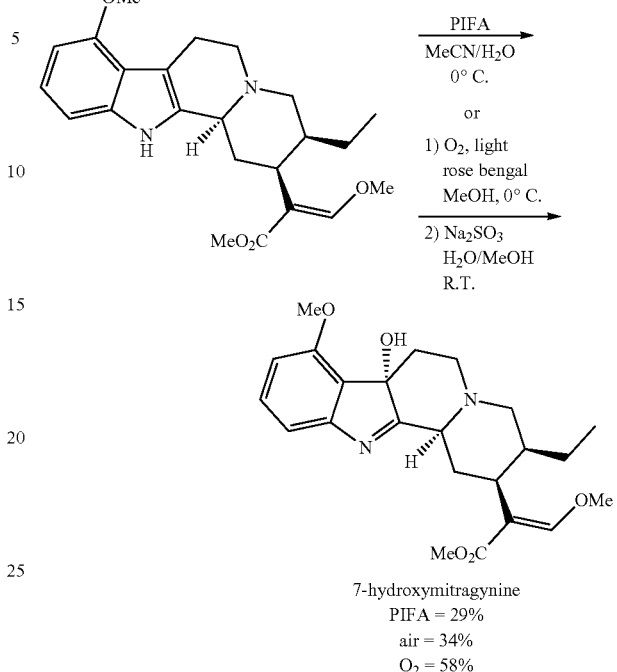

Scheme 2. Oxidation of mitragynine to produce 7-hydroxymitragynine.

7-hydroxymitragynine
PIFA = 29%
air = 34%
O$_2$ = 58%

7-Hydroxymitragynine: PIFA Oxidation (Takayama, H. et al. 2014). To a solution of mitragynine (399 mg, 1.00 mmol) in CH$_3$CN (14 mL) and water (5 mL) at 0° C., was added a solution of [bis (trifluoroacetoxy)iodo]benzene (PIFA, 473 mg, 1.10 mmol) in CH$_3$CN (4 mL) dropwise over 4 min, and the resulting orange solution was left to stir. Additional solid PIFA was added in portions over the next several hours (43.0 mg, 86.0 mg, and 43.0 mg at 1.25 h, 1.75 h, and 2.5 h respectively). After 3 h, the reaction was poured into saturated aqueous NaHCO$_3$ (40 mL) at 0° C. and extracted with CH$_2$Cl$_2$ (3×30 mL). The combined organics were washed with water (30 mL) and brine (30 mL), dried over Na$_2$SO$_4$, and concentrated to provide a dark-brown solid (507 mg). The material was purified by repeated column chromatography (Column 1: 6:4 hexanes: EtOAc+2, Et$_3$N; Column 2: 8:2 CH$_2$Cl$_2$:Et$_2$O; Column 3: 6:4 hexanes:EtOAc+2% Et$_3$N) to provide the pure product as a pale-yellow, amorphous solid (121 mg, 29%). $^1$H NMR (400 MHz, CDCl$_3$) δ 7.44 (s, 1H), 7.30 (t, J=8.0 Hz, 1H), 7.21 (d, J=7.5 Hz, 1H), 6.74 (d, J=8.2 Hz, 1H), 3.87 (s, 3H), 3.81 (s, 3H), 3.70 (s, 3H), 3.12 (dd, J=11.1, 2.3 Hz, 1H), 3.08-2.97 (m, 2H), 2.88-2.75 (m, 2H), 2.68-2.59 (m, 2H), 2.48 (dd, J=11.5, 2.5 Hz, 1H), 2.18 (s, 1H), 1.89 (d, J=13.6 Hz, 1H), 1.76-1.63 (m, 2H), 1.62-1.56 (m, 1H), 1.30-1.18 (m, 1H), 0.82 (t, J=7.3 Hz, 3H); LRMS (APCI+) calcd. for C$_{23}$H$_{31}$N$_2$O$_5$$^+$ [M+H]$^+$ 415.22, found 415.30.

7—Hydroxymitragynine: Photooxidation Under Air.

A solution of mitragynine (319 mg, 0.800 mmol) and rose bengal Na salt (8.0 mg) in MeOH (1.6 mL) was irradiated with a 500 W halogen lamp at 0° C. under air for 32 h. Additional MeOH (5.0 mL) and a solution of Na$_2$SO$_3$ (504 mg, 4.00 mmol) in water (4.5 mL) were both added and the pink mixture was stirred vigorously at room temperature until mass spectrometry indicated the disappearance of the hydroperoxide intermediate (23 h). The reaction was then diluted with water (20 mL) and extracted with Et$_2$O (3×20 mL). The combined organics were washed with water (2×20 mL) and brine (20 mL), dried over Na$_2$SO$_4$, and concentrated to provide a foamy orange solid (215 mg). This material was purified by column chromatography (6:4 hexanes:EtOAc+2% Et$_3$N) to provide the pure product as a yellow amorphous solid (114 mg, 34%) with spectral properties identical to the material obtained from the PIFA oxidation (above).

7—Hydroxymitragynine: Photooxidation Under O$_2$.

A solution of mitragynine (20.0 mg, 0.0500 mmol) and rose bengal Na salt (0.5 mg) in MeOH (0.30 mL) was irradiated with a 500 W halogen work lamp at 0° C. under 02 atmosphere for 1.5 h. Additional MeOH (0.30 mL) and a solution of Na$_2$SO$_3$ (30.0 mg, 0.240 mmol) in water (0.27 mL) were both added, and the pink mixture was stirred vigorously at room temperature until mass spectrometry indicated the disappearance of the hydroperoxide intermediate (5 h). The reaction was then diluted with water (2 mL) and extracted with Et$_2$O (3×2 mL). The combined organics were washed with water (2×2 mL) and brine (2 mL), dried over Na$_2$SO$_4$, and concentrated to provide a foamy orange-brown solid (17.9 mg). The yield of product contained in this material was determined by NMR using mesitylene as an internal standard (58% yield).

Example 3. Preparation of Mitragynine Pseudoindoxyl

Scheme 3. Synthesis of mitragynine pseudoindoxyl.

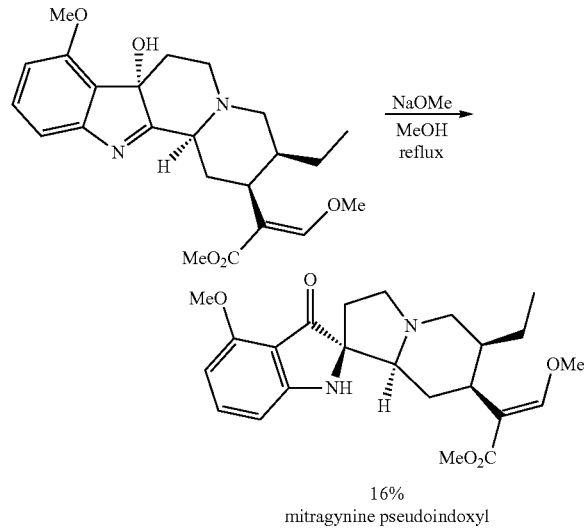

16%
mitragynine pseudoindoxyl

Mitragynine pseudoindoxyl=methyl (E)-2-((2S,6'S, 7'S,8a'S)-6'-ethyl-4-methoxy-3-oxo-2',3',6',7',8',8a'-hexahydro-5'H-spiro[indoline-2,1'-indolizin]-7'-yl)-3-methoxyacrylate A fresh solution of sodium methoxide was prepared by dissolving Na metal (7.6 mg, 0.330 mmol) in anhydrous MeOH (5.6 mL) at room temperature. To this solution was then added 7-hydroxymitragynine (62.2 mg, 0.150 mmol) and the yellow solution was refluxed for 4.5 h (incomplete conversion). After cooling to room temperature, the reaction was diluted with water (20 mL) and extracted with Et$_2$O (3×20 mL). The combined organics were washed with water (10 mL) and brine (10 mL), dried over Na$_2$SO$_4$, and concentrated to provide a brown foam (60 mg). This material was purified by repeated preparative TLC (1 mm silica layer, 20×20 cm plates; Plate 1: Et$_3$O+2% Et$_3$N; Plate 2: 7:3 CH$_2$Cl$_2$:Et$_2$O; Plate 3: Et$_2$O+2% Et$_3$N) to provide spirocyclic product 5 as a foamy yellow solid (9.9 mg, 16%). $^1$H NMR (500 MHz, CDCl$_3$) δ 7.31 (t, J=8.1 Hz, 1H), 7.28 (s, 1H), 6.40 (d, J=8.1 Hz, 1H), 6.13 (d, J=8.1 Hz, 1H), 5.11 (br s, 1H), 3.89 (s, 3H), 3.66 (s, 3H), 3.62 (s, 3H), 3.12 (br s, 2H), 2.77 (d, J=12.1 Hz, 1H), 2.41-2.28 (m, 2H), 2.28-2.08 (m, 3H), 1.90 (br s, 1H), 1.64 (br s, 1H), 1.51 (br s, 1H), 1.23-1.16 (m, 1H), 1.16-1.08 (m, 1H), 0.85 (t, J=7.4 Hz, 3H); $^{13}$C NMR (126 MHz, CDCl$_3$) δ 199.6, 169.0, 162.2, 160.4, 158.7, 138.8, 125.7, 111.8, 103.9, 99.2, 75.3, 73.4, 61.6, 55.8, 54.9, 53.3, 51.3, 40.2, 38.5, 35.2, 23.9, 19.4, 13.0; LR-MS calcd. for C$_{23}$H$_{31}$N$_2$O$_5^+$ [M+H]$^+$ 415.22, found 416.36.

Example 4. Opioid Activity of Mitragynine and Oxidized Derivatives

Mitragynine, 7-hydroxymitragynine, and mitragynine pseudoindoxyl were tested for agonist and antagonist activity at the human mu-opioid receptor (MOR), kappa-opioid receptor (KOR), and delta-opioid receptor (DOR) using bioluminescence resonance energy transfer (BRET) assays measuring G protein activation as previously described (Table 1) (Rives, M.-L. et al. 2012; Negri, A. et al. 2013).

Transfection.

Human MOR, KOR, or DOR cDNA was transfected alongside Gα$_{oB}$ with RLuc8 inserted at position 91 (Gα$_{oB}$-RLuc8), Gβ$_1$ (β$_1$), and Gγ$_2$ fused to the full-length mVenus at its N terminus (mVenus-γ2) (2.5 μg MOR/DOR/KOR, 0.125 μg Gα$_{oB}$-RLuc8, 6.25 μg β$_1$; 6.25 μg mVenus-γ2) into HEK-293T cells (5×10$^6$ cells/plate) in 10-cm dishes using PEI (Polysciences Inc.; Warrington, PA) in a 1:1 ratio diluted in Opti-MEM (Life Technologies Corp.; Grand Island, NY) to assay for G protein activation as described previously.[2,3] Cells were maintained in Dulbecco's Modified Eagle Medium (high glucose #11965; Life Technologies) supplemented with 10% FBS (Premium Select, Atlanta Biologicals; Atlanta, GA) and 100 U/mL penicillin and 100 μg/mL streptomycin (#15140, Life Technologies). After 24 hours the media was changed, and the experiment was performed 24 hours later (48 hours after transfection).

BRET.

Transfected cells were dissociated and resuspended in phosphate-buffered saline (PBS). Approximately 200,000 cells/well were added to a black-framed, white well 96-well plate (#60050; Perkin Elmer; Waltham, MA). The microplate was centrifuged and the cells were resuspended in phosphate-buffered saline (PBS). For agonist experiments, after 5 minutes, 5 μM of the luciferase substrate coelenterazine H was added to each well. After 5 minutes, ligands were added and the BRET signal was measured at 5 minutes on a PHERAstar FS plate reader. For antagonist competition experiments, cells were preincubated with the antagonist at varying concentrations for 30 minutes. Coelenterazine H (5 μM) was then added to each well for 5 minutes. Following coelenterazine H incubation, a fixed concentration of the reference agonist (5×EC$_{50}$) was added, and the BRET signal was measured at 30 minutes on a PHERAstar FS plate reader. The BRET signal was quantified by calculating the ratio of the light emitted by the energy acceptor, mVenus (510-540 nm), over the light emitted by the energy donor, RLuc8 (485 nm). This drug-induced BRET signal was normalized using the E$_{max}$ of [D-Ala2, N-Me-Phe4, Gly5-ol]-enkephalin (DAMGO), U-50,488, or [D-Pen(2,5)]enkephalin (DPDPE) as the maximal response at MOR, KOR, and DOR respectively. Dose response curves were fit using a three-parameter logistic equation in GraphPad Prism 6.

TABLE 1

Functional activity of compounds at human MOR, KOR (FIG. 1), and DOR. Agonist activity is indicated by $EC_{50}$ values with $E_{max}$ in parentheses. Antagonist activity is indicated by $IC_{50}$ values for the inhibition of the corresponding reference agonist at 5x its $EC_{50}$ concentration. In some cases, $pA_2$ values (an estimate of Ki) obtained from Schild analysis are also provided for antagonist activity. Where indicated, error represents ±SEM of 2 or more independent trials.

| Compound | Structure | Human MOR | Human KOR | Human DOR |
|---|---|---|---|---|
| mitragynine | 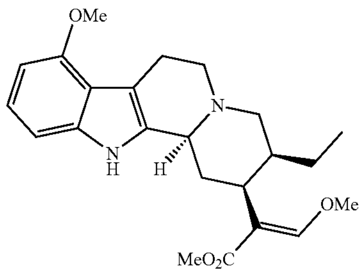 [SMILES: CC[C@@H]1CN2CCc3c([nH]c4cccc(OC)c34)[C@@H]2C[C@@H]1/C(=C\OC)C(=O)OC] | $EC_{50}$ = 339 ± 178 nM (34%) | Antagonist $IC_{50}$ = 8.5 ± 7.6 μM (Schild $pA_2$ = 1.4 ± 0.4 μM) | Antagonist $IC_{50}$ = >50 μM |
| 7-hydroxy-mitragynine | 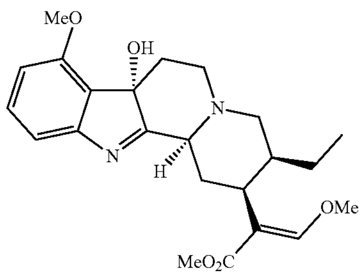 | $EC_{50}$ = 34.5 ± 4.5 nM (60%) | Antagonist $IC_{50}$ = 7.9 ± 3.7 μM (Schild $pA_2$ = 490 ± 131 nM) | Antagonist $IC_{50}$ = 15.6 ± 9.1 μM |
| mitragynine pseudoindoxyl | 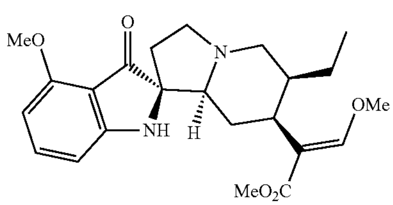 [SMILES: CC[C@@H]1CN2CC[C@]3(Nc4cccc(OC)c4C3=O)[C@@H]2C[C@@H]1/C(=C\OC)C(=O)OC] | $EC_{50}$ = 14.5 ± 4.4 nM (52%) | Antagonist $IC_{50}$ = 4.8 ± 2.3 μM | Antagonist $IC_{50}$ = 609 ± 229 nM |

Example 5. Total Synthesis of Mitragynine and (Z)-Mitragynine

Mitragynine and its unnatural stereoisomer, (Z)-mitragynine, were synthesized starting from 4-methoxyindole according to the procedures described below.

Scheme 4. Synthesis of starting materials.

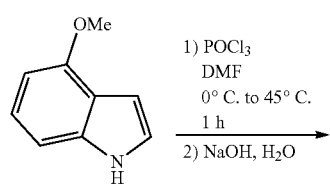

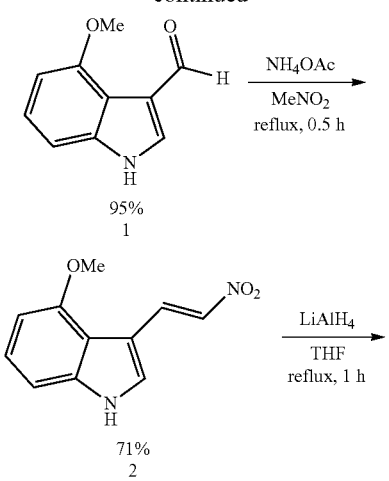

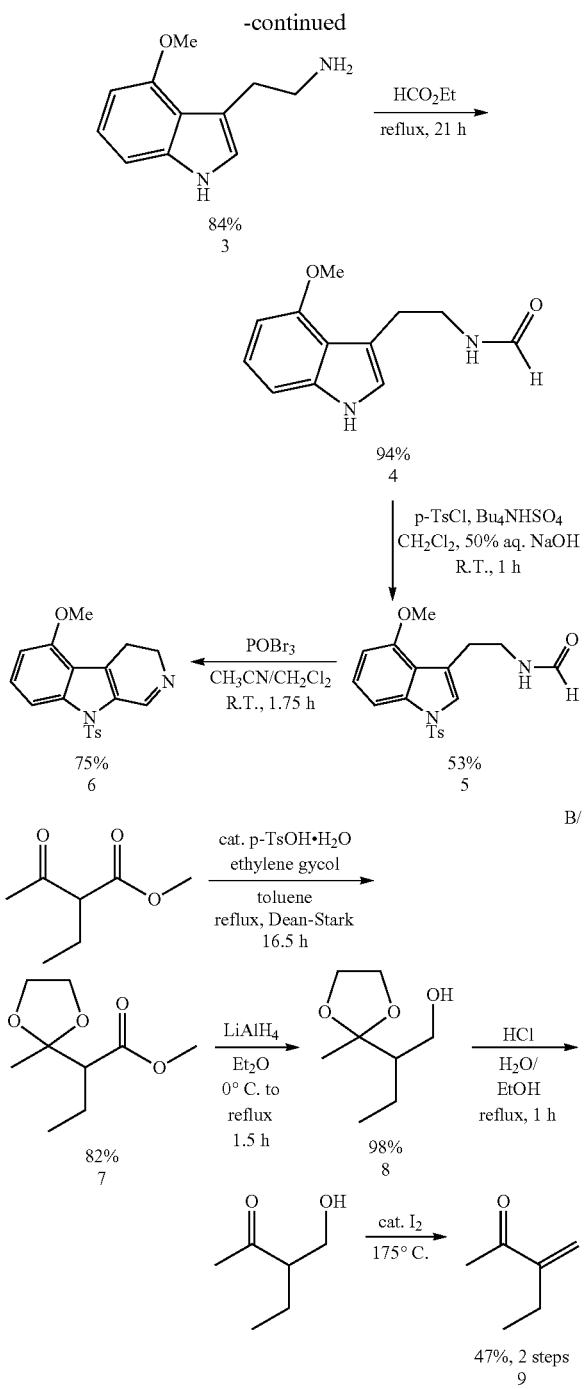

4-Methoxy-19-indole-3-carbaldehyde (1)

Phosphoryl chloride (9.61 mL, 105 mmol) was added slowly over 3 min to anhydrous DMF (60 mL) at 0° C. A solution of 4-methoxyindole (10.30 g, 70.00 mmol) in anhydrous DMF (40 mL) was then added slowly over 5 min. The resulting bright yellow suspension was heated to 45° C. and stirred for 1 h. The reaction was then quenched with ice water (800 mL), and the resulting purplish-brown solution was washed with Et$_2$O (2×100 mL) (Note: If insufficient water is used, a voluminous precipitate may form during the Et$_2$O washes.). The washed aqueous layer was basified with concentrated aqueous NaOH (effervescence), resulting in a color change to pale-yellow and slow formation of a crystalline precipitate (Note: This precipitate is an adduct of the product and should not be collected). The basic mixture was then extracted with Et$_2$O (3×600 mL) (Note: Lesser quantities of Et$_2$O can be used if the aqueous/organic mixture is left to stir overnight.), and the combined organics were washed with brine (200 mL), dried over Na$_2$SO$_4$, and concentrated to provide the product 1 as a tan crystalline solid (11.69 g, 95%). $^1$H NMR (400 MHz, CDCl$_3$) δ 10.51 (s, 1H), 8.96 (br s, 1H), 7.93 (d, J=3.1 Hz, 1H), 7.22 (t, J=8.0 Hz, 1H), 7.08 (d, J=8.2 Hz, 1H), 6.73 (d, J=7.9 Hz, 1H), 4.01 (s, 3H); $^{13}$C NMR (101 MHz, CDCl$_3$) δ 188.6, 154.7, 137.9, 128.8, 124.5, 119.6, 116.3, 105.4, 102.8, 55.5.

(Z)-4-Methoxy-3-(2-nitrovinyl)-1H-indole (2)

A mixture of aldehyde 1 (11.68 g, 66.67 mmol) and ammonium acetate (12.85 g, 166.7 mmol) in nitromethane (200 mL) was refluxed for 30 min and then concentrated to provide a bright orange-red solid (17.27 g). This material was triturated with water (100 mL), and the wash water was removed by filtration. All solids were recombined, the water washing procedure was repeated twice more, and the resulting solids were dried in vacuo. This crude material was then recrystallized from MeOH to provide several crops of pure product 2 as dark-red needles (or orange-red powder, color dependent on crystal size) (10.29 g, 713). $^1$H NMR (400 MHz, (CD$_3$)$_2$SO) δ 12.23 (br s, 1H), 8.56 (d, J=13.3 Hz, 1H), 8.26 (s, 1H), 8.10 (d, J=13.3 Hz, 1H), 7.17 (t, J=7.9 Hz, 1H), 7.10 (d, J=7.6 Hz, 1H), 6.74 (d, J=7.7 Hz, 1H), 3.95 (s, 3H); $^{13}$C NMR (101 MHz, (CD$_3$)$_2$SO) δ 153.6, 138.8, 135.5, 132.2, 124.3, 115.1, 107.9, 106.0, 102.5, 55.4.

2-(4-Methoxy-1H-indol-3-yl)ethan-1-amine (3)

To a suspension of LiAlH$_4$ (7.00 g, 185 mmol) in anhydrous THF (70 mL) was slowly added a solution of nitrovinylindole 2 (6.28 g, 28.8 mmol) in anhydrous THF (165 mL) with ice cooling over 15 min. The resulting orange-gray suspension was refluxed for 1 h and then cooled in ice and carefully quenched by the addition of water (7 mL), 15 aqueous NaOH (7 mL), and water again (21 mL). The mixture was stirred until the solids were white and loose and then filtered, washing the filter cake with several portions of THF (4×). The combined filtrate and washings were concentrated to provide a pale-brown solid (5.26 g). This material was re-dissolved in CH$_2$Cl$_2$ (300 mL), washed with water (100 mL), and then extracted with 5% aqueous HCl (100 mL) followed by water (2×100 mL). The combined acidic extracts were washed with CH$_2$Cl$_2$ (100 mL), basified with concentrated aqueous NaOH, and extracted with CH$_2$Cl$_2$ (2×100 mL, 50 mL). The combined organics were washed with brine (100 mL), dried over Na$_2$SO$_4$, and concentrated to yield the pure product 3 as a pale, grayish-brown solid (4.61 g, 84%). $^1$H NMR (400 MHz, CDCl$_3$) δ 8.18 (br s, 1H), 7.08 (t, J=8.0 Hz, 1H), 6.96 (d, J=8.1 Hz, 1H), 6.88 (s, 1H), 6.49 (d, J=7.7 Hz, 1H), 3.92 (s, 3H), 3.01 (s, 4H), 1.36 (br s, 2H); $^{13}$C NMR (101 MHz, CDCl$_3$) δ 155.02, 138.39, 122.89, 121.09, 117.52, 114.35, 104.61, 99.50, 55.23, 43.43, 31.29.

N-(2-(4-Methoxy-1H-indol-3-yl)ethyl)formamide (4)

A suspension of tryptamine 3 (6.76 g, 35.5 mmol) in ethyl formate (60 mL) was refluxed for 21 h (solids dissolve) and then concentrated to provide a viscous brown oil. This was dissolved in $CH_2Cl_2$ (100 mL), washed with 3% aqueous HCl (100 mL), saturated aqueous $K_2CO_3$ (100 mL), and brine, dried over $Na_2SO_4$, and concentrated to give the product 4 as a viscous brown oil (7.32 g, 94%). $^1$H NMR (400 MHz, $CDCl_3$) (spectrum complicated by conformers) δ 8.15 (br s, 1H), 8.09 and 7.94 and 7.91 (s, 1H), 7.10 (t, J=8.0 Hz, 1H), 6.98 and 6.97 (d, J=8.2, 1H), 6.90 and 6.85 (d, J=2.1 Hz, 1H), 6.512 and 6.505 (d, J=7.7, 1H), 5.87 and 5.67 (br s, 1H), 3.94 and 3.93 (s, 3H), 3.64 and 3.54 (q, J=6.1 Hz, 2H), 3.10 and 3.05 (t, J=6.5 Hz, 2H); $^{13}$C NMR (126 MHz, $CDCl_3$) δ 164.9 and 161.4, 154.5, 138.3, 123.1 and 123.0, 121.8 and 121.5, 117.2 and 116.9, 113.1 and 112.1, 104.9, 99.6 and 99.5, 55.2 and 53.6, 43.3 and 39.8, 29.1 and 26.4; LMS (ESI+) calcd. for $C_{12}H_{14}N_2NaO_2^+$ [M+Na]$^+$ 241.09, found 241.01.

N-(2-(4-Methoxy-1-tosyl-1H-indol-3-yl)ethyl)formamide (5)

To a solution of formyltryptamine 4 (7.26 g, 33.3 mmol), p-toluenesulfonyl chloride (11.10 g, 58.21 mmol), and tetrabutylammonium hydrogensulfate (1.13 g, 3.33 mmol) in $CH_2Cl_2$ (170 mL) was added 50% m/m aqueous NaOH (16.6 mL), and the resulting mixture was stirred vigorously at room temperature for 1 h. The reaction was then diluted with water (200 mL), the organic layer was separated, and the remaining aqueous layer was extracted with additional $CH_2Cl_2$ (2×50 mL). The combined organics were washed with water (2×150 mL) and brine (150 mL), dried over $Na_2SO_4$, and concentrated to give a foamy, pale-brown solid (15.1 g). This material was purified by column chromatography (EtOAc) to provide the product 5 as an off-white solid (6.60 g, 53%). $^1$H NMR (400 MHz, $CDCl_3$) (spectrum complicated by conformers) δ 8.11 and 7.93 and 7.90 (s, 1H), 7.76-7.69 (m, 2H), 7.60 and 7.58 (d, J=8.0 Hz, 1H), 7.26-7.19 (m, 4H), 6.64 (d, J=8.0 Hz, 1H), 5.59 (br s, 1H), 3.88 (s, 3H), 3.60 and 3.49 (q, J=6.3 Hz, 2H), 3.01 and 2.99 (t, J=6.6 Hz, 2H), 2.34 (s, 3H); $^{13}$C NMR (101 MHz, $CDCl_3$) (spectrum complicated by conformers) δ 164.5, 161.2, 154.4, 145.1, 137.2, 135.3, 130.1 and 130.00, 127.0, 126.0, 123.1 and 122.8, 120.1 and 119.8, 107.0, 103.9, 55.5, 42.4 and 38.6, 29.3 and 26.8, 21.7; LMS (APCI+) calcd. for $C_{19}H_{21}N_2O_4S^+$ [M+H]$^+$ 373.12, found 373.30.

5-Methoxy-9-tosyl-4,9-dihydro-3H-pyrido[3,4-b]indole (6)

To a solution of protected tryptamine 5 (6.39 g, 17.16 mmol) in anhydrous $CH_3CN$ (86 mL) and anhydrous $CH_2Cl_2$ (86 mL) at room temperature was added a solution of phosphoryl bromide (14.76 g, 51.48 mmol) in anhydrous $CH_3CN$ (43 mL) slowly over 5 min. The resulting yellow solution was stirred for 1.75 h and then quenched with water (350 mL). After basification with saturated $NH_4OH$, the mixture was extracted with $Et_2O$ (175 mL, 2×100 mL). The combined organics were washed with water (100 mL) and brine (100 mL), dried over $Na_2SO_4$, and concentrated to provide an orange-brown, foamy solid (5.65 g) (Note: The purity of this crude material is the same as after chromatography as judged by NMR). This was purified by column chromatography ($Et_2O$) to give the pure product 6 as a crystalline tan solid (4.57 g, 75). $^1$H NMR (500 MHz, $CDCl_3$) δ 8.93 (t, J=2.2 Hz, 1H), 7.76 (d, J=8.4 Hz, 1H), 7.67-7.62 (m, 2H), 7.32 (t, J=8.3 Hz, 1H), 7.17 (d, J=8.0 Hz, 2H), 6.64 (d, J=8.0 Hz, 1H), 3.85 (s, 3H), 3.81-3.74 (m, 2H), 2.99-2.92 (m, 2H), 2.32 (s, 3H); $^{13}$C NMR (126 MHz, $CDCl_3$) δ 155.4, 151.1, 145.2, 138.2, 134.9, 129.9, 128.4, 127.7, 126.8, 126.2, 118.2, 107.9, 104.6, 55.5, 47.6, 21.7, 20.8; LMS (APCI+) calcd. for $C_{19}H_{19}N_2O_3S^+$ [M+H]$^+$ 355.11, found 354.80.

Methyl 2-(2-methyl-1,3-dioxolan-2-yl)butanoate (7)

A mixture of methyl 2-ethyl-3-oxobutanoate (86.5 g, 600 mmol), ethylene glycol (44.5 mL, 49.5 g, 798 mmol), and p-toluenesulfonic acid monohydrate (50 mg) in toluene (190 mL) was refluxed for 17 h, removing water with a Dean-Stark trap. The reaction mixture was then washed with 5% aqueous $NaHCO_3$ (100 mL), water (100 mL), and brine (100 mL), dried over $Na_2SO_4$, and concentrated to provide ketal ester 7 as a pale-yellow oil (108 g) containing residual starting material and toluene (93.0 g, 82%, corrected for impurities). $^1$H NMR (400 MHz, $CDCl_3$) δ 4.05-3.88 (m, 4H), 3.71 (s, 3H), 2.58 (dd, J=11.4, 3.7 Hz, 1H), 1.82-1.70 (m, 1H), 1.70-1.61 (m, 1H), 1.39 (s, 3H), 0.89 (t, J=7.4 Hz, 3H); $^{13}$C NMR (126 MHz, $CDCl_3$) δ 173.4, 109.8, 64.91, 64.89, 56.3, 51.8, 21.59, 21.56, 12.5; LRMS (APCI+) calcd. for $C_9H_{17}O_4^+$ [M+H]$^+$ 189.11, found 189.06.

2-(2-Methyl-1,3-dioxolan-2-yl)butan-1-ol (8)

To a suspension of $LiAlH_4$ (14.69 g, 387 mmol) in anhydrous $Et_2O$ (46 mL) at 0° C. was slowly added a solution of ketal ester 7 (387 mmol, 72.9 g=84.4 g of crude corrected for toluene and starting material impurities) in anhydrous $Et_2O$ (182 mL) over 1.25 h. The resulting mixture was refluxed for 1 h and then quenched by the careful addition of water (14.7 mL), 15% aqueous NaOH (29.4 mL), and water again (14.7 mL). The mixture was stirred until the solids were white and loose and then filtered, washing the filter cake with several portions of $Et_2O$. The filtrate was washed with water (100 mL) and brine (100 mL), dried over $Na_2SO_4$, and concentrated to give ketal alcohol 8 as a pale-yellow oil (60.93 g, 98f). $^1$H NMR (400 MHz, $CDCl_3$) δ 3.99-3.92 (m, 4H), 3.70-3.57 (m, 2H), 2.71 (br s, 1H), 1.71-1.64 (m, 1H), 1.60-1.48 (m, 1H), 1.28 (s, 3H), 1.23-1.08 (m, 1H), 0.95 (t, J=7.4 Hz, 3H); $^{13}$C NMR (101 MHz, $CDCl_3$) δ 113.2, 64.6, 64.4, 62.3, 49.9, 20.7, 19.9, 12.7; LRMS (APCI+) calcd. for $C_8H_{17}O_3^+$ [M+H]$^+$ 161.12, found 161.58.

3-Methylenepentan-2-one (9)

A mixture of the ketal alcohol 8 (59.9 g, 374 mmol), water (136 mL), EtOH (13.6 mL), and 37% aqueous HCl (0.39 mL) was refluxed for 50 min. The mixture was then cooled to room temperature, neutralized with 2M aqueous NaOH, and saturated with $(NH_4)_2SO_4$ to salt out the product. The resulting heterogeneous mixture (yellow oil on top) was extracted with $Et_2O$ (2×200 mL) and the combined organics were dried over $Na_2SO_4$ and concentrated to provide the intermediate keto alcohol as a yellow oil (42.8 g) containing 10 mass % ethylene glycol impurity, which was used directly in the next step.

Iodine (2.88 g) was placed in a distillation apparatus and the boiling flask was preheated to 175° C. The crude keto alcohol was then added slowly over ~30 min by syringe while the product distilled over continuously at 84-110° C. The collected distillate (32.73 g) contained a cloudy yellow upper layer (product) and a colorless lower layer (water). After careful removal of the water layer, the crude product was obtained (25.49 g). A generous quantity of $Na_2SO_4$ was added to this material and it was redistilled through a 19 cm Vigreux column. The fraction distilling at 110-120° C. contained pure enone 9 as a very pale-yellow liquid (17.40 g, 47% over 2 steps). Bp 118° C.; $^1$H NMR (400 MHz, CDCl$_3$) δ 5.98 (s, 1H), 5.74 (t, J=1.4 Hz, 1H), 2.32 (s, 3H), 2.31-2.22 (m, 2H), 1.02 (t, J=7.4 Hz, 3H); $^{13}$C NMR (101 MHz, CDCl$_3$) δ 200.0, 150.8, 124.0, 26.1, 23.6, 12.7.

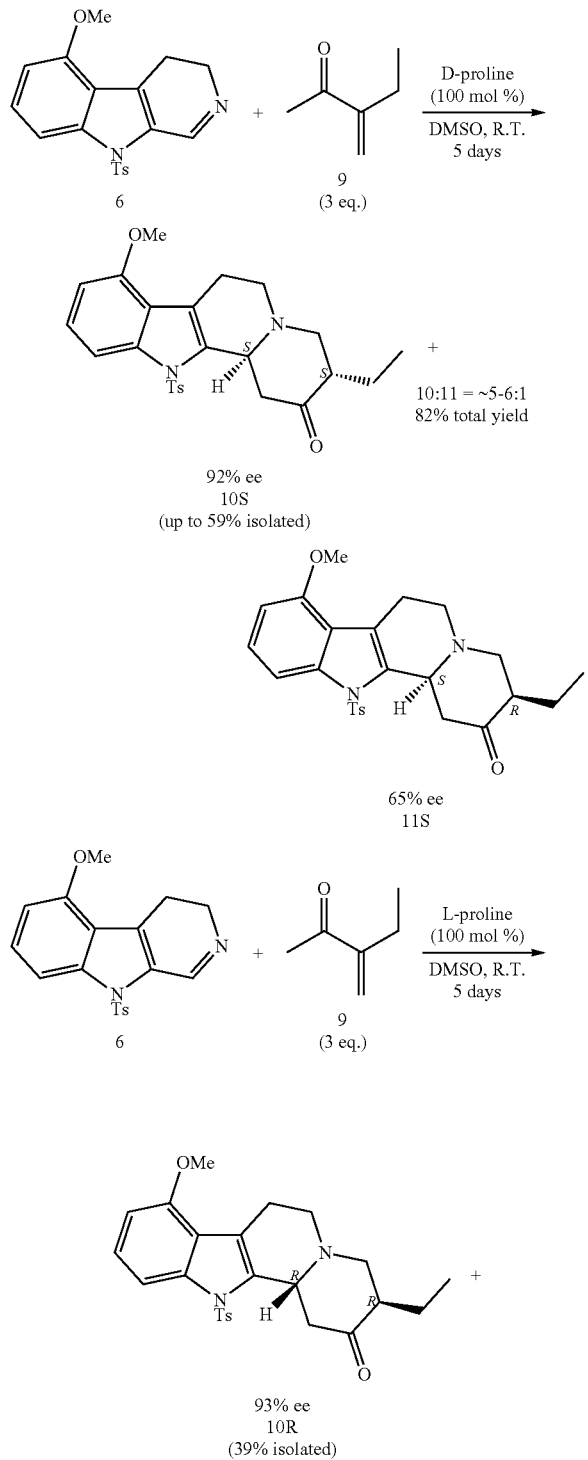

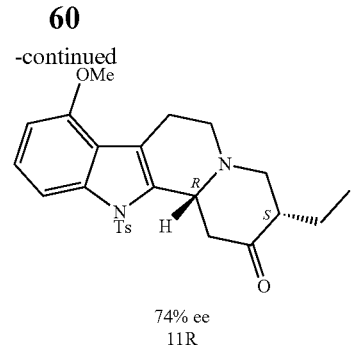

74% ee
11R

General Procedure for Preparation of 3-Ethyl-8-methoxy-12-tosyl-3,4,6,7,12,12b-hexahydroindolo[2,3-a]quinolizin-2 (1H)-ones (10 and 11)

Carboline 6 (1 equivalent), enone 9 (3 equivalents), and proline (1 equivalent, D-proline for 10/11S, L-proline for 10/11R) were dissolved in anhydrous DMSO (0.0200 M, based on 6), and the mixture was stirred until TLC indicated the disappearance of 6 (3-6 days). The reaction was then diluted with 4× its volume of water, made slightly basic with saturated aqueous NaHCO$_3$, and extracted with CH$_2$Cl$_2$ (3×). The combined organics were washed with saturated aqueous NaHCO$_3$ and brine, dried over Na$_2$SO$_4$, and concentrated to provide the crude product as a sticky brown solid or yellow foam (depending on quantity of residual DMSO). The ratio of diastereomers 10 and 11 in the crude product was determined by NMR (key peaks 4.54 ppm=10 and 4.14 ppm=11), and these were then separated by column chromatography (6:4 hexanes:EtOAc, 4 column volumes→1:1 hexanes:EtOAc, 2 column volumes). The enantiomeric excess of each product was determined by chiral HPLC (Daicel Chiralcel OD column, 8:2 hexanes:iPrOH+0.20% Et$_2$NH, 1 mL/min).

Note 1:
Some of the fractions contained a mixture of diastereomers and thus, running a second chromatography column allowed for higher isolated yields of product 10 if desired.

Note 2:
Early chromatographic fractions containing only compound 11 were invariably contaminated with an inseparable impurity. Due to the low ee of 11, this diastereomer was not used in the following steps and no further efforts were made to isolate pure samples.

Note 3:
Yield and diastereoselectivity were found to vary significantly in several trials, mostly dependent on the prior purification of carboline 6 (purification of 6 by column chromatography required for highest yield and selectivity for 10).

(3S,12bS)-3-Ethyl-8-methoxy-12-tosyl-3,4,6,7,12,12b-hexahydroindolo[2,3-a]quinolizin-2(1H)-one (10S)

The product was prepared according to the general procedure using D-proline and obtained as an amorphous, pale-yellow solid (40% [91% ee], 44% [92% ee], and 59% [2 columns, 95% ee] isolated in three individual trials). $[\alpha]^{25}_D$, =67.7 (CHCl$_3$); t$_R$=6.86 min (Daicel Chiralcel OD column, 8:2 hexanes:iPrOH+0.20% Et$_2$NH, 1 mL/min); $^1$H NMR (400 MHz, CDCl$_3$) δ 7.67 (d, J=8.3 Hz, 1H), 7.49 (d, J=8.3 Hz, 2H), 7.15 (t, J=8.2 Hz, 1H), 7.09 (d, J=8.1 Hz, 2H), 6.61 (d, J=8.0 Hz, 1H), 4.54 (d, J=10.7 Hz, 1H), 3.81 (s, 3H), 3.43 (dd, J=13.0, 6.2 Hz, 1H), 3.32-3.21 (m, 2H), 3.13 (dt, J=16.4, 3.9 Hz, 1H), 3.02-2.81 (m, 3H), 2.61-2.49 (m, 2H), 2.27 (s, 3H), 1.99-1.86 (m, 1H), 1.31-1.17 (m, 1H), 0.97 (t, J=7.5 Hz, 3H); $^{13}$C NMR (101 MHz, CDCl$_3$) δ 208.5, 154.2, 144.7, 138.9, 134.7, 134.3, 129.7, 126.6, 125.7, 120.1, 119.4, 108.8, 104.9, 59.9, 59.1, 55.5, 48.5, 45.9, 45.8, 24.9, 21.7, 19.5, 11.9; LRMS (APCI+) calcd. for $C_{25}H_{29}N_2O_4S^+$ [M+H]$^+$ 453.18, found 453.39.

(3R,12bR)-3-Ethyl-8-methoxy-12-tosyl-3,4,6,7,12, 12b-hexahydroindolo[2,3-a]quinolizin-2(10)-one (10R)

The product was prepared according to the general procedure using L-proline and obtained as an amorphous, pale-yellow solid (39% isolated, 93% ee) having spectral properties identical to the opposite enantiomer 10S. [α]$^{25}_D$=−66.8 (CHCl$_3$); T$_R$=8.93 min (Daicel Chiralcel OD column, 8:2 hexanes:iPrOH+0.20% Et$_2$NH, 1 mL/min).

(3R,12bS)-3-Ethyl-8-methoxy-12-tosyl-3,4,6,7,12, 12b-hexahydroindolo[2,3-a]quinolizin-2(1H)-one (11S)

The product was prepared according to the general procedure using D-proline and obtained as an amorphous, pale-yellow solid containing significant impurities (74% and 65% ee in two individual trials). t$_R$=6.43 min (Daicel Chiralcel OD column, 8:2 hexanes:iPrOH+0.20% Et$_2$NH, 1 mL/min); $^1$H NMR (500 MHz, CDCl$_3$) (Peak list excludes impurity peaks) δ 7.66 (d, J=8.3 Hz, 1H), 7.46 (d, J=8.2 Hz, 2H), 7.16 (t, J=8.2 Hz, 1H), 7.08 (d, J=8.1 Hz, 2H), 6.61 (d, J=8.1 Hz, 1H), 4.14 (d, J=8.5 Hz, 1H), 3.80 (s, 3H), 3.42 (dd, J=15.0, 2.4 Hz, 1H), 3.11 (dd, J=11.5, 5.6 Hz, 1H), 3.06-2.97 (m, 3H), 2.82 (d, J=17.1 Hz, 1H), 2.65-2.57 (m, 1H), 2.52-2.45 (m, 1H), 2.41 (br s, 1H), 2.29 (s, 3H), 1.89-1.79 (m, 1H), 1.69-1.61 (m, 1H), 0.94 (t, J=7.4 Hz, 3H); LRMS (ESI+) calcd. for $C_{25}H_{29}N_2O_4S^+$ [M+H]$^+$ 453.18, found 453.23.

(3S,12bR)-3-Ethyl-8-methoxy-12-tosyl-3,4,6,7,12, 12b-hexahydroindolo[2,3-a]quinolizin-2(1H)-one (11R)

The product was prepared according to the general procedure using L-proline and obtained as an amorphous, pale-yellow solid containing significant impurities (74% ee) and having spectral properties identical to the opposite enantiomer 11S. t$_R$=10.52 min (Daicel Chiralcel OD column, 8:2 hexanes:iPrOH+0.20% Et$_2$NH, 1 mL/min).

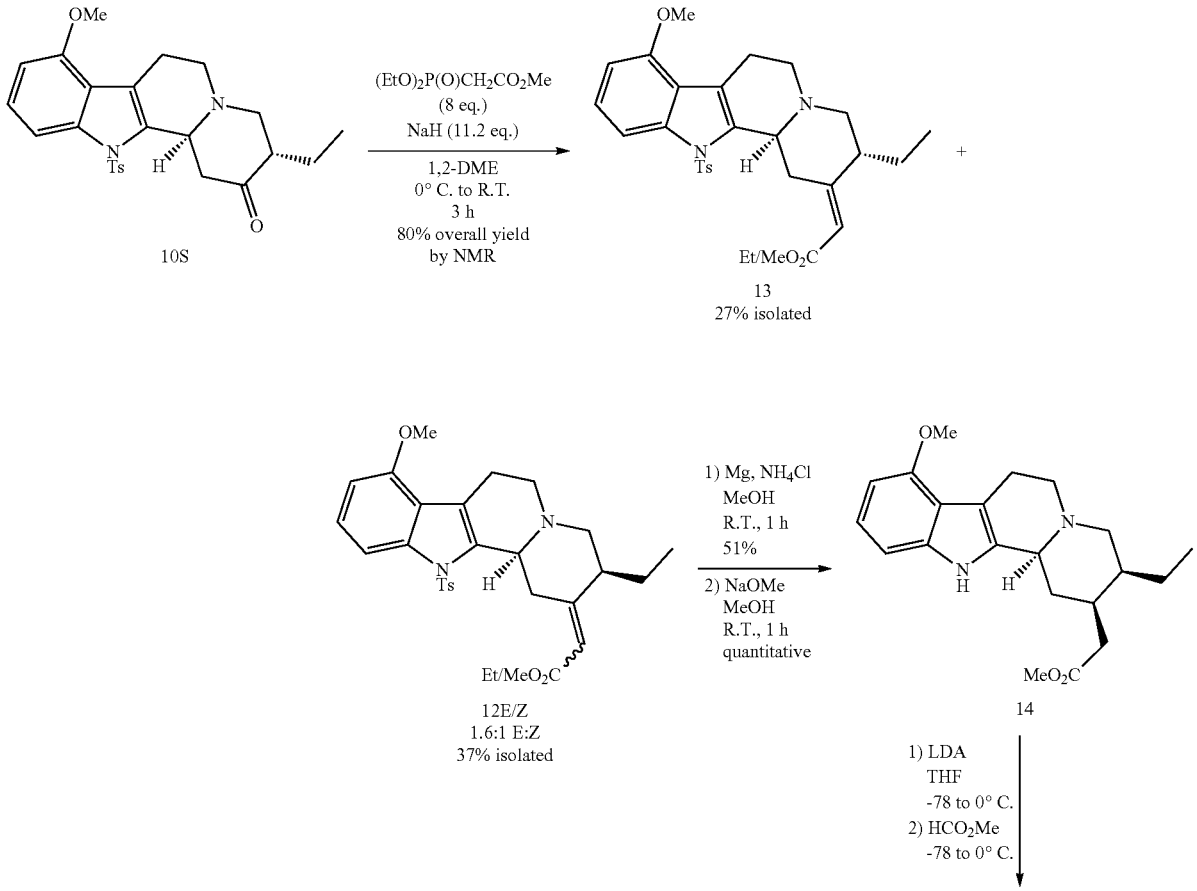

Scheme 6. Synthesis of mitragynine and (Z)-mitragynine.

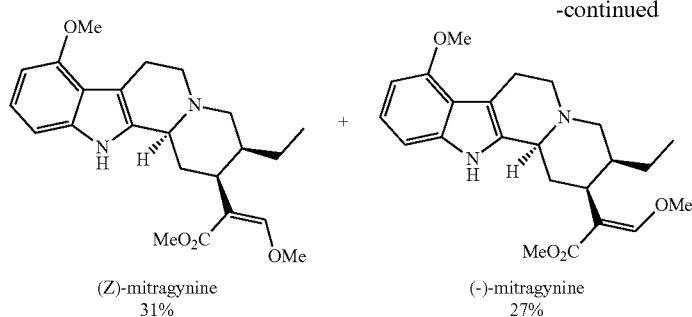
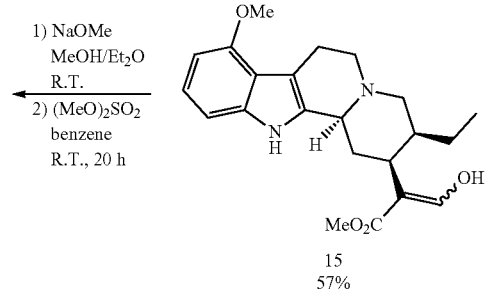

(Z)-mitragynine 31%  (-)-mitragynine 27%  15 57%

Methyl 2-((12bS)-3-ethyl-8-methoxy-12-tosyl-3,4,6,7,12,12b-hexahydroindolo[2,3-a]quinolizin-2(1H)-ylidene)acetates (12E, 12Z, 13)

To a suspension of NaH (596 mg of 60% in oil, 14.90 mmol) in anhydrous 1,2-dimethoxyethane (8.0 mL) was added methyl diethylphosphonoacetate (1.95 mL, 2.24 g, 10.64 mmol) dropwise over 5 min at 0° C., and the mixture was then stirred for 5 min. Ketone 10S (602 mg, 1.33 mmol) was then added all at once, and the resulting yellow mixture was allowed to warm to room temperature and stirred for 3 h. The reaction was quenched with water (50 mL) and extracted with $Et_2O$ (3×50 mL). The combined organics were washed with water (25 mL) and brine (25 mL), dried over $Na_2SO_4$, and concentrated to give a viscous yellow oil. This was purified by repeated column chromatography (Column 1: 20:1 $CH_2Cl_2$:$Et_2O$, 5 column volumes→9:1 $CH_2Cl_2$:$Et_2O$, 4 column volumes; Column 2: 8:2→7:3→6:4 hexanes:EtOAc, 2 column volumes each→0.1:1 hexanes:EtOAc, 4 column volumes) to provide a mixture of Z and E ene-esters with (3S, 12bS) stereochemistry, 12K and 12Z (254 mg, 1.6:1 E:Z, 27 mol % ethyl esters, 37% yield), and the E ene-ester with (3R, 12bS) stereochemistry, 13 (182 mg, 27 mol % ethyl ester, 27% yield), both as amorphous, pale-yellow solids.

Note 1:
If desired, 12K and 12Z may also be separated by column chromatography (order of elution on silica=12Z [least polar], 12E, 13 [most polar]), but this is unnecessary as both are converted to the same product following reduction (see preparation of 14 below).

Note 2:
The NMR peaks for the ethyl ester impurities of each product overlap, except for those peaks corresponding to the ethyl group itself.

Methyl (E)-2-((3S,12bS)-3-ethyl-8-methoxy-12-tosyl-3,4,6,7,12,12b-hexahydroindolo[2,3-a]quinolizin-2(1H)-ylidene)acetate (12E)

This product may be obtained as an amorphous, pale-yellow solid from the mixture of 12K and 12Z by additional chromatography, but is invariably contaminated with a quantity of the ethyl ester analog. $^1$H NMR (500 MHz, $CDCl_3$) δ 7.67 (d, J=8.3 Hz, 1H), 7.45 (d, J=7.7 Hz, 2H), 7.13 (t, J=8.2 Hz, 1H), 7.04 (d, J=7.6 Hz, 2H), 6.59 (d, J=8.0 Hz, 1H), 5.73 (s, 1H), 4.56 (d, J=13.3 Hz, 1H), 3.83-3.71 (m, 1H), 3.78 (s, 6H), 3.05-2.89 (m, 4H), 2.73 (d, J=16.0 Hz, 1H), 2.64-2.55 (m, 1H), 2.26 (s, 3H), 2.24-2.11 (m, 1H), 1.80-1.69 (m, 1H), 1.69-1.62 (m, 1H), 0.87 (t, J=7.4 Hz, 3H); ethyl ester peaks: 4.25 (q, J=7.1 Hz, 2H), 1.36 (t, J=7.1 Hz); $^{13}$C NMR (126 MHz, $CDCl_3$) δ 167.0, 159.8, 154.0, 144.3, 140.0, 135.7, 133.9, 129.2, 126.9, 125.4, 122.6, 120.8, 116.2, 109.7, 105.2, 61.2, 59.9, 55.4, 51.3, 50.7, 47.8, 33.5, 26.5, 25.7, 21.7, 12.4; LRMS (ESI+) calcd. for $C_{28}H_{33}N_2O_5S^+$ [M+H]$^+$ 509.21, found 509.30.

Methyl (Z)-2-((3S,12bS)-3-ethyl-8-methoxy-12-tosyl-3,4,6,7,12,12b-hexahydroindolo[2,3-a]quinolizin-2(1H)-ylidene)acetate (12Z)

This product may be obtained as an amorphous, pale-yellow solid from the mixture of 12Z and 12E by additional chromatography, but is invariably contaminated with a quantity of the ethyl ester analog. $^1$H NMR (500 MHz, $CDCl_3$) δ 7.68 (d, J=8.3 Hz, 1H), 7.44 (d, J=8.0 Hz, 2H), 7.15 (t, J=8.2 Hz, 1H), 7.05 (d, J=8.0 Hz, 2H), 6.60 (d, J=8.1 Hz, 1H), 5.91 (s, 1H), 3.85-3.79 (m, 1H), 3.78 (s, 3H), 3.75-3.70 (m, 1H), 3.70 (s, 3H), 3.17 (d, J=12.7 Hz, 1H), 3.04-2.91 (m, 3H), 2.85-2.79 (m, 1H), 2.73 (d, J=16.5 Hz, 1H), 2.60-2.52 (m, 1H), 2.44 (t, J=11.6 Hz, 1H), 2.27 (s, 3H), 1.78-1.66 (m, 2H), 0.92 (t, J=7.4 Hz, 3H); ethyl ester peaks: 4.19-4.11 (m, 2H), 1.28 (t, J=7.1 Hz); $^{13}$C NMR (126 MHz, $CDCl_3$) δ 167.3, 163.1, 154.1, 144.6, 139.9, 135.2, 133.6, 129.3, 126.9, 125.5, 122.9, 120.9, 115.4, 109.7, 105.4, 62.3, 59.1, 55.5, 50.9, 50.6, 40.3, 39.7, 26.3, 25.6, 21.7, 12.1; LRMS (ESI+) calcd. for $C_{28}H_{33}N_2O_5S^+$ [M+H]$^+$ 509.21, found 509.38.

Methyl (E)-2-((3R,12bS)-3-ethyl-8-methoxy-12-tosyl-3,4,6,7,12,12b-hexahydroindolo[2,3-a]quinolizin-2(1B)-ylidene)acetate (13)

Obtained as an amorphous, pale-yellow solid, invariably contaminated with a quantity of the ethyl ester analog. $^1$H NMR (500 MHz, $CDCl_3$) δ 7.68 (d, J=8.3 Hz, 1H), 7.50 (d, J=8.1 Hz, 2H), 7.14 (t, J=8.2 Hz, 1H), 7.08 (d, J=8.2 Hz, 2H), 6.60 (d, J=8.0 Hz, 1H), 5.67 (s, 1H), 4.45 (d, J=13.1 Hz, 1H), 4.34 (br d, J=7.3 Hz, 1H), 3.81 (s, 3H), 3.80 (s, 3H), 3.33 (dd, J=12.8, 4.4 Hz, 1H), 3.30-3.20 (br m, 1H), 3.10 (d, J=16.3 Hz, 1H), 2.96-2.85 (br m, 1H), 2.85-2.73 (br m, 2H), 2.41-2.32 (br m, 1H), 2.26 (s, 3H), 2.25-2.19 (m, 1H), 1.75-1.64 (m, 1H), 1.35-1.23 (m, 1H), 1.01 (t, J=7.4 Hz, 3H); ethyl ester peaks: 4.27 (q, J=7.2 Hz, 2H), 1.35 (t, J=7.1 Hz); $^{13}$C NMR (101 MHz, $CDCl_3$) δ 167.7, 154.2, 144.5, 138.9, 135.2, 134.9, 129.6, 126.7, 125.4, 120.1, 119.0, 112.9, 108.9, 104.8, 61.5, 59.8, 55.5, 51.5, 45.6, 40.9, 34.0, 24.7, 22.1, 21.7, 11.8; LRMS (ESI+) calcd. for $C_{28}H_{33}N_2O_5S^+$ [M+H]$^+$ 509.21, found 509.30.

Methyl 2-((2R,3S,12bS)-3-ethyl-8-methoxy-1,2,3,4,6,7,12,12b-octahydroindolo[2,3-a]quinolizin-2-yl)acetate (14)

To a solution of mixed ene-esters 12E and 12Z (248 mg, 1.6:1 E:Z, 27 mol % ethyl esters, 0.484 mmol) in anhydrous MeOH (11.6 mL) was added Mg turnings (235 mg, 9.68 mmol) and NH$_4$Cl (118 mg, 2.20 mmol), and the mixture was stirred vigorously for 1.33 h at room temperature (effervescence). The reaction was then quenched with saturated aqueous NH$_4$Cl (20 mL) and water (20 mL) and extracted with CH$_2$Cl$_2$ (3×20 mL). The combined organics were washed with saturated aqueous NaHCO$_3$ (20 mL) and brine (20 mL), dried over Na$_2$SO$_4$, and concentrated to give a pale, yellow-olive foam (167 mg). This material was purified by column chromatography (7:3 CH$_2$Cl$_2$:Et$_2$O) to provide compound 14 as a pale, yellow-green amorphous solid contaminated with the ethyl ester analog (88.5 mg, 23 mol; ethyl ester, 51% yield). A quantity of this mixed ester material (87.4 mg, 0.243 mmol) was dissolved in freshly prepared 1M sodium methoxide in MeOH (5.0 mL), and the solution was stirred for 1 h at room temperature. The reaction was then diluted with CH$_2$Cl$_2$ (50 mL), washed with water (2×25 mL) and brine (10 mL), dried over Na$_2$SO$_4$ and concentrated to provide pure methyl ester 14 as a pale, yellow-green amorphous solid (90.9 mg, quantitative for transesterification, 51% over 2 steps). $^1$H NMR (500 MHz, CDCl$_3$) δ 7.80 (br s, 1H), 7.00 (t, J=7.9 Hz, 1H), 6.89 (d, J=8.0 Hz, 1H), 6.46 (d, J=7.7 Hz, 1H), 3.88 (s, 3H), 3.73 (s, 3H), 3.24 (d, J=9.5 Hz, 1H), 3.15-3.06 (m, 1H), 3.03-2.89 (m, 3H), 2.57 (td, J=11.6, 4.2 Hz, 1H), 2.43-2.33 (m, 2H), 2.33-2.21 (m, 2H), 1.89 (d, J=12.6 Hz, 1H), 1.72-1.58 (m, 1H), 1.58-1.42 (m, 2H), 1.30-1.19 (m, 1H), 0.92 (t, J=7.3 Hz, 3H); $^{13}$C NMR (126 MHz, CDCl$_3$) δ 173.8, 154.6, 137.5, 133.4, 122.0, 117.7, 108.1, 104.4, 99.9, 60.0, 57.6, 55.4, 53.8, 51.7, 40.1, 38.1, 36.9, 32.0, 23.9, 18.3, 12.6; LRMS (APCI+) calcd. for C$_{21}$H$_{29}$N$_2$O$_3$$^+$ [M+H]$^+$ 357.22, found 356.64.

Methyl 2-((2S,3S,12bS)-3-ethyl-8-methoxy-1,2,3,4,6,7,12,12b-octahydroindolo[2,3-a]quinolizin-2-yl)-3-hydroxyacrylate (15)

To a solution of diisopropylamine (115 μL, 82.3 mg, 0.813 mmol, 99.95% redistilled grade) in anhydrous THF (1.7 mL, freshly distilled from Na/benzophenone) at −78° C. was added n-BuLi (2.5 M in hexanes, 325 μL, 0.813 mmol). The resulting solution was stirred at −78° C. for 5 min and then warmed to 0° C. and stirred for 30 min. The reaction was then cooled back to −78° C. and a solution of ester 14 (85.6 mg, 0.240 mmol) in anhydrous THF (1.7 mL, freshly distilled from Na/benzophenone) was added dropwise over 5 min. After stirring the orange solution for 1 h at −78° C., anhydrous methyl formate (1.69 mL, 1.65 g, 27.4 mmol, freshly distilled from P$_2$O$_5$) was added, and the mixture was warmed to 0° C. and stirred for 45 min. The reaction was then quenched with water (35 mL), made strongly basic with 10% aqueous NaOH (15 mL), and extracted with Et$_2$O (3×10 mL). The aqueous layer was then neutralized to pH 7 with 10% aqueous HCl and extracted with CH$_2$Cl$_2$ (4×25 mL). The Et$_2$O and CH$_2$Cl$_2$ extracts were combined, dried over Na$_2$SO$_4$, and concentrated to provide a viscous, yellow-orange oil (180 mg). This crude product was purified by column chromatography (9:1 CH$_2$Cl$_2$:Et$_2$O+2% Et$_3$N) to give a pale-yellow glass. This material was then dissolved in CH Cl$_z$(30 mL), washed with saturated aqueous NaHCO$_3$ (5 mL) and brine (5 mL), dried over Na$_2$SO$_4$, and concentrated to yield pure enol 15 as an amorphous, pale-yellow solid (52.7 mg, 57%). $^1$H NMR (500 MHz, CDCl$_3$) (spectrum extremely complex due to mixture of tautomers and E/Z enol) δ 11.76 (br s, 0.35H), 9.77-9.64 (m, 0.40H), 8.00-7.68 (m, 1.2H), 7.09-6.97 (m, 1.35H), 6.94-6.85 (m, 1.35H), 6.51-6.42 (m, 1H), 4.02-3.93 (m, 0.25H), 3.93-3.61 (m, 6H), 3.61-3.53 (m, 0.20H), 3.44-3.31 (m, 0.50H), 3.27-2.82 (m, 5H), 2.77-2.34 (m, 3H), 2.10-1.93 (m, 0.50H), 1.83-1.66 (m, 2H), 1.62-1.40 (m, 1.7H), 1.33-1.21 (m, 1H), 1.21-1.09 (m, 1H), 0.97-0.81 (m, 3H); $^{13}$C NMR (126 MHz, CDCl$_3$) (spectrum extremely complex due to mixture of tautomers and E/Z enol) δ 197.9, 196.9, 172.7, 171.6, 169.5, 169.0, 162.8, 161.4, 154.62, 154.57, 138.0, 137.4, 133.1, 132.7, 131.2, 122.9, 122.23, 122.17, 117.7, 117.6, 117.5, 116.8, 108.42, 108.35, 107.6, 106.8, 105.6, 104.44, 104.38, 100.1, 100.0, 62.4, 61.8, 60.9, 60.3, 60.1, 58.0, 57.6, 57.4, 56.0, 55.43, 55.39, 55.35, 53.6, 52.7, 52.6, 51.8, 51.23, 51.15, 46.2, 40.0, 39.6, 39.2, 38.4, 38.0, 37.8, 37.6, 33.9, 30.1, 29.8, 29.7, 25.2, 24.0, 22.3, 18.3, 18.2, 17.8, 12.8, 12.6, 12.2, 12.0; LRMS (APCI+) calcd. for C$_{22}$H$_{29}$N$_2$O$_4$$^+$ [M+H]$^+$ 385.21, found 384.50.

(−)-Mitragynine (synthetic) and (Z)-mitragynine

To enol 15 (50.4 mg, 0.131 mmol) was added anhydrous Et$_2$O (2.5 mL) followed by freshly prepared 1M sodium methoxide in anhydrous MeOH (131 μL, 0.131 mmol), and the resulting solution was concentrated to give a foamy, yellow-beige solid. This material (presumed Na enolate) was dissolved in anhydrous benzene (6.6 mL), a solution of 1M dimethyl sulfate in anhydrous benzene (131 μL, 0.131 mmol) was added, and the resulting yellow solution was stirred at room temperature for 16 h. Additional 1M dimethyl sulfate in benzene (19.7 μL, 0.0197 mmol) was then added and stirring was continued for a further 4 h. At this time, the reaction was diluted with Et$_2$O (50 mL) and washed with 5% aqueous NaOH (30 mL) and brine (30 mL), dried over Na$_2$SO$_4$, and concentrated to provide a foamy, yellow-tan solid (43 mg). This material was purified by preparative TLC (1 mm silica layer, 20×20 cm plate, 1:1 hexanes:EtOAc+2% Et$_3$N) to provide pure, fully synthetic, (−)-mitragynine (14.2 mg, 27%) and (Z)-mitragynine (16.0 mg, 31%), both as amorphous, pale-yellow solids.

(−)-Mitragynine

Fully synthetic mitragynine was obtained as an amorphous, pale-yellow solid (14.2 mg, 27%) having spectral properties identical to the natural product. $t_R$=8.36 min (Daicel Chiralcel OD column, 8:2 hexanes:iPrOH+0.20% Et$_2$NH, 1 mL/min).

(Z)-Mitragynine=methyl (Z)-2-((2S,3S,12bS)-3-ethyl-8-methoxy-1,2,3,4,6,7,12,12b-octahydroindolo[2,3-a]quinolizin-2-yl)-3-methoxyacrylate The Z-isomer of mitragynine was obtained as an amorphous, pale-yellow solid (16.0 mg, 31). $t_R$=8.69 min (Daicel Chiralcel OD column, 8:2 hexanes:iPrOH+0.20% Et$_2$NH, 1 mL/min); $^1$H NMR (500 MHz, CDCl$_3$) δ 7.84 (br s, 1H), 7.01 (t, J=7.9 Hz, 1H), 6.91 (d, J=8.1 Hz, 1H), 6.47 (d, J=7.8 Hz, 1H), 6.15 (s, 1H), 3.88 (s, 3H), 3.79 (s, 3H), 3.77 (s, 3H), 3.24 (dd, J=10.7, 1.5 Hz, 1H), 3.14-3.04 (m, 1H), 3.01 (dd, J=11.6, 2.1 Hz, 1H), 2.99-2.90 (m, 3H), 2.55 (td, J=11.4, 4.2 Hz, 1H), 2.47 (dd, J=11.5, 2.2 Hz, 1H), 1.75-1.59 (m, 3H), 1.59-1.48 (m, 1H), 1.28-1.17 (m, 1H), 0.86 (t, J=7.4 Hz, 3H); $^{13}$C NMR (126 MHz, CDCl$_3$) δ 167.4, 156.0, 154.7, 137.5, 133.3, 122.2, 117.7, 111.2, 108.5, 104.3, 100.0, 62.1, 60.7, 57.9, 55.4, 53.6, 51.6, 39.9, 39.1, 30.4, 24.1, 18.3, 12.8; LRMS (APCI+) calcd. for C$_{23}$H$_{31}$N$_2$O$_4$$^+$ [M+H]$^+$ 399.23, found 398.41.

Example 6. Preparation of (Z)-7—Hydroxymitragynine

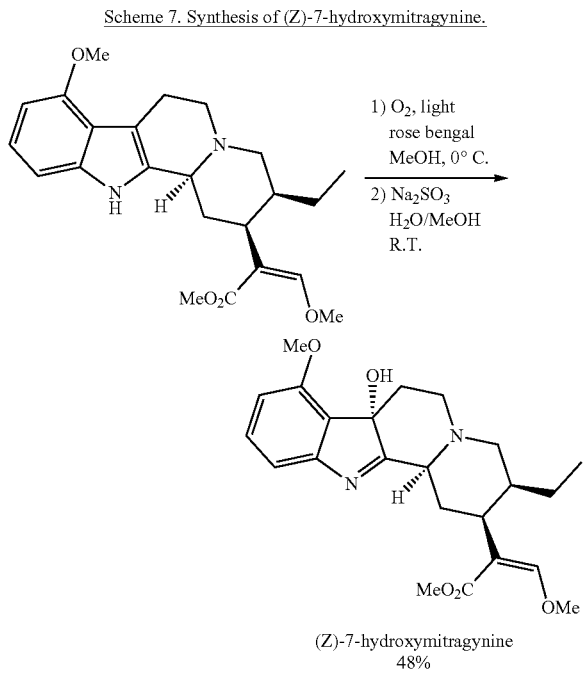

Scheme 7. Synthesis of (Z)-7-hydroxymitragynine.

(Z)-7-hydroxymitragynine
48%

(Z)-7-Hydroxymitragynine=methyl (Z)-2-((2S,3S, 7aS,12bS)-3-ethyl-7a-hydroxy-8-methoxy-1,2,3,4,6, 7,7a,12b-octahydroindolo[2,3-a]quinolizin-2-yl)-3-methoxyacrylate A solution of (Z)-mitragynine (4.2 mg, 0.0105 mmol) and rose bengal Na salt (0.5 mg) in MeOH (0.10 mL) was irradiated with a 500 W halogen work lamp at 0° C. under $O_2$ atmosphere for 1 h. Additional MeOH (0.30 mL) and a solution of $Na_2SO_3$ (30.0 mg, 0.240 mmol) in water (0.27 mL) were both added, and the pink mixture was stirred vigorously at room temperature until mass spectrometry indicated the disappearance of the hydroperoxide intermediate (2.5 h). The reaction was then diluted with water (1 mL) and extracted with $Et_2O$ (3×2 mL). The combined organics were dried over $Na_2SO_4$ and concentrated to provide a pale-pink solid (2.8 mg). This material was purified by preparative TLC (1 mm silica layer, 20×20 cm plate, 7:3 EtOAc:hexanes+2 $Et_3N$) to provide pure (Z)-7-hydroxymitragynine as a yellow glass (2.1 mg, 48%). $^1$H NMR (400 MHz, $CDCl_3$) δ 7.32 (t, J=8.0 Hz, 1H), 7.22 (d, J=7.6 Hz, 1H), 6.76 (d, J=8.3 Hz, 1H), 6.40 (s, 1H), 3.88 (s, 3H), 3.85 (s, 3H), 3.76 (s, 3H), 3.22 (dd, J=10.7, 2.3 Hz, 1H), 3.05 (dd, J=11.5, 2.0 Hz, 1H), 2.98-2.91 (m, 1H), 2.85-2.76 (m, 1H), 2.69-2.60 (m, 2H), 2.50 (dd, J=11.5, 2.2 Hz, 1H), 2.20 (s, 1H), 2.02 (dd, J=23.9, 13.0 Hz, 1H), 1.83 (d, J=12.9 Hz, 1H), 1.71-1.61 (m, 2H), 1.52-1.41 (m, 1H), 1.25-1.18 (m, 1H), 0.81 (t, J=7.4 Hz, 3H).

Example 7. Opioid Activity of Z-Isomers (Z)-Mitragynine and (Z)-7-hydroxymitragynine were tested for agonist and antagonist activity at the human MOR, KOR, and DOR using the bioluminescence resonance energy transfer (BRET) assays described in Example 4. The Z-isomers were found to be more selective for MOR over KOR and DOR compared to the natural E-isomers (Table 2).

TABLE 2

Figure 2:
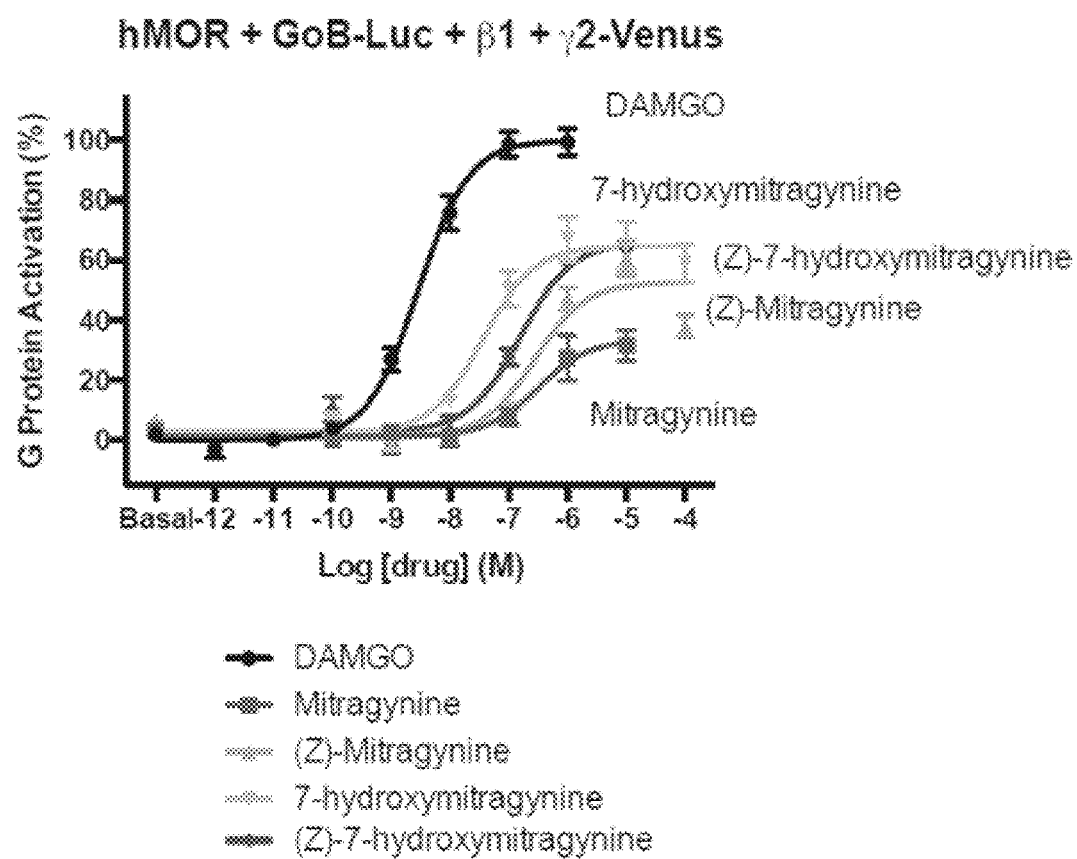
FIG. 2: Agonist activity of Z-isomers compared to E-isomers at human MOR; positive control=DAMGO.
Figure 3:
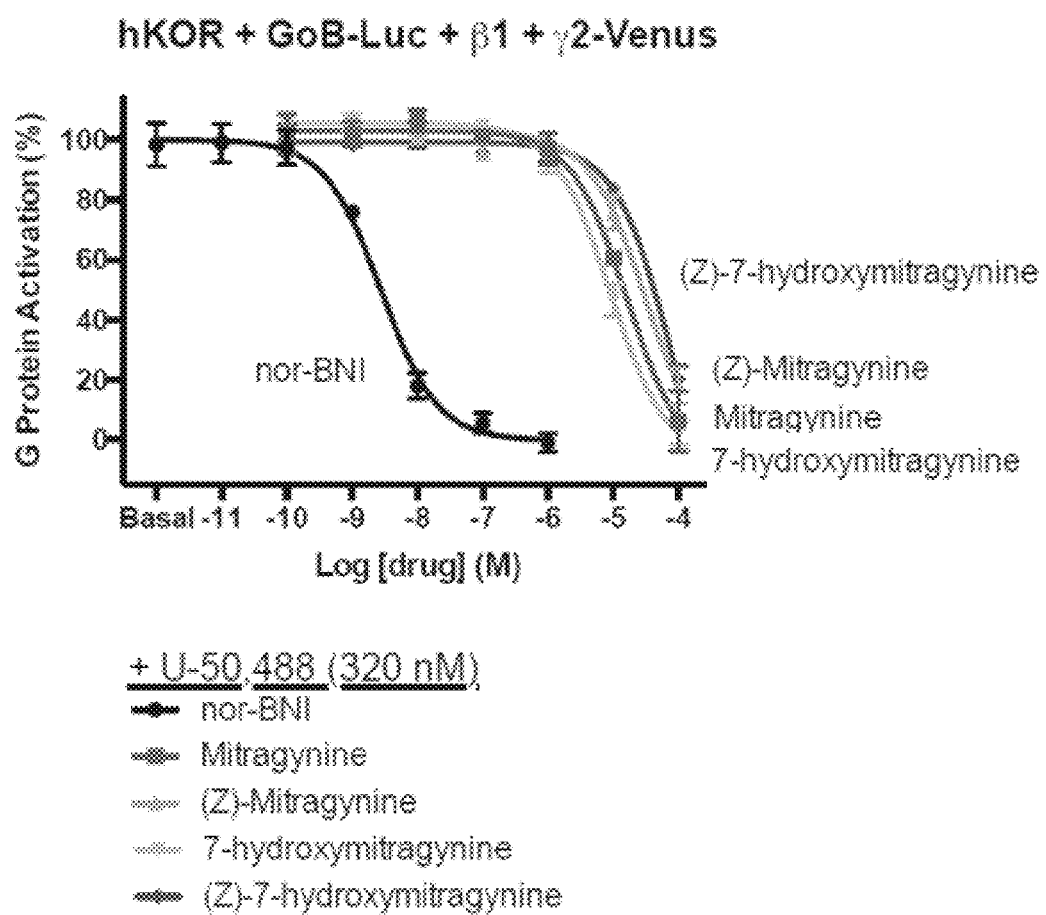
FIG. 3: Antagonist activity of Z-isomers compared to E-isomers at human KOR; competing agonist=U-50,488 (320 nM); positive control=nor-BNI.
Figure 4:
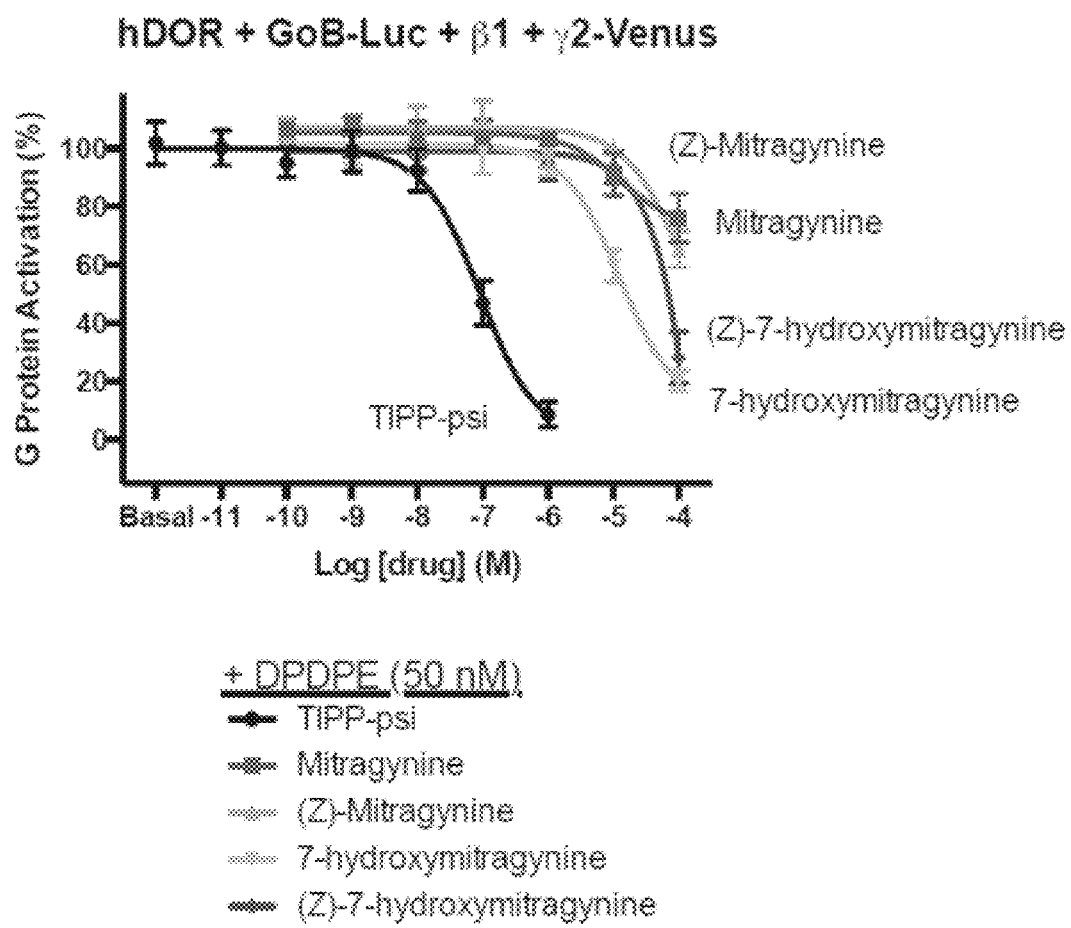
FIG. 4: Antagonist activity of Z-isomers compared to E-isomers at human DOR; competing agonist=DPDPE (50 nM); positive control=TIPP-psi.

Functional activity of Z-isomers versus E-isomers at human MOR, KOR, and DOR (FIGS. 2-4). Agonist activity is indicated by $EC_{50}$ values with $E_{max}$ in parentheses. Antagonist activity is indicated by $IC_{50}$ values for the inhibition of the corresponding reference agonist at 5x its $EC_{50}$ concentration. In some cases, $pA_2$ values (an estimate of Ki) obtained from Schild analysis are also provided for antagonist activity. Where indicated, error represents ±SEM of 2 or more independent trials.

| Compound | Structure | Human MOR | Human KOR | Human DOR |
|---|---|---|---|---|
| mitragynine | (structure) | $EC_{50}$ = 339 ± 178 nM (34%) | Antagonist $IC_{50}$ = 8.5 ± 7.6 μM (Schild $pA_2$ = 1.4 ± 0.4 μM) | Antagonist $IC_{50}$ = >50 μM (partial) |

TABLE 2-continued

Functional activity of Z-isomers versus E-isomers at human MOR, KOR, and DOR (FIGS. 2-4). Agonist activity is indicated by $EC_{50}$ values with $E_{max}$ in parentheses. Antagonist activity is indicated by $IC_{50}$ values for the inhibition of the corresponding reference agonist at 5x its $EC_{50}$ concentration. In some cases, $pA_2$ values (an estimate of Ki) obtained from Schild analysis are also provided for antagonist activity. Where indicated, error represents ±SEM of 2 or more independent trials.

| Compound | Structure | Human MOR | Human KOR | Human DOR |
| --- | --- | --- | --- | --- |
| (Z)-mitragynine | 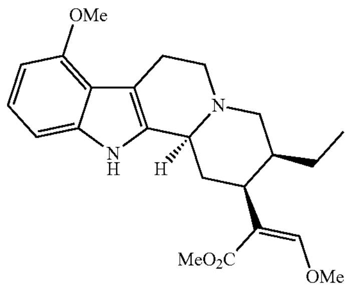 [SMILES: CC[C@@H]1CN2CCc3c([nH]c4cccc(OC)c34)[C@@H]2C[C@@H]1/C(=C/OC)C(=O)OC] | $EC_{50} = 219 \pm 71$ nM (38%) | Antagonist $IC_{50} = 42 \pm 15$ μM | Antagonist $IC_{50} = >100$ μM (partial) |
| 7-hydroxymitragynine | 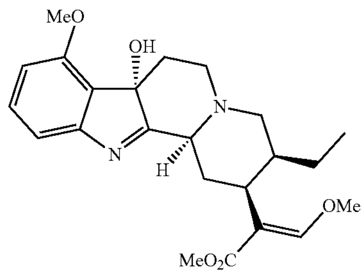 | $EC_{50} = 34.5 \pm 4.5$ nM (60%) | Antagonist $IC_{50} = 7.9 \pm 3.7$ μM (Schild $pA_2 = 490 \pm 131$ nM) | Antagonist $IC_{50} = 15.6 \pm 9.1$ μM |
| (Z)-7-hydroxymitragynine | 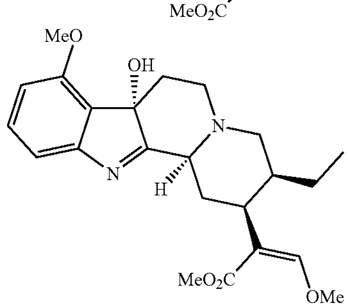 | $EC_{50} = 156 \pm 11$ nM (64%) | Antagonist $IC_{50} = >50$ μM | Antagonist $IC_{50} = >50$ μM |

Example 8S. Additional Photooxidation Methods

The photooxidation of mitragynine or related *Mitragyna* alkaloids may be carried out in the presence of other photosensitizing dyes, which enhance production of singlet oxygen. In such case, the rose bengal used in Examples 2 and 6 is replaced by the alternative dye and the mixture is irradiated with light in the presence of oxygen. Non-limiting examples of photosensitizing dyes include those listed in Table 3.

TABLE 3

Examples of photosensitizing dyes.

| Dye and Structure (if available) | Notes |
| --- | --- |
| Methylene Blue | |
| New Methylene Blue | Ragás et al. *Molecules* 2013, 18, 2712-2725. |

TABLE 3-continued

Examples of photosensitizing dyes.

| Dye and Structure (if available) | Notes |
|---|---|
| Porphyrins | |
| Chlorophyll | |
| aminolevulinic acid (ALA) | Precursor of photosensitizer (phorphyrins) Used in photodynamic therapy |
| Silicon Phthalocyanine Pc 4 | Used in photodynamic therapy |
| Temoporfin | Used in photodynamic therapy Aka Foscan |

TABLE 3-continued
Examples of photosensitizing dyes.
| Dye and Structure (if available) | Notes |
|---|---|
| Talaporfin 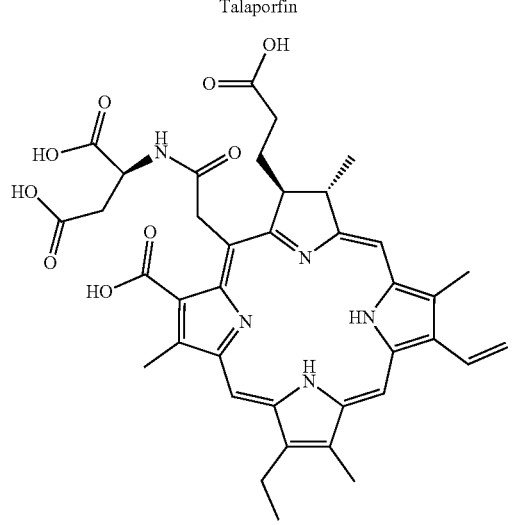 [SMILES: C=Cc1c(C)c2cc3nc(c(CC(=O)N[C@@H](CC(=O)O)C(=O)O)c4nc(cc5[nH]c(cc1[nH]2)c(C)c5CC)C(C)=C4C(=O)O)[C@@H](CCC(=O)O)[C@@H]3C] | Used in photodynamic therapy<br>Aka Laserphyrin |
| Allumera | Used in photodynamic therapy |
| Photofrin 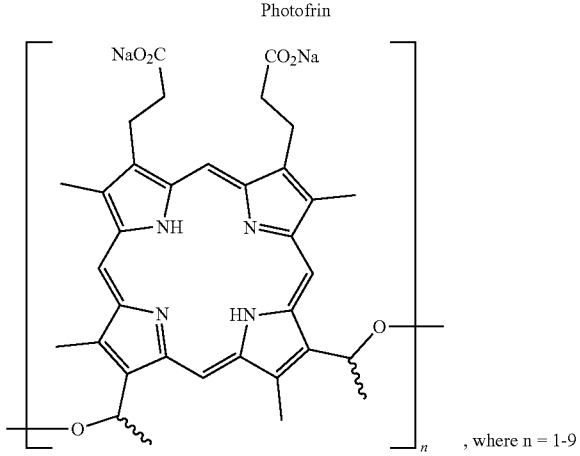, where n = 1-9 | Used in photodynamic therapy |

TABLE 3-continued

Examples of photosensitizing dyes.

| Dye and Structure (if available) | Notes |
| --- | --- |
| Visudyne | Used in photodynamic therapy |
| Protoporphyrin IX | Used in photodynamic therapy |
| Levulan | Active ingredient is ALA<br>Used in photodynamic therapy |
| Metvix | Methyl aminolevulinate<br>Used in photodynamic therapy |

TABLE 3-continued
Examples of photosensitizing dyes.
| Dye and Structure (if available) | Notes |
| --- | --- |
| Hervix 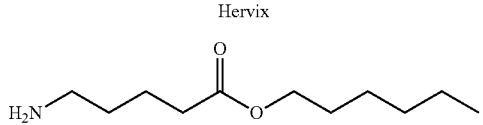 | Used in photodynamic therapy<br>Aka Cysview |
| Benzvix 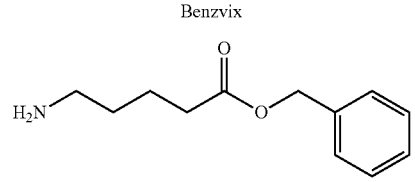 [SMILES: NCCCCC(=O)OCc1ccccc1] | Used in photodynamic therapy |
| Antrin 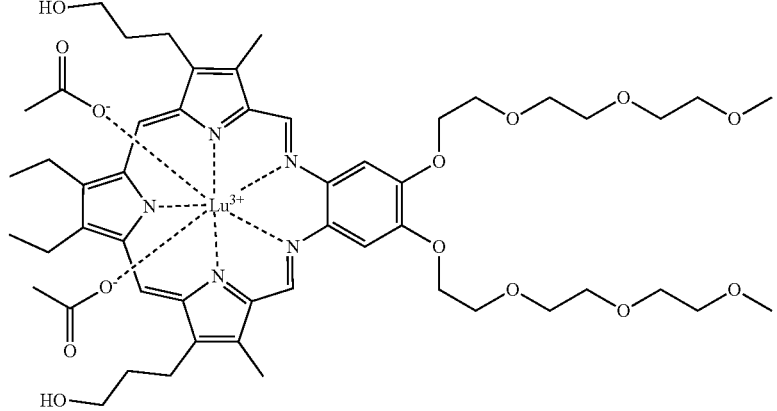 | Used in photodynamic therapy |
| Photochlor 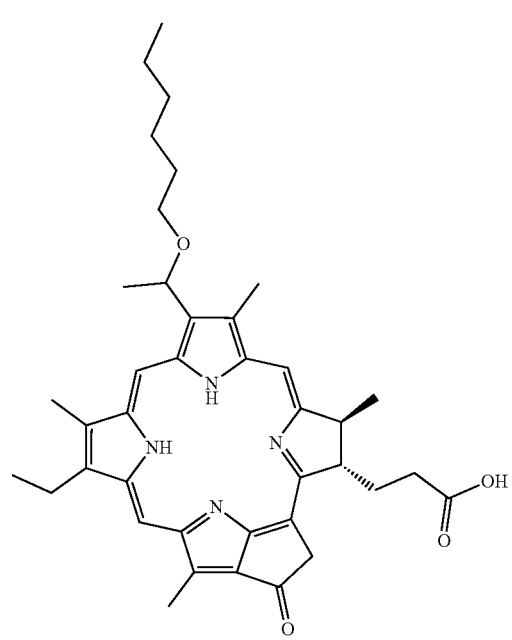 | Used in photodynamic therapy |

TABLE 3-continued

| Examples of photosensitizing dyes. | |
|---|---|
| Dye and Structure (if available) | Notes |
| Photosens | mixture of sulfonated aluminium phthalocyanines with various degrees of sulfonation Used in photodynamic therapy |
| Photrex | Used in photodynamic therapy |
| Lumacan | Used in photodynamic therapy |
| Cevira | Active ingredient hexylaminolevulinate Used in photodynamic therapy |
| Visonac | Used in photodynamic therapy |
| BF-200 ALA | Used in photodynamic therapy |
| Amphinex | Used in photodynamic therapy |
| Azadipyrromethenes 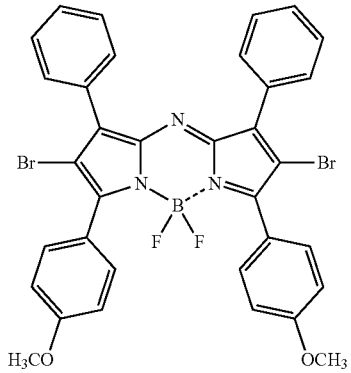 | Used in photodynamic therapy |
| zinc tetramethyltetrapyridino[3,4-b:39,49-g:30,40-1:3-,4-q]porphyrazinium salt | Ragás et al. *Molecules* 2013, 18, 2712-2725. |
| ACS268 | Ragás et al. *Molecules* 2013, 18, 2712-2725. |
| BODIPY Dimer and Monomer | Zhang et al. *J. Phys. Chem.* 2013, 117, 9050-9055. |
| Phenalenone | Kochevar et al. *Meth. Enzymol*, 2000, 319, 20. |
| Sensitizer Blue ™ | From Ursa Bioscience |
| Methuselah Green Carboxy ™ | From Ursa Bioscience |
| Erythrosin B 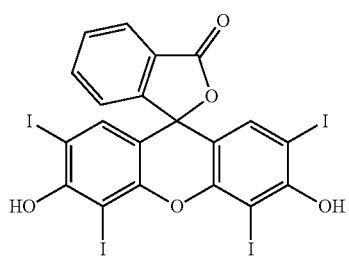 | From Ursa Bioscience |

TABLE 3-continued

Examples of photosensitizing dyes.

| Dye and Structure (if available) | Notes |
|---|---|
| Erythrosin | Red No. 3<br>Andrasik, S. J. 2007. |
| 9,10-Diphenyl-anthracene | Andrasik, S. J. 2007. |
| MTPP (meso-tetraphenylporphyrin) | M = Zn or Pd<br>Andrasik, S. J. 2007. |

TABLE 3-continued

Examples of photosensitizing dyes.

| Dye and Structure (if available) | Notes |
|---|---|
| MTPTNP (meso-tetraphenyltetranaphthoporphyrin) | M = Zn or Pd<br>Andrasik, S. J. 2007. |
| MTPTBP (meso-tetraphenyltetrabenzoporphyrin) | M = Zn or Pd<br>Andrasik, S. J. 2007. |
| metallophthalocyanine | Andrasik, S. J. 2007. |

TABLE 3-continued
Examples of photosensitizing dyes.
| Dye and Structure (if available) | Notes |
|---|---|
| metallotexaphyrin 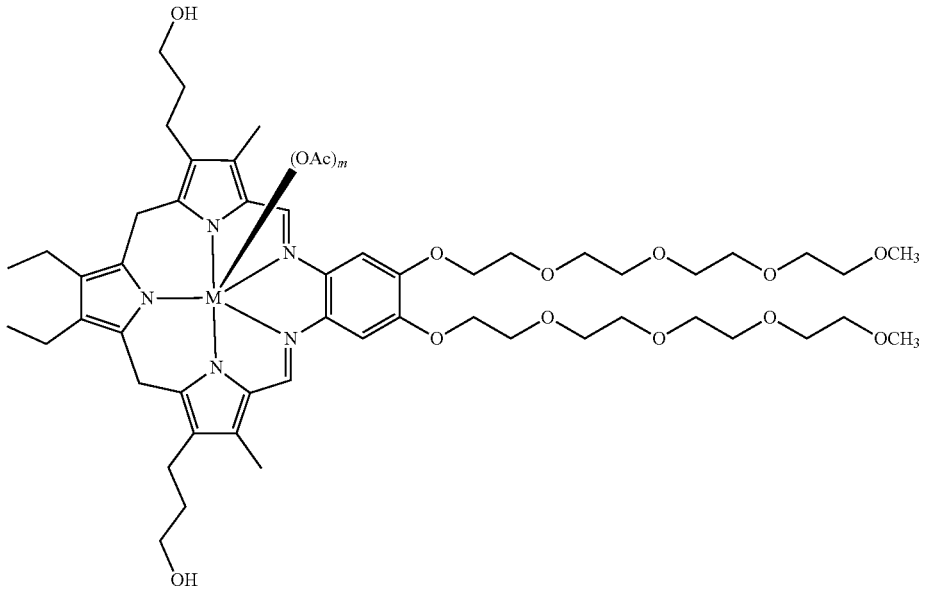 | Andrasik, S. J. 2007. |
| 5,6,11,12-Tetraphenyl-naphthacene 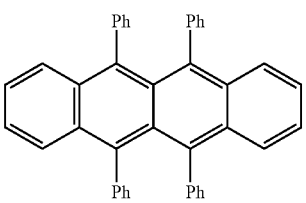 | Andrasik, S. J. 2007. |
| Naphthalene 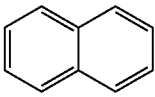 | Andrasik, S. J. 2007. |
| Biphenyl 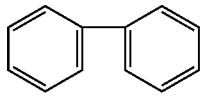 | Andrasik, S. J. 2007. |
| Fluorescein 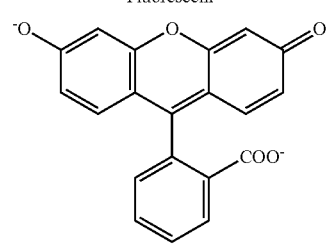 | Andrasik, S. J. 2007. |

TABLE 3-continued

Examples of photosensitizing dyes.

| Dye and Structure (if available) | Notes |
| --- | --- |
| Eosin Blue | Andrasik, S. J. 2007. |
| Acridine | Andrasik, S. J. 2007. |
| 5-(4-diphenylaminostilbene), 15-(2,6-dichlorophenyl)-21H,23H-porphine | Andrasik, S. J. 2007. |
| 5-phenyl, 15-(2,6-dichlorophenyl)-21H,23H-porphine | Andrasik, S. J. 2007. |

TABLE 3-continued
Examples of photosensitizing dyes.
| Dye and Structure (if available) | Notes |
|---|---|
| 5,10,15,20-tetraphenyl-21H,23H-porphine 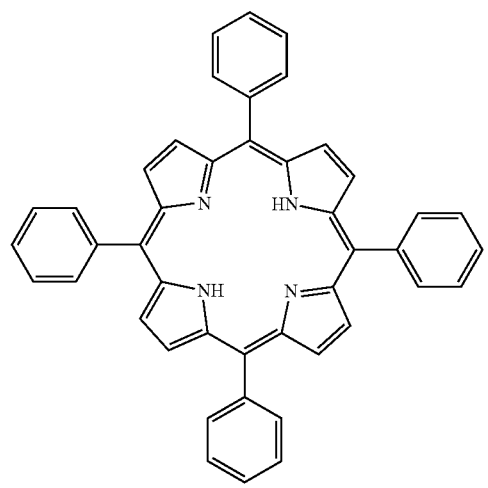 | Andrasik, S. J. 2007. |
| Octakis (4-R phenyl)-tetraazoporphine where R = NO$_2$ or Br 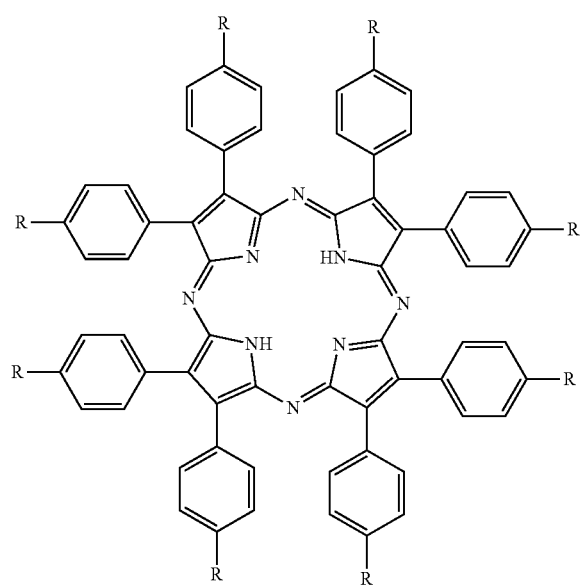 | Andrasik, S. J. 2007. |

TABLE 3-continued

Examples of photosensitizing dyes.

| Dye and Structure (if available) | Notes |
|---|---|
| 2PA-FRET based ¹O₂ sensitizer | Andrasik, S. J. 2007. |
| Difuranonaphthalene 2PA ¹O₂ sensitizer | Andrasik, S. J. 2007. |

TABLE 3-continued
Examples of photosensitizing dyes.
| Dye and Structure (if available) | Notes |
|---|---|
| 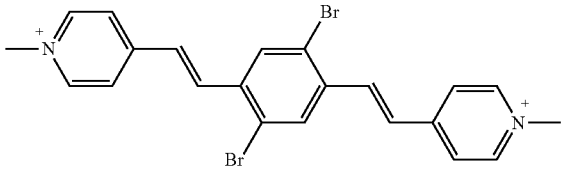 | Water soluble<br>Andrasik, S. J. 2007. |
| 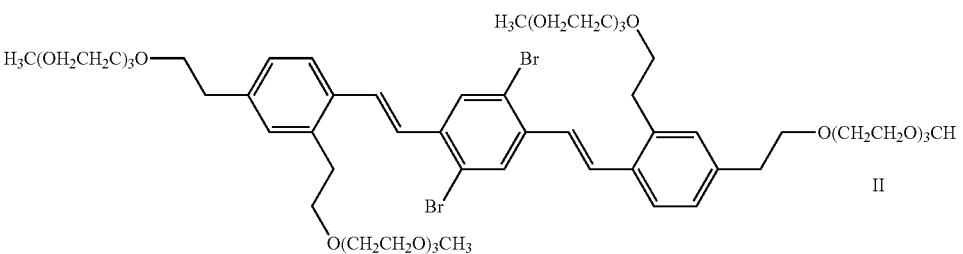 | Water soluble<br>Andrasik, S. J. 2007. |
| 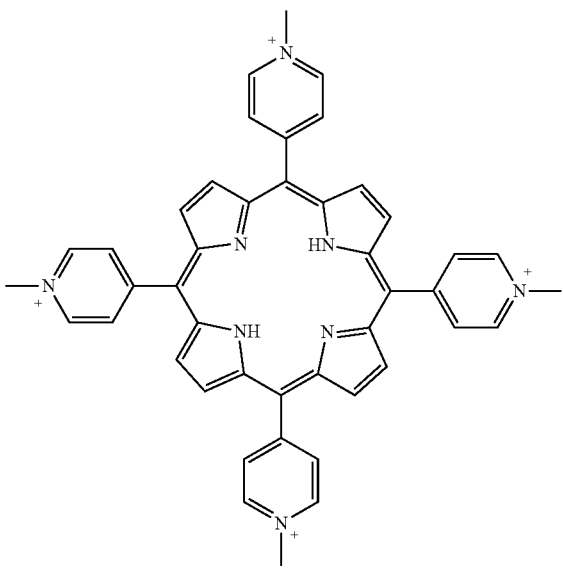 | Water soluble<br>Andrasik, S. J. 2007. |
| 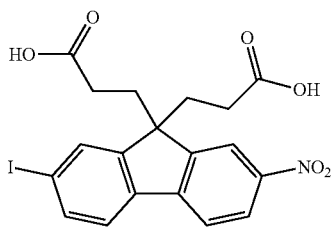 [SMILES: O=C(O)CCC1(CCC(=O)O)c2cc(I)ccc2-c2ccc([N+](=O)[O-])cc21] | Andrasik, S. J. 2007. |
| 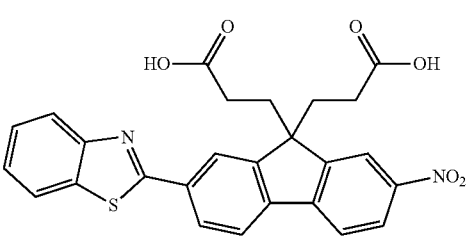 [SMILES: O=C(O)CCC1(CCC(=O)O)c2cc(-c3nc4ccccc4s3)ccc2-c2ccc([N+](=O)[O-])cc21] | Andrasik, S. J. 2007. |

TABLE 3-continued

Examples of photosensitizing dyes.

| Dye and Structure (if available) | Notes |
|---|---|
| 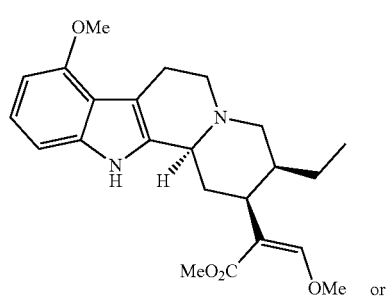 | Andrasik, S. J. 2007. |
| 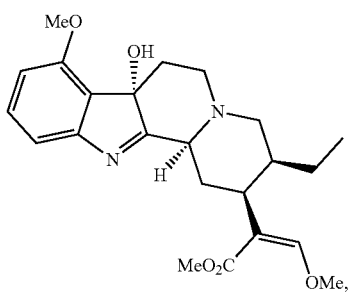 | Andrasik, S. J. 2007. |

Example 9. Administration of MOR Agonists

An amount of any one of the following compounds:

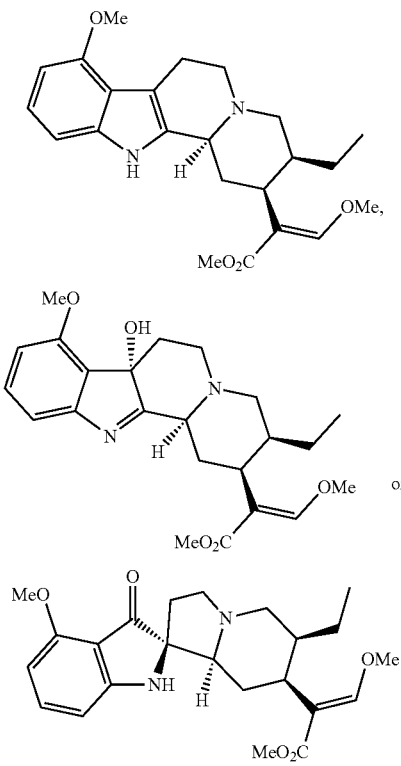

is administered to a subject afflicted with a depressive disorder, an anxiety disorder, or a mood disorder. The amount of the compound is effective to treat the subject.

An amount of any one of the following compounds:

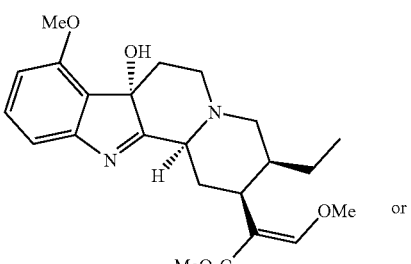

is administered to a subject afflicted with pain. The amount of the compound is effective to treat the subject.

An amount of any one of the following compounds:

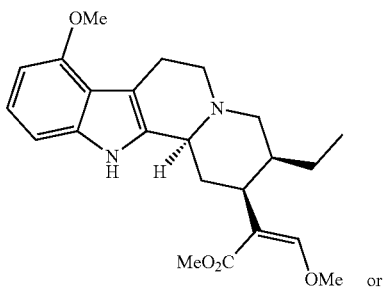

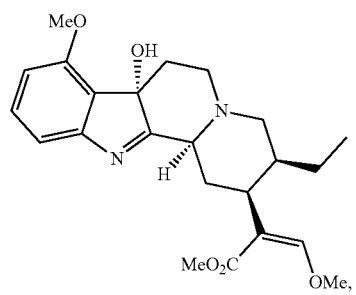

is administered to a subject afflicted with a mood or depressive disorder. The amount of the compound is effective to treat the subject.

An amount of any one of the following compounds:

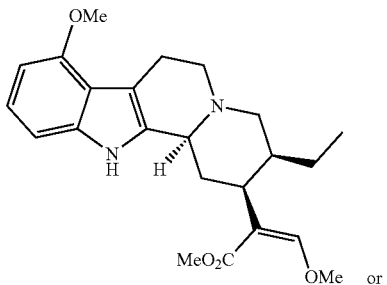

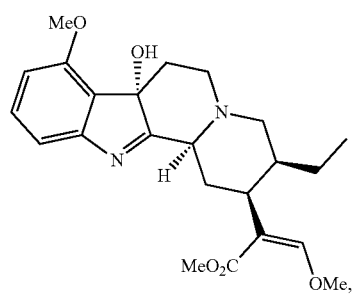

is administered to a subject afflicted with an anxiety disorder. The amount of the compound is effective to treat the subject.

An amount of any one of the following compounds:

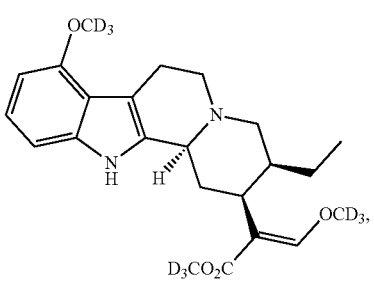

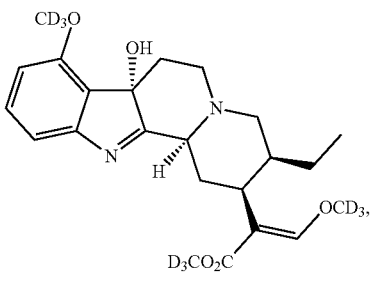

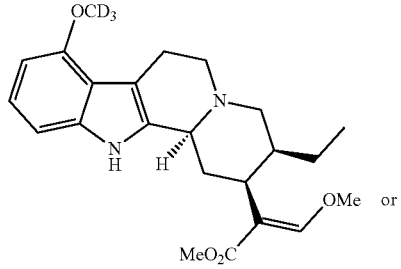

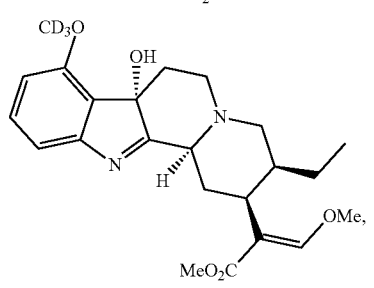

is administered to a subject afflicted with pain. The amount of the compound is effective to treat the subject.

An amount of any one of the following compounds:

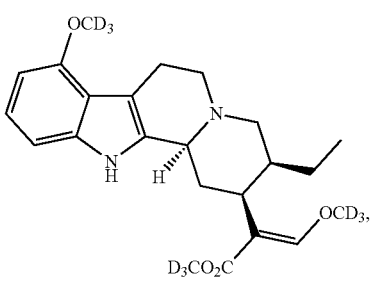

-continued

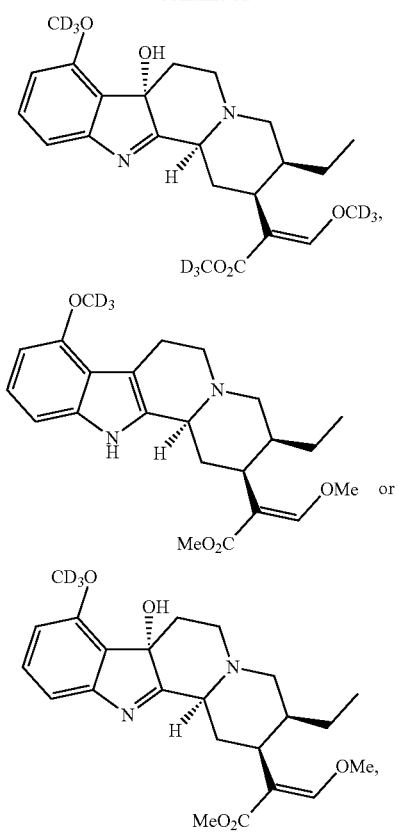

is administered to a subject afflicted with a mood or depressive disorder. The amount of the compound is effective to treat the subject.

An amount of any one of the following compounds:

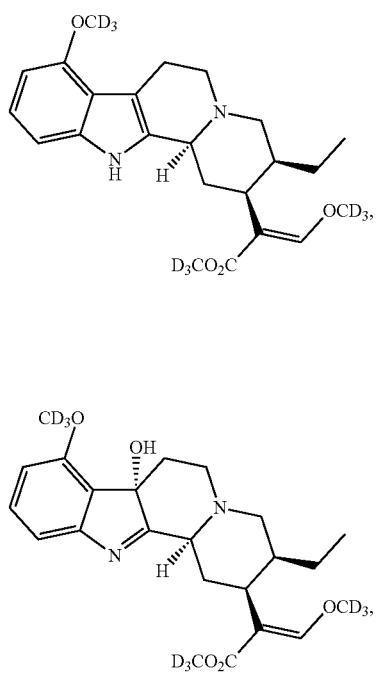

-continued

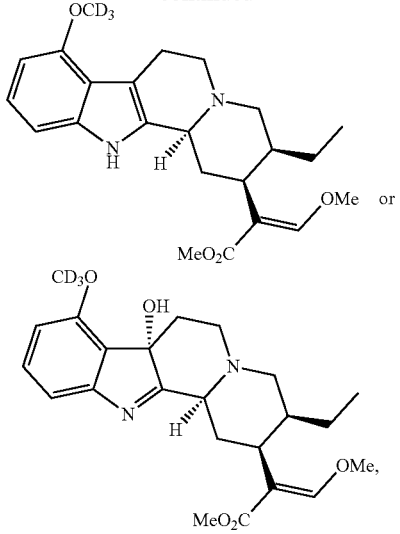

is administered to a subject afflicted with an anxiety disorder. The amount of the compound is effective to treat the subject.

An amount of any one of the following compounds:

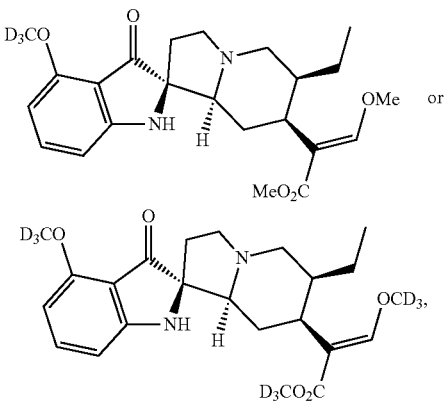

is administered to a subject afflicted with pain. The amount of the compound is effective to treat the subject.

An amount of any one of the following compounds:

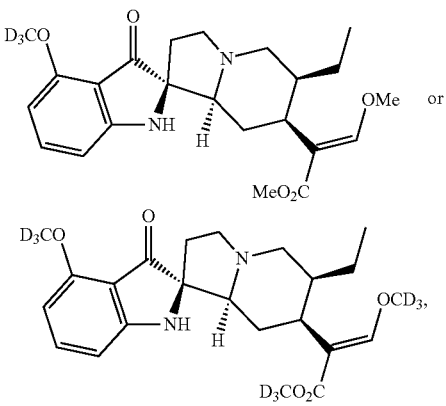

is administered to a subject afflicted with a mood or depressive disorder. The amount of the compound is effective to treat the subject.

An amount of any one of the following compounds:

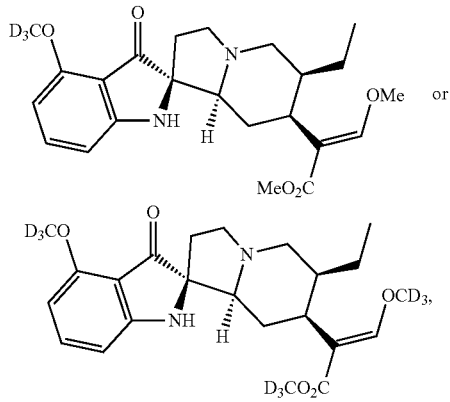

is administered to a subject afflicted with an anxiety disorder. The amount of the compound is effective to treat the subject.

Example 10. Combinations with NMDA Receptor Antagonists

Antagonists of the N-methyl-D-aspartate receptor (NMDAR) are known to potentiate the beneficial effects of opioid receptor agonists in the treatment of pain and to prevent the development of tolerance to those effects (Trujillo, K. A. et al. 1994; Mao, J. et al. 1996). NMDAR antagonists are also known to be effective in the treatment of depression (Murrough, J. W. et al. 2013). Therefore, pharmaceutical compositions of the compounds disclosed herein, combined with NMDAR antagonists, may be useful in the treatment of pain, anxiety disorders or mood disorders with increased efficacy and/or slower development of tolerance. Alternatively, the opioid modulator and NMDAR antagonist may be dosed separately, as a novel method for treating pain, anxiety disorders or mood disorders.

Non-Limiting Examples of MDA Receptor Antagonists:

Dextromorphinans—dextromethorphan, dextrorphan, dextrallorphan

Adamantanes—memantine, amantadine, rimantadine, nitromemantine (YQW-36)

Arylcyclohexylamines—ketamine (and its analogs, e.g. tiletamine), phencyclidine (and its analogs, e.g. tenocyclidine, eticyclidine, rolicyclidine), methoxetamine (and its analogs), gacyclidine (GK-11);

Miscellaneous—neramexane, lanicemine (AZD6765), diphenidine, dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (formerly MK-0657), atomoxetine, LY-235959, CGP 61594, CGP 37849, CGP 40116 (active enantiomer of CG 37849), LY-233536, PEAQX (NVP-AAM077), ibogaine, noribogaine, Ro 25-6981, GW468816, EVT-101, indantadol, perzinfotel (EAA-090), SSR240600, 2-MDP (U-23807A), AP-7

Example 11. Combinations with NMDA Receptor Partial Agonists

Weak partial agonists of NMDAR are also known (Moskal, J. R. et al. 2005), and may be expected to produce beneficial or synergistic effects similar to an antagonist when intrinsic glutamate signaling activity is high or overactivated. Therefore, pharmaceutical compositions of the novel compounds disclosed herein, combined with NMDAR partial agonists, may be useful in the treatment of pain, anxiety disorders or mood disorders with increased efficacy and/or slower development of tolerance. Alternatively, the opioid modulator and NMDAR partial agonist may be dosed separately, as a novel method for treating pain, anxiety disorders or mood disorders.

Non-Limiting Examples of NMDA Receptor Partial Agonists:

NRX-1074, rapastinel (GLYX-13)

Example 12. Combinations with Neurokinin 1 Receptor Antagonists

Antagonists of the neurokinin 1 receptor (NK-1) are known to modulate the effects of opioid agonists, specifically in reward and self-administration protocols. More specifically, NK-1 antagonists attenuate opioid reward and self-administration in animal models (Robinson, J. E. et al. 2012). NK-1 antagonists are also known to be effective in the treatment of depression (Kramer, M. S. et al. 2004). Therefore, pharmaceutical compositions of the novel compounds disclosed herein, combined with NK-1 antagonists, may be useful in the treatment of pain, anxiety disorders or mood disorders with increased efficacy and/or less potential for abuse. Alternatively, the opioid modulator and NK-1 antagonist may be dosed separately, as a novel method for treating pain, anxiety disorders or mood disorders.

Non-Limiting Examples of Neurokinin 1 Receptor Antagonists:

aprepitant, fosaprepitant, casopitant, maropitant, vestipitant, vofopitant, lanepitant, orvepitant, ezlopitant, netupitant, rolapitant, L-733060, L-703606, L-759274, L-822429, L-760735, L-741671, L-742694, L-732138, CP-122721, RPR-100893, CP-96345, CP-99994, TAK-637, T-2328, CJ-11974, RP 67580, NKP608, VPD-737, GR 205171, LY686017, AV608, SR140333B, SSR240600C, FK 888, GR 82334

Example 13. Combinations with Neurokinin 2 Receptor Antagonists

Antagonists of the neurokinin 2 receptor (NK-2) are known to show antidepressant effects and to synergize with tricyclic antidepressants (Overstreet, D. H. et al. 2010). Therefore, pharmaceutical compositions of the novel compounds disclosed herein, combined with NK-2 antagonists, may be useful in the treatment of anxiety disorders or mood disorders with increased efficacy. Alternatively, the opioid modulator and NK-2 antagonist may be dosed separately, as a novel method for treating anxiety disorders or a mood disorders.

Non-Limiting Examples of Neurokinin 2 Receptor Antagonists:

saredutant, ibodutant, nepadutant, GR-159897, MEN-10376

Example 14. Combinations with Neurokinin 3 Receptor Antagonists

Antagonists of the neurokinin 3 receptor (NK-3) are known to show antidepressant effects (Salome, et al. 2006). Further, the actions of NK-3 modulators show a dependency on the opioid receptor system (Panocka, I. et al. 2001). Therefore, pharmaceutical compositions of the novel compounds disclosed herein, combined with NK-3 antagonists, may be useful in the treatment of anxiety disorders or mood disorders with increased efficacy. Alternatively, the opioid modulator and NK-3 antagonist may be dosed separately, as a novel method for treating anxiety disorders or mood disorders.

Non-Limiting Examples of Neurokinin 3 Receptor Antagonists:

osanetant, talnetant, SB-222200, SB-218795

Example 15. Combinations with DOR Agonists

DOR Agonists have also been shown to elicit antidepressant and anxiolytic effects (Saitoh, A. et al. 2004; Torregrossa, et al. 2005; Jutkiewicz, E. M. 2006) and are analgesic (Vanderah, T. W. 2010; Peppin, J. F. and Raffa, R. B. 2015). They have also been shown to reverse the respiratory depression induced by MOR agonists (Su, Y-F. et al. 1998). Therefore, pharmaceutical compositions of the novel compounds disclosed herein, combined with DOR agonists, may be useful in the treatment of pain, anxiety disorders, or mood disorders with increased efficacy or reduced side effects. Alternatively, the opioid modulator and DOR agonist may be dosed separately, as a novel method for treating pain, anxiety disorders or mood disorders.

Non-Limiting Examples of DOR Agonists:

tianeptine, (+)BW373U86, SNC-80, SNC-121, SNC-162, DPI-287, DPI-3290, DPI-221, TAN-67, KN-127, AZD2327, JNJ-20788560, NIH11082, RWJ-394674, ADL5747, ADL5859, UFP-512, AR-M100390, SB-235863, 7-spiroindanyloxymorphone.

Example 16. Preparation of Deuterated Mitragynine Analogs

Deuterated derivatives of mitragynine, 7-hydroxymitragynine, and mitragynine pseudoindoxyl were synthesized according to the synthetic procedures described below and show in Scheme 8.

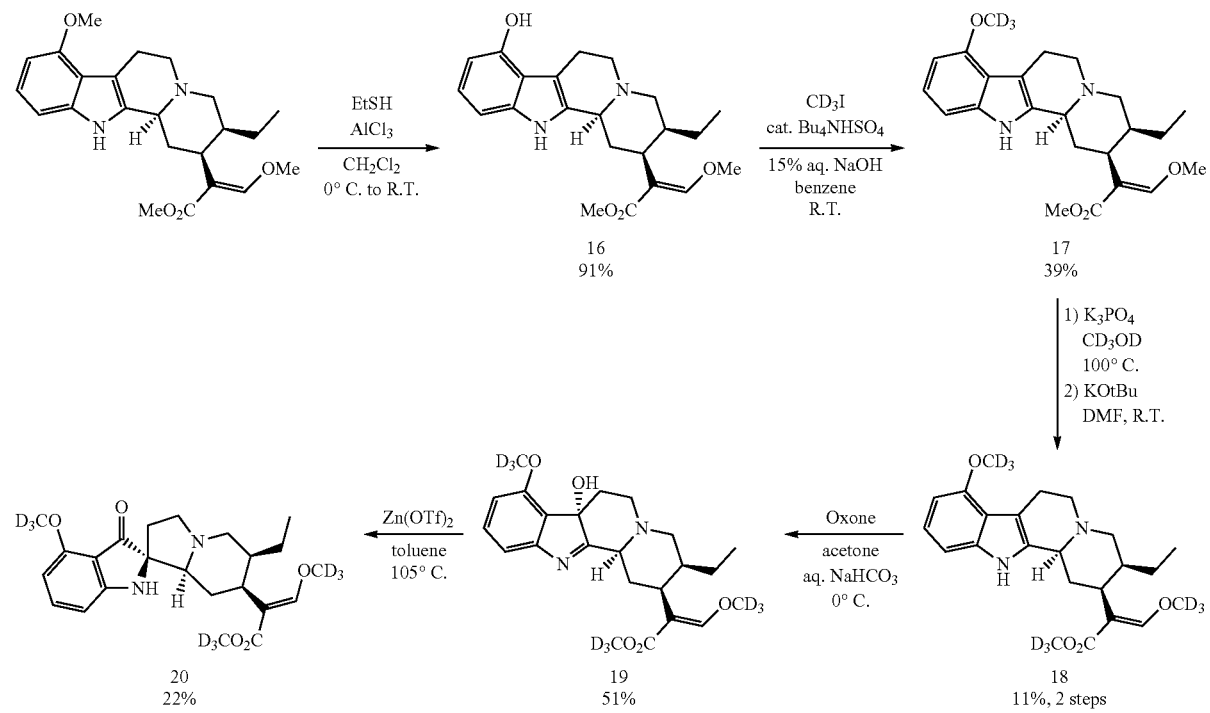

Scheme 8. Synthesis of deuterated mitragynine analogs.

Methyl (Z)-2-((2S,3S,12bS)-3-ethyl-8-hydroxy-1,2,3,4,6,7,12,12b-octahydroindolo[2,3-a]quinolizin-2-yl)-3-methoxyacrylate (16)

To a solution of mitragynine (149 mg, 0.375 mmol) in anhydrous $CH_2Cl_2$ (3.0 mL) at 0° C. was added aluminum chloride (300 mg, 2.25 mmol) followed by ethanethiol (0.50 mL, 419 mg, 6.75 mmol), and the resulting cloudy brownish-orange mixture was allowed to warm to room temperature and stirred for 30 min. The reaction was quenched with saturated aqueous $NaHCO_3$ (30 mL), and the mixture stirred vigorously until all the dark-brown sludge had broken up. The mixture was then extracted with $CH_2Cl_2$ (3×50 mL), and the combined organics were washed with water (25 mL), dried over $Na_2SO_4$, and concentrated to provide pure product 16 as an amorphous, pale-brown solid (131 mg, 91%). $^1$H NMR (400 MHz, CDCl$_3$) δ 7.70 (br s, 1H), 7.44 (s, 1H), 6.95-6.85 (m, 2H), 6.41 (d, J=7.3 Hz, 1H), 4.92 (br s, 1H), 3.73 (s, 3H), 3.71 (s, 3H), 3.26-3.12 (m, 2H), 3.08-2.91 (m, 4H), 2.62-2.43 (m, 3H), 1.85-1.71 (m, 2H), 1.68-1.59 (m, 1H), 1.30-1.15 (m, 1H), 0.87 (t, J=7.3 Hz, 3H); $^{13}$C NMR (101 MHz, CDCl$_3$) δ 169.4, 160.7, 150.0, 138.0, 134.3, 122.1, 116.8, 111.6, 106.9, 104.5, 104.1, 61.7, 61.4, 57.9, 53.7, 51.5, 40.8, 40.0, 30.1, 23.8, 19.6, 13.0; LRMS (APCI+) calcd. for C$_{22}$H$_{29}$N$_2$O$_4$[M+H]$^+$ 385.21, found 385.56.

Methyl (Z)-2-((2S,3S,12bS)-3-ethyl-8-(methoxy-da)-1,2,3,4,6,7,12,12b-octahydroindolo[2,3-a]quinolizin-2-yl)-3-methoxyacrylate (mitragynine-d$_3$=17)

To a solution of 16 (1.54 g, 4.00 mmol) in benzene (145 mL) at room temperature was added 15 m/m aqueous NaOH (3.20 g of solution, 12.00 mmol), tetrabutylammonium hydrogensulfate (407 mg, 1.20 mmol), and iodomethane-d$_3$ (305 μL, 696 mg, 4.80 mmol) and the mixture was stirred for 2 h. Additional iodomethane-d; (76 μL, 174 mg, 1.20 mmol) was then added and stirring was continued for another 2 h. The mixture was then diluted with CHCl$_2$(150 mL), washed with water (2×100 mL) and brine (50 mL), dried over Na$_2$SO$_4$, and concentrated to give a foamy solid (1.71 g). This material was purified by column chromatography (7:3 hexanes:EtOAc+2% Et$_3$N, 4 column volumes→1:1 hexanes:EtOAc+2% Et$_3$N, 4 column volumes) to provide both unconverted starting material (610 mg) and the pure product 17 as a tan foam (629 mg, 39%). H NMR (500 MHz, CDCl$_3$) δ 7.66 (br s, 1H), 7.43 (s, 1H), 6.99 (t, J=7.9 Hz, 1H), 6.90 (dd, J=8.1, 0.7 Hz, 1H), 6.45 (dd, J=7.7, 0.7 Hz, 1H), 3.73 (s, 3H), 3.71 (s, 3H), 3.19-3.08 (m, 2H), 3.07-2.99 (m, 2H), 2.99-2.94 (m, 1H), 2.94-2.89 (m, 1H), 2.57-2.48 (m, 2H), 2.45 (ddd, J=11.5, 3.4, 1.3 Hz, 1H), 1.84-1.73 (m, 2H), 1.65-1.59 (m, 1H), 1.25-1.15 (m, 1H), 0.87 (t, J=7.4 Hz, 3H); $^{13}$C NMR (126 MHz, CDCl$_3$) δ 169.4, 160.7, 154.6, 137.4, 133.8, 121.8, 117.7, 111.6, 107.8, 104.3, 99.7, 61.6, 61.4, 57.8, 54.6 (h, J=21 Hz), 53.9, 51.5, 40.8, 40.1, 30.0, 24.1, 19.2, 13.0.

Methyl-d$_3$ (E)-2-((2S,3S,12bS)-3-ethyl-8-(methoxy-d$_3$)-1,2,3,4,6,7,12,12b-octahydroindolo[2,3-a]quinolizin-2-yl)-3-(methoxy-d$_3$)acrylate (mitragynine-d$_9$=18)

Compound 17 (402 mg, 1.00 mmol) and K$_3$PO$_4$ (425 mg, 2.00 mmol) were combined in methanol-d$_4$ (8.0 mL) and the mixture was heated to 100° C. in a sealed vial and stirred for 25 h (NMR confirms exchange of methyl groups for deuterated methyl groups). The reaction mixture was then diluted with CH$_2$Cl$_2$ (80 mL), washed with saturated aqueous NaHCO$_3$ (40 mL) and water (40 mL), dried over Na$_2$SO$_4$, and concentrated to provide the crude, deuterated acetal intermediate as a tan foam (299 mg). This material was combined with potassium tert-butoxide (302 mg, 2.69 mmol, ~4 equivalents), anhydrous DMF (42 mL) was added, and the mixture was left to stir at room temperature for 19 h (Note: conversion of acetal to product may be monitored by NMR, but conversion is incomplete). The reaction was then poured into water (250 mL) and extracted with Et$_2$O (200 mL, 2×100 mL, 50 mL). The combined organics were washed with water (2×50 mL) and brine (50 mL), dried over Na$_2$SO$_4$, and concentrated to give a pale-orange foam (159 mg). This material was split in two and each half purified by repeated preparative TLC (7:3 hexanes:EtOAc+2% Et$_3$N, for each plate solvent was run up 2× to provide additional resolution) to provide the pure product 18 as a pale-yellow foam (44.6 mg, 11% over 2 steps). $^1$H NMR (500 MHz, CDCl$_3$) δ 7.77 (br s, 1H), 7.43 (s, 1H), 6.99 (t, J=7.9 Hz, 1H), 6.90 (d, J=8.0 Hz, 1H), 6.45 (d, J=7.7 Hz, 1H), 3.19-3.08 (m, 2H), 3.07-3.00 (m, 2H), 3.00-2.95 (m, 1H), 2.92 (dd, J=11.3, 5.7 Hz, 1H), 2.58-2.48 (m, 2H), 2.48-2.43 (m, 1H), 1.86-1.74 (m, 2H), 1.67-1.60 (m, 1H), 1.26-1.15 (m, 1H), 0.87 (t, J=7.4 Hz, 3H); $^{13}$C NMR (126 MHz, CDCl$_3$) δ 169.4, 160.6, 154.7, 137.4, 133.9, 121.9, 117.8, 111.7, 108.0, 104.3, 99.9, 61.4, 60.8 (h, J=23 Hz), 57.9, 54.6 (h, J=23 Hz), 53.9, 50.7 (h, J=21 Hz), 40.9, 40.1, 30.1, 24.1, 19.3, 13.0.

Methyl-d$_3$ (E)-2-((2S,3S,7aS,12bS)-3-ethyl-7a-hydroxy-8-(methoxy-d$_3$)-1,2,3,4,6,7,7a,12b-octahydroindolo[2,3-a]quinolizin-2-yl)-3-(methoxy-d)acrylate (7-hydroxymitragynine-d$_9$=19)

To a solution of compound 18 (53.0 mg, 0.130 mmol) in acetone (3.9 mL) was added saturated aqueous NaHCO$_3$ (2.6 mL) and the cloudy mixture was cooled to 0° C. A solution of Oxone monopersulfate (80.0 mg, 0.130 mmol with MW=615.5) in water (1.3 mL) was then added dropwise over 15 min. and the reaction was stirred for an additional 30 min. at 0° C. The mixture was then diluted with water (20 mL) and extracted with EtOAc (3×10 mL). The combined organics were washed with brine (5 mL), dried over Na$_2$SO$_4$, and concentrated to give a pale-yellow foam (40.7 mg). This material was purified by preparative TLC (1:1 hexanes:EtOAc+2% Et$_3$N) to give the pure product 19 as a pale-yellow foam (28.2 mg, 51%). $^1$H NMR (500 MHz, CDCl$_3$) δ 7.43 (s, 1H), 7.27 (t, J=7.9 Hz, 1H), 7.19 (d, J=7.6 Hz, 1H), 6.70 (d, J=8.2 Hz, 1H), 3.12 (dd, J=11.1, 2.5 Hz, 1H), 3.07-2.96 (m, 2H), 2.85-2.74 (m, 2H), 2.68-2.59 (m, 2H), 2.52-2.45 (m, 2H), 1.87 (dt, J=13.6, 3.1 Hz, 1H), 1.77-1.55 (m, 3H), 1.30-1.18 (m, 1H), 0.82 (t, J=7.3 Hz, 3H); $^{13}$C NMR (126 MHz, CDCl$_3$) δ 184.4, 169.4, 160.8, 156.0, 155.2, 130.8, 126.7, 114.3, 111.4, 109.0, 81.1, 61.6, 61.0 (h, J=21 Hz), 58.3, 54.8 (h, J=23 Hz), 50.5 (h, J=23 Hz), 50.2, 40.7, 39.4, 35.9, 26.2, 19.1, 13.0.

Methyl-d$_3$ (E)-2-((2S,6'S,7'S,8a'S)-6'-ethyl-4-(methoxy-d$_3$)-3-oxo-2',3',6',7',8',8a'-hexahydro-5'H-spiro[indoline-2,1'-indolizin]-7'-yl)-3-(methoxy-d$_3$)acrylate (mitragynine pseudoindoxyl-d$_3$=20)

Compound 19 (13.0 mg, 0.0307 mmol) and zinc triflate (24.0 mg, 0.0660 mmol; pre-dried by briefly heating under high vacuum) were combined, anhydrous toluene (0.83 mL) was added, and the mixture was heated to 105° C. for 2.5 h. The reaction was then quenched with saturated aqueous NaHCO$_3$ (2 mL) and water (2 mL), extracted with CH$_2$Cl$_2$ (3×5 mL), and the combined organics were dried over Na$_2$SO$_4$ and concentrated to provide a foamy, yellow-brown glass (16.1 mg). This material was purified by repeated preparative TLC (Plate 1: 1:1 hexanes:EtOAc+2% Et$_3$N; Plate 2: 1:1 CH$_2$Cl$_2$:Et$_2$O) to provide the pure product 20 as a foamy, yellow glass (2.9 mg, 22). $^1$H NMR (500 MHz, CDCl$_3$) δ 7.32 (t, J=8.1 Hz, 1H), 7.27 (s, 3H), 6.40 (d, J=8.1 Hz, 1H), 6.13 (d, J=8.0 Hz, 1H), 5.11 (br s, 1H), 3.15-3.09 (m, 2H), 2.81-2.73 (m, 1H), 2.38-2.29 (m, 2H), 2.28-2.11 (m, 3H), 1.94-1.84 (m, 1H), 1.70-1.58 (m, 2H), 1.53-1.47 (m, 1H), 1.24-1.15 (m, 1H), 1.14-1.09 (m, 1H), 0.85 (t, J=7.4 Hz, 3H).

Example 17. Preparation of Additional Deuterated Analogs

Additional deuterated derivatives of 7-hydroxymitragynine and mitragynine pseudoindoxyl are synthesized from compound 17 according to the synthetic methods shown in Scheme 9.

Scheme 9. Synthesis of 7-hydroxymitragynine-d₃ and mitragynine pseudoindoxyl-d₃.

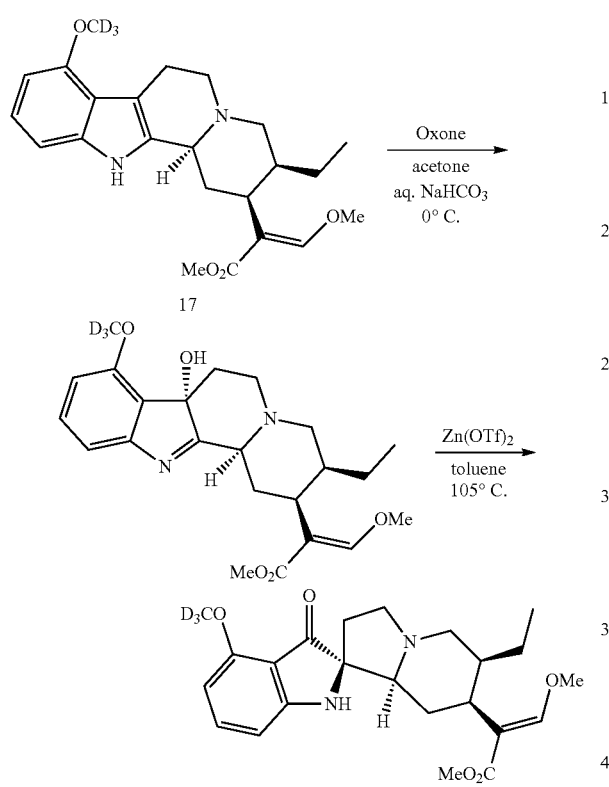

Example 18. Deuteration of Mitragynine Analogs Enhances Metabolic Stability

Deuteration of mitragynine analogs enhances their metabolic stability as evidenced by their longer half-lives relative to their non-deuterated counterparts in a human liver microsome preparation (Table 4).

Stability in Human Liver Microsomes.

Microsomal incubations were carried out in 96-well plates in 5 aliquots of 40 μL each (one for each time point). Liver microsomal incubation medium contained PBS (100 mM, pH 7.4), MgCl2 (3.3 mM), NADPH (3 mM), glucose-6 phosphate (5.3 mM), and glucose-6-phosphate dehydrogenase (0.67 units/ml) with 0.42 mg of liver microsomal protein per mL. Control incubations were performed replacing the NADPH-cofactor system with PBS. Test compound (2 μM, final solvent concentration 1.6%) was incubated with microsomes at 37° C., shaking at 100 rpm. Incubations were performed in duplicates. Five time points over 40 minutes were analyzed. The reactions were stopped by adding 12 volumes of 90% acetonitrile-water to incubation aliquots, followed by protein sedimentation by centrifuging at 5500 rpm for 3 minutes. Supernatants were analyzed for remaining test compound using an HPLC system coupled with a tandem mass spectrometer.

TABLE 4

Half-lives of compounds in human liver microsomes.

| Compound | $t_{1/2}$ (minutes) |
| --- | --- |
| mitragynine | 26.8 |
| 18 | 35.1 |
| 7-hydroxymitragynine | 263 |
| 19 | 394 |

Example 19. Oxidation of Mitragynine Analogs Using Oxone

The oxidation of mitragynine or analogs thereof to the corresponding 7-hydroxy derivatives may be performed by treatment with Oxone monopersulfate.

Scheme 10. Synthesis of 7-hydroxymitragynine via Oxone oxidation.

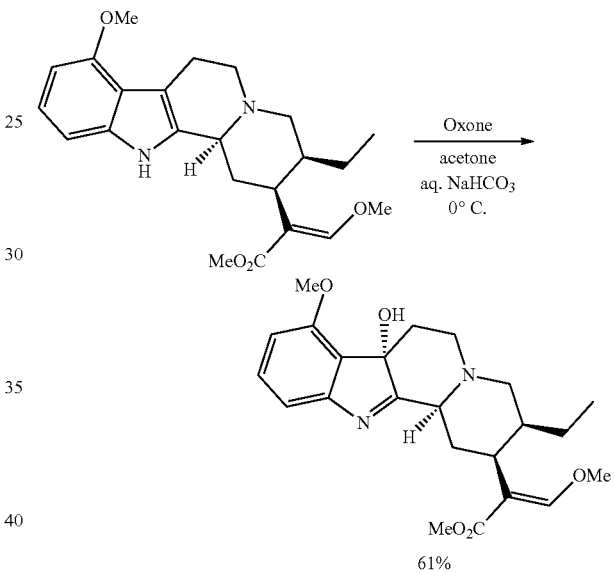

7—Hydroxymitragynine: Ozone Oxidation

To a solution of mitragynine (5.00 g, 12.55 mmol) in acetone (250 mL) at 0° C. was added saturated aqueous NaHCO₃ (25 mL). A solution of Oxone monopersulfate (5.79 g, 9.41 mmol with MW=615.5) in water (25 mL) was then added dropwise over 30 min. and the reaction was stirred for an additional 30 min. at 0° C. The mixture was then diluted with water (50 mL) and extracted with EtOAc (3×). The combined organics were dried over Na₂SO₄ and concentrated to give the crude product. This material was purified by column chromatography (4:1 toluene:EtOAc+53 Et₃N) to give pure 7-hydroxymitragynine as a tan solid (3.15 g, 61%) with spectral properties identical to the material obtained from the PIFA and photochemical oxidation methods (above).

Example 20. Use of Unoxidized Mitragynine Analogs as Prodrugs

Figure 5:
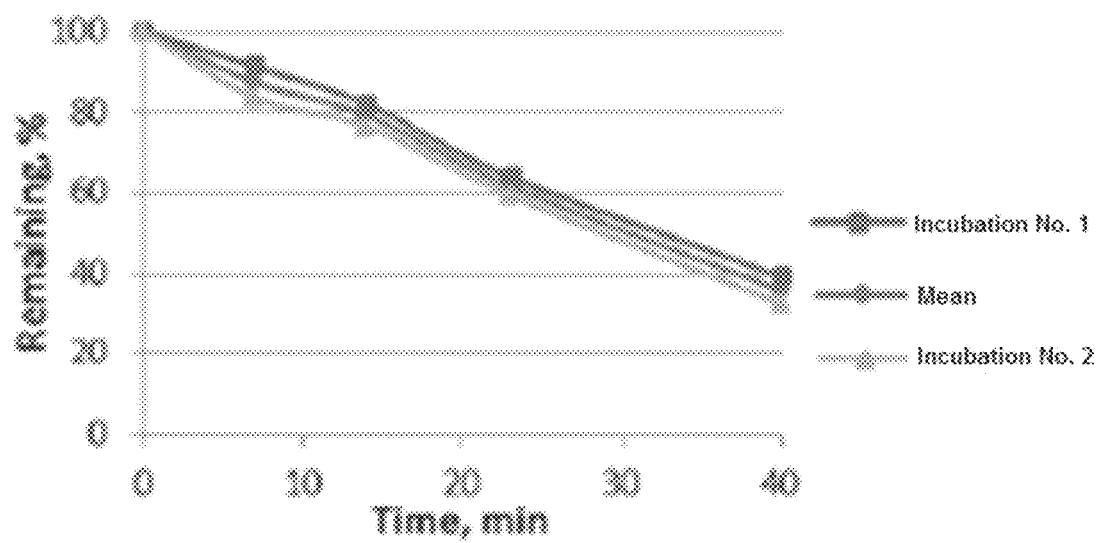
FIG. 5: Loss of mitragynine during incubation with human liver microsomes.
Figure 6:
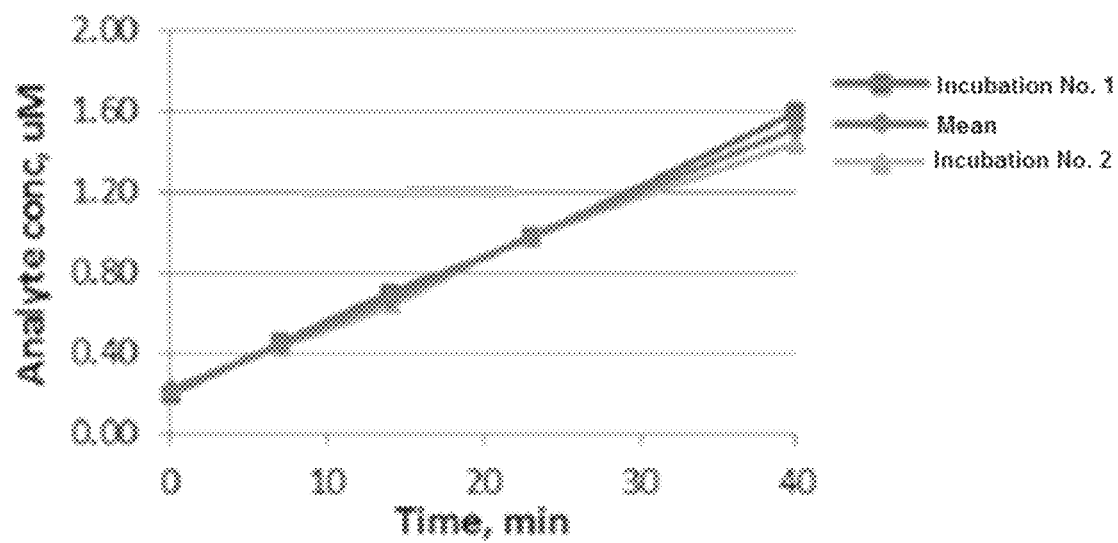
FIG. 6: Appearance of 7-hydroxymitragynine during incubation of mitragynine with human liver microsomes.

When administered to a human or animal subject, mitragynine and other unoxidized derivatives thereof are converted to their corresponding 7-position-oxidized (7-hydroxy) derivatives via cytochrome P450-mediated oxidation (Scheme 11). For example, mitragynine is converted to 7-hydroxymitragynine in a human liver microsome preparation (FIG. 5 and FIG. 6).

Scheme 11. Metabolic conversion of unoxidized mitragynine analogs into their 7-hydroxy derivatives.

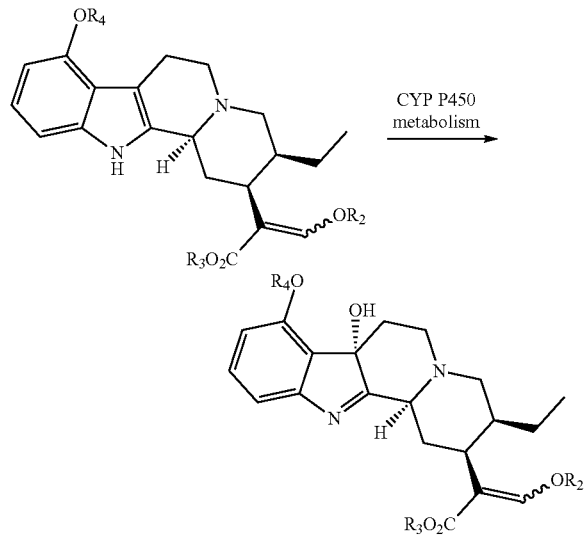

Appearance of 7—Hydroxymitragynine in Human Liver Microsomes.

Microsomal incubations were carried out in 96-well plates in 5 aliquots of 40 μL each (one for each time point). Liver microsomal incubation medium contained PBS (100 mM, pH 7.4), $MgCl_2$(3.3 mM), NADPH (3 mM), glucose-6-phosphate (5.3 mM), and glucose-6-phosphate dehydrogenase (0.67 units/ml) with 0.42 mg of liver microsomal protein per mL. Control incubations were performed replacing the NADPH-cofactor system with PBS. Mitragynine (2 μM, final solvent concentration 1.6 f) was incubated in duplicate with microsomes at 37° C., shaking at 100 rpm. Five time points over 40 minutes were analyzed. The reactions were stopped by adding 12 volumes of 90% acetonitrile-water to incubation aliquots, followed by protein sedimentation by centrifuging at 5500 rpm for 3 minutes. Supernatants were analyzed for remaining mitragynine and formed 7-hydroxymitragynine using an HPLC system coupled with a tandem mass spectrometer.

Discussion

The treatment of mood disorders with conventional MOR agonists is expected to suffer from the same liabilities as their use in the context of pain management. Accordingly, structurally and pharmacologically distinct classes of MOR agonists are needed, with the aim of developing new opioid-based treatments for mood disorders and pain, which lack the classical side effects of these agents.

The psychoactive plant *Mitragyna speciosa*, known as "kratom" in Thailand, or "biak biak" in Malaysia, is a substance which has been used by humans in Southeast Asia for centuries to treat a variety of ailments. The plant material is typically consumed as a tea or chewed directly. At low doses, kratom is primarily used for its stimulating effects. At higher doses, opioid-like effects predominate, and the plant has been used as a general analgesic and as a substitute for opium or to treat opium withdrawal symptoms. Other medicinal applications are also known, including use as a treatment for fever, cough, diarrhea, and depression (Takayama, H. et al. 2004; Adkins, J. E. et al. 2011; Raffa, R. B. et al. 2013; Matsumoto, K. et al. 2014; Takayama, H. et al. 2002).

In light of its well documented medicinal properties, the molecular constituents of *Mitragyna speciosa* responsible for its psychoactive effects have been studied, with more than 20 unique indole alkaloids having been identified in the plant (Takayama, H. et al. 2004; Adkins, J. E. et al. 2011; León, F. et al. 2009). The indole alkaloid mitragynine has been universally cited as the primary alkaloid constituent of *Mitragyna speciosa*, accounting for up to 66% by mass of crude alkaloid extracts (Takayama, H. et al. 2004). The other major alkaloids in the plant have been found to include paynantheine, speciogynine, and speciociliatine (Takayama, H. et al. 2004). The quantities of these major alkaloids, along with a wide variety of minor alkaloids, are considerably varied amongst different regional varieties of the plant and also depend on plant age, facts that considerably complicate the interpretation of reported psychoactive effects from the raw plant material (Takayama, H. et al. 2004; Adkins, J. E. et al. 2011; León, F. et al. 2009). Amongst the minor alkaloids, the oxidized derivative 7-hydroxymitragynine (7-OH) (Ponglux, D. et al. 1994) is of particular interest, as it has been reported to induce analgesic effects mediated through agonist activity at the mu-opioid receptor (MOR), exceeding in potency those of the prototypical opioid agonist morphine (Takayama, H. et al. 2002; Matsumoto, K. et al. 2004).

The mechanism of action of *Mitragyna* alkaloids has also been studied both in vitro and in vivo. In particular, Takayama and coworkers have accumulated a large body of evidence implicating the opioid receptor system as the primary mediator of the psychoactive effects of these alkaloids. Specifically, both mitragynine and 7-OH exhibit nanomolar binding affinities for the MOR and possess functional activity in tissue assays (Takayama, H. et al. 2002; Matsumoto, K. et al. 2004). Likewise, the antinociceptive effects of mitragynine and 7-OH in several rodent models are also inhibited by naloxone Takayama, H. et al. 2002; Matsumoto, K. et al. 2004; Matsumoto, K. et al. 1996).

Studies (Kruegel, A. C. et al. 2016) show that mitragynine, 7-hydroxymitragynine, and mitragynine pseudoindoxyl act as partial MOR agonists. More interestingly, all three compounds act as biased agonists at this receptor, inducing signaling through G protein-dependent pathways while failing to recruit beta-arrestin. Activation of arrestin-dependent signaling pathways has been implicated in many of the side effects of traditional MOR agonists (e.g. morphine) (Raehal, K. M. et al. 2011; Pradhan, A. A. et al. 2012; DeWire, S. M. et al. 2013; Soergel, D. G. et al. 2014). Thus, G protein-biased agonists at this receptor (e.g. mitragynine and its analogs) represent potential opioid analgesics with reduced side effects.

Surprisingly, these studies have also demonstrated that mitragynine, 7-hydroxymitragynine, and mitragynine pseudoindoxyl act as competitive kappa-opioid receptor (KOR) antagonists. This KOR antagonism represents an unexpected biological activity in this class that renders these compounds useful as treatments for depression, anxiety, and other mood disorders. KOR antagonists have demonstrated efficacy in animal models of depression and several compounds in this class are currently undergoing clinical trials for this condition (Mague, S. D. et al. 2003; Land, B. B. et al. 2008; Bruijnzeel, A. W. 2009; Urbano, M. et al. 2014). Moreover, this KOR antagonist activity, in combination with the biased partial agonist activity at the MOR, may render these compounds particularly efficacious in treating mood disorders. The MOR agonist activity of mitragynine, 7-hydroxymitragynine, and mitragynine pseudoindoxyl is synergistic with the KOR antagonism of these compounds.

The present invention also provides two isomeric analogs of mitragynine and 7-hydroxymitragynine, (Z)-mitragynine and (Z)-7-hydroxymitragynine respectively, which have been obtained through total synthesis. These compounds are active as MOR agonists and thus, are useful as novel analgesics or treatments for mood and anxiety disorders. Further, they are unexpectedly more selective for the MOR over the KOR and delta-opioid receptor (DOR). Both natural products exhibit antagonism at KOR and/or DOR, which is significantly reduced in their Z-isomers.

Also described in the present invention are deuterated mitragynine analogs and novel synthetic methods of preparing the same. The exemplified analogs of mitragynine, 7-hydroxymitragyine, and mitragynine pseudoindoxyl are >95% enriched in deuterium at either one or all three methyl groups. Said compounds are more metabolically stable than their non-deuterated counterparts and are thus useful as longer acting treatments for pain or mood and anxiety disorders. The deuterated analogs are also useful as labelled internal standards in mass spectrometric analytical methods detecting their non-deuterated counterparts in chemical or biological samples.

The present invention also describes a method of using mitragynine and other such unoxidized analogs as prodrugs to deliver 7-hydroxymitragynine and other such 7-position-oxidized analogs to a human or animal subject. For example, mitragynine is administered to a subject and is converted to 7-hydroxymitragynine via cytochrome P450-mediated oxidation. Since 7-hydroxymitragynine is a more potent agonist of MOR and also a more potent analgesic in vivo, administration of mitragynine affords significant MOR-mediated effects due to its conversion to the 7-hydroxymitragynine metabolite. Similarly, other mitragynine analogs serve as prodrugs for their corresponding 7-hydroxy derivatives.

Lastly, the invention provides novel methods of synthesizing 7-hydroxymitragynine via photochemical or Oxone oxidation of mitragynine. Both the photochemical and Oxone oxidations may also be applied generally to prepare 7-hydroxy derivatives of other compounds in the mitragynine molecular scaffold. Both the photooxidation and Oxone procedures are higher yielding and produce fewer byproducts compared to the literature method employing phenyliodine bis(trifluoroacetate) (PIFA) (Takayama, H. et al. 2014). The invention also describes diverse synthetic methods to encompass chemical space around the mitragynine molecular scaffold and its oxidized derivatives (including a total synthesis).

REFERENCES

Adkins, J. E. et al. *Curr. Top. Med. Chem.* 2011, 11, 1165-1175.
Andrasik, Stephen. *Singlet Oxygen Generation Using New Fluorene-Based Photosensitizers Under One-and Two-Photon Excitation*. Ph.D. Thesis. University of Central Florida, 2007.
Besson, A. et al. *Psychopharmacology* 1996, 123, 71-78.
Bodkin, J. A. et al. *J. Clin. Psychopharmacol.* 1995, 15, 49-57.
Bruijnzeel, A. W. *Brain Res. Rev.* 2009, 62 (1), 127-146.
Dean, A. J.; Bell, J.; Christie, M. J.; Mattick, R. P. *Eur. Psychiatry* 2004, 19, 510-513.
DeWire, S. M. et al. *J. Pharmacol. Exp. Ther.* 2013, 344 (3), 708-717.
Emrich, H. M.; Vogt, P.; Herz, A. *Ann. N. Y. Acad. Sci.* 1982, 398, 108-112.
Fichna, J.; Janecka, A.; Piestrzeniewicz, M.; Costentin, J.; do Rego, J.-C. *Neuropsychopharmacology* 2007, 32, 813-821.
Gassaway, M. M. et al. *Transl. Psychiatry* 2014, 4, e411.
Gerner, R. H. et al. *Arch. Gen. Psychiatry* 1980, 37, 642-647.
Grinnell, S. G. et al. *J. Pharmacol. Exp. Ther.* 2014, 350, 710-718.
Jutkiewicz, E. M. Mol. *Interv.* 2006, 6, 162-169.
Karp, J. F.; Butters, M. A.; Begley, A. E.; Miller, M. D.; Lenze, E. J.; Blumberger, D. M.; Mulsant, B. H.; Reynolds, C. F. *J. Clin. Psychiatry* 2014, 75, e785-e793.
Kraepelin, E. *Einfahrung in die psychiatrische Klinik: Zweiunddreissig Vorlesungen*; Barth: Leipzig, 1905.
Kramer, M. S. et al. *Neuropsychopharmacology* 2004, 29, 385-392.
Kruegel, A. C. et al. *J. Am. Chem. Soc.* 2016, 138 (21), 6754-6764.
Land, B. B.; Bruchas, M. R.; Lemos, J. C.; Xu, M.; Melief, E. J.; Chavkin, C. *J. Neurosci.* 2008, 28 (2), 407-414.
Largent-Milnes, T.; Yamamoto, T.; Nair, P.; Moulton, J.; Hruby, V.; Lai, J.; Porreca, F.; Vanderah, T. *Br. J. Pharmacol.* 2010, 161, 986-1001.
León, F.; Habib, E.; Adkins, J. E.; Furr, E. B.; McCurdy, C. R.; Cutler, S. J. *Nat. Prod. Commun.* 2009, 4, 907-910.
Mague, S. D. et al. *J. Pharmacol. Exp. Ther.* 2003, 305 (1), 323-330.
Mao, J.; Price, D. D.; Caruso, F. S.; Mayer, D. J. *Pain* 1996, 67, 361-368.
Matsumoto, K. *Pharmacological Studies on 7-Hydroxymitragynine, Isolated from the Thai Herbal Medicine Mitragyna speciosa: Discovery of an Orally Active Opioid Analgesic*. Ph.D. Dissertation, Chiba University, Chiba, Japan, 2006.
Matsumoto, K.; Mizowaki, M.; Suchitra, T.; Takayama, H.; Sakai, S.; Aimi, N.; Watanabe, H. *Life Sci.* 1996, 59, 1149-1155.
Matsumoto, K. et al. J. Pharmacol. Exp. Ther. 2014, 348, 383-392.
Moskal, J. R.; Kuo, A. G.; Weiss, C.; Wood, P. L.; Hanson, A. O.; Kelso, S.; Harris, R. B.; Disterhoft, J. F. *Neuropharmacology* 2005, 49, 1077-1087.
Murrough, J. W. et al. *Am. J. Psychiatry* 2013, 170, 1134-1142.
Negri, A. et al. *J. Chem. Inf. Model.* 2013, 53 (3), 521-526.
Overstreet, D. H.; Naimoli, V. M.; Griebel, G. *Pharmacol. Biochem. Behav.* 2010, 96, 206-210.
Panocka, I. et al. *Peptides* 2001, 22, 1037-1042.
Pasternak, G. W. *Clin. J. Pain* 2010, 26 (Supplement 10), S3-S9.
Pasternak, G. W.; Pan, Y.-X. *Pharmacol. Rev.* 2013, 65, 1257-1317.
Peppin, J. F.; Raffa, R. B. *J. Clin. Pharm. Ther.* 2015, 40, 155-166.
Ponglux, D.; Wongseripipatana, S.; Takayama, H.; Kikuchi, M.; Kurihara, M.; Kitajima, M.; Aimi, N.; Sakai, S. *Planta Med.* 1994, 60 (6), 580-581.
Pradhan, A. A. et al. *Br. J. Pharmacol.* 2012, 167 (5), 960-969.
Raffa, R. B. et al. *J. Med. Chem.* 2013, 56, 4840-4848.
Raehal, K. M. et al. *Pharmacol. Rev.* 2011, 63 (4), 1001-1019.
Rives, M.-L.; Rossillo, M.; Liu-Chen, L.-Y.; Javitch, J. A. *J. Biol. Chem.* 2012, 287 (32), 27050-27054.

Robinson, J. E.; Fish, E. W.; Krouse, M. C.; Thorsell, A.; Heilig, M.; Malanga, C. J. *Psychopharmacology* 2012, 220, 215-224.

Rojas-Corrales, M. O.; Gibert-Rahola, J.; Micó, J. A. *Life Sci.* 1998, 63, PL175-PL180.

Rojas-Corrales, M. O.; Berrocoso, E.; Gibert-Rahola, J.; Micó, J. A. *Life Sci.* 2002, 72, 143-152.

Saitoh, A.; Kimura, Y.; Suzuki, T.; Kawai, K.; Nagase, H.; Kamei, J. *J. Pharmacol. Sci.* 2004, 95, 374-380.

Salome, N.; Stemmelin, J.; Cohen, C.; Griebel, G. *Pharmacol. Biochem. Behav.* 2006, 83, 533-539.

Shapira, N. A.; Keck, P. E.; Goldsmith, T. D.; McConville, B. J.; Eis, M.; McElroy, S. L. *Depress. Anxiety* 1997, 6, 170-173.

Shapira, N. A.; Verduin, M. L.; DeGraw, J. D. *J. Clin. Psychiatry* 2001, 62, 205-206.

Soergel, D. G. et al. *Pain* 2014, 155 (9), 1829-1835.

Stevenson, G. W. et al. *Pharmacol. Biochem. Behav.* 2015, 132, 49-55.

Stoll, A. L.; Rueter, S. *Am. J. Psychiatry* 1999, 156, 2017.

Su, Y. F.; McNutt, R. W.; Chang, K. J. *J. Pharmacol. Exp. Ther.* 1998, 287, 815-823.

Takayama, H. et al. *J. Med. Chem.* 2002, 45, 1949-1956.

Takayama, H. *Chem. Pharm. Bull.* 2004, 52, 916-928.

Takayama, H. et al. U.S. Pat. No. 8,648,090 B2, Feb. 11, 2014.

Torregrossa, M. M.; Folk, J. E.; Rice, K. C.; Watson, S. J.; Woods, J. H. *Psychopharmacology (Berl).* 2005, 183, 31-40.

Trujillo, K. A.; Akil, H. *Brain Res.* 1994, 633, 178-188.

Urbano, M. et al. *Bioorg. Med. Chem. Lett.* 2014, 24 (9), 2021-2032.

Vanderah, T. W. *Clin. J. Pain.* 2010, 26 Suppl, S10-15.

What is claimed is:

1. A compound having the structure:

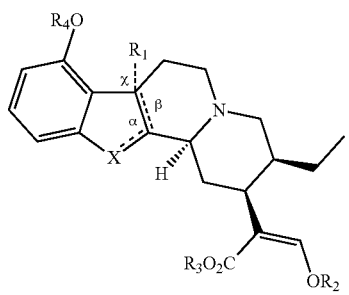

wherein
X is N or NH;
$R_1$ is —OH, —O-alkyl, —O(CO)-alkyl or is absent;
$R_2$ is —H or -alkyl;
$R_3$ is —H or -alkyl;
$R_4$ is —H or -alkyl;
α is a bond and is absent or present;
β is a bond and is absent or present; and
χ is a bond and is absent or present,
wherein when α is absent, β is present, χ is absent, X is NH and $R_1$ is absent, and
wherein when α is present, β is absent, χ is present, X is N and $R_1$ is present,
or a pharmaceutically acceptable salt or ester thereof.

2. The compound of claim 1, wherein $R_2$, $R_3$ and $R_4$ are each methyl.

3. The compound of claim 1, wherein $R_4$ is methyl.

4. The compound of claim 1 having the structure:

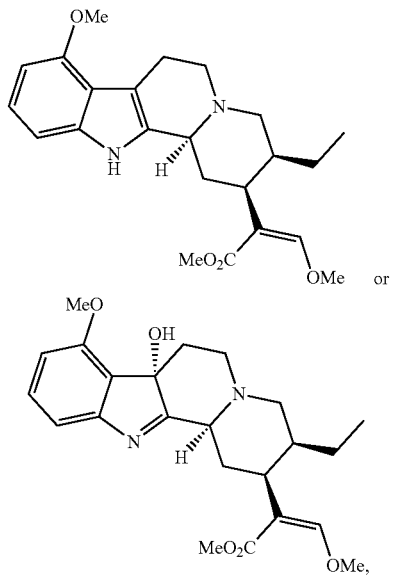

or a pharmaceutically acceptable salt or ester thereof.

5. The compound of claim 1, wherein the compound is deuterium enriched.

6. The compound of claim 5, wherein the compound is deuterium enriched at the $R_4$ position or at the $R_2$, $R_3$ and $R_4$ positions.

7. A pharmaceutical composition comprising the compound of claim 1 and a pharmaceutically acceptable carrier.

8. The composition of claim 7, wherein the pharmaceutical composition is enriched in the compound that contains deuterium in place of —H.

9. The composition of claim 8, wherein $R_2$, $R_3$, and $R_4$ are each methyl and the isotopic purity at each position of the $R_2$ methyl group is 95% or greater in deuterium; the isotopic purity at each position of the $R_3$ methyl group is 95% or greater in deuterium; and the isotopic purity at each position of the $R_4$ methyl group is 95% or greater in deuterium.

10. A method of activating a mu-opioid receptor comprising contacting the mu-opioid receptor with the compound of claim 1 so as to thereby activate the mu-opioid receptor, or
of antagonizing a delta-opioid receptor and/or a kappa-opioid receptor comprising contacting the delta-opioid receptor and/or the kappa-opioid receptor with the compound of claim 1 so as to thereby antagonize the delta-opioid receptor and/or the kappa-opioid receptor, or
of treating a subject afflicted with pain, a depressive disorder, a mood disorder or an anxiety disorder comprising administering an effective amount of the compound of claim 1 to the subject so as to thereby treat the subject afflicted with pain, the depressive disorder, the mood disorder or the anxiety disorder, or
of treating a subject afflicted with pain comprising administering to the subject an effective amount of an NMDA receptor antagonist, an NMDA receptor partial agonist, a neurokinin 1 receptor antagonist, or a delta-opioid receptor agonist and an effective amount of the compound of claim 1 so as to thereby treat the subject afflicted with pain, or of treating a subject afflicted with a depressive disorder, a mood disorder or an anxiety disorder comprising administering to the subject an effective amount of an NMDA receptor antagonist, an NMDA receptor partial agonist, a neurokinin 1 receptor antagonist, a neurokinin 2 receptor antagonist, a neurokinin 3 receptor antagonist or a delta-opioid receptor agonist and an effective amount of the compound of claim 1 so as to thereby treat the subject afflicted with the depressive disorder, the mood disorder or the anxiety disorder.

11. A method for systemic in vivo delivery of a first compound of claim 1 having the structure:

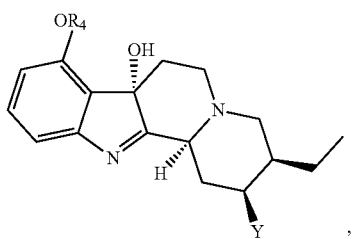

wherein
Y is

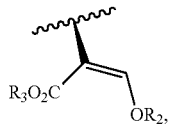

wherein
R$_2$ is —H, or -alkyl, and
R$_3$ is —H, or -alkyl; and
R$_4$ is —H, or -alkyl,
to a subject, the method comprising administering to the subject a second compound of claim 1 having the structure:

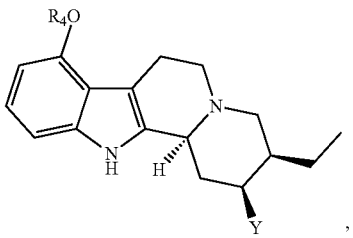

wherein
Y is

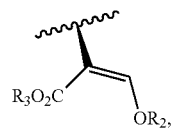

wherein
R$_2$ is —H, or -alkyl, and
R$_3$ is —H, or -alkyl; and
R$_4$ is —H, or -alkyl,
so as to thereby deliver the first compound to the subject.

* * * * *